US012662675B2

(12) United States Patent
Roybal et al.

(10) Patent No.: US 12,662,675 B2
(45) Date of Patent: Jun. 23, 2026

(54) HUMANIZED NOTCH RECEPTORS WITH HINGE DOMAIN

(71) Applicant: The Regents of the University of California, Oakland, CA (US)

(72) Inventors: Kole T. Roybal, San Francisco, CA (US); Raymond Liu, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 767 days.

(21) Appl. No.: 17/995,751

(22) PCT Filed: Apr. 8, 2021

(86) PCT No.: PCT/US2021/026430
§ 371 (c)(1),
(2) Date: Oct. 7, 2022

(87) PCT Pub. No.: WO2021/207526
PCT Pub. Date: Oct. 14, 2021

(65) Prior Publication Data
US 2023/0183709 A1      Jun. 15, 2023

Related U.S. Application Data

(60) Provisional application No. 63/165,588, filed on Mar. 24, 2021, provisional application No. 63/007,807, filed on Apr. 9, 2020.

(51) Int. Cl.
| | |
|---|---|
| *C12N 15/11* | (2006.01) |
| *C07K 14/705* | (2006.01) |
| *C07K 16/28* | (2006.01) |
| *C12N 15/113* | (2010.01) |
| *C12N 15/86* | (2006.01) |
| *A61K 39/00* | (2006.01) |

(52) U.S. Cl.
CPC ........ *C12N 15/1138* (2013.01); *C07K 14/705* (2013.01); *C07K 16/2803* (2013.01); *C07K 16/2878* (2013.01); *C12N 15/86* (2013.01); *A61K 2039/505* (2013.01); *C07K 2317/622* (2013.01); *C07K 2317/73* (2013.01); *C07K 2319/03* (2013.01); *C07K 2319/80* (2013.01); *C12N 2830/00* (2013.01)

(58) Field of Classification Search
CPC C12N 15/1138; C12N 15/86; C12N 2830/00; C12N 2310/20; C12N 2310/315; C12N 2740/16043; C12N 2310/321; C12N 2310/3521; C07K 14/705; C07K 16/2803; C07K 16/2878; C07K 2317/622; C07K 2317/73; C07K 2319/03; C07K 2319/80; C07K 2319/00; C07K 14/70517; C07K 14/7051; C07K 2317/53; A61K 2039/505; A61K 2121/00; A61K 2300/00; A61K 38/00; A61K 40/31; A61P 35/00
See application file for complete search history.

(56) References Cited

U.S. PATENT DOCUMENTS

| | | | |
|---|---|---|---|
| 6,333,167 | B1 | 12/2001 | Quinet et al. |
| 10,058,624 | B2 | 8/2018 | Doering et al. |
| 10,266,592 | B2 | 4/2019 | Jensen |
| 11,155,616 | B2 | 10/2021 | Jensen |
| 11,325,957 | B2 | 5/2022 | Gilbert et al. |
| 12,202,897 | B2 | 1/2025 | Jensen |
| 12,297,243 | B2 | 5/2025 | Emtage et al. |
| 2014/0031247 | A1* | 1/2014 | Li .......... C07K 16/28 |
| | | | 530/387.9 |
| 2014/0322183 | A1* | 10/2014 | Milone ......... C07K 16/18 |
| | | | 435/328 |

(Continued)

FOREIGN PATENT DOCUMENTS

| | | |
|---|---|---|
| WO | WO-2018/236825 A1 | 12/2018 |
| WO | WO-2019/079486 A1 | 4/2019 |

(Continued)

OTHER PUBLICATIONS

Extended European Search Report mailed on May 13, 2024, for EP Patent Application No. 21785532.9, 28 pages.
Mumm, J.S. et al. (Feb. 2000). "A ligand-induced extracellular cleavage regulates gamma-secretase-like proteolytic activation of Notch1," *Mol Cell* 5(2):197-206.
Steinbuck, M.P. (Jun. 1, 2018). "A Review of Notch Processing With New Insights Into Ligand-Independent Notch Signaling in T-Cells," *Frontiers in Immunology* 9:1230.
Struhl, G. et al. (Sep. 2000). "Requirements for presenilin-dependent cleavage of notch and other transmembrane proteins," *Mol Cell* 6(3):625-636.

(Continued)

*Primary Examiner* — Nelson B Moseley, II
*Assistant Examiner* — Josephine K Darpolor
(74) *Attorney, Agent, or Firm* — Mintz Levin Cohn Ferris Glovsky and Popeo, P.C.

(57) ABSTRACT

The present disclosure generally relates to, inter alia, a new class of chimeric Notch receptors containing a fully human-ized transcriptional effector, engineered to modulate gene expression and cellular activities in a ligand-dependent manner. The new chimeric Notch receptors surprisingly retain the ability to transduce signals in response to ligand binding despite that the Notch extracellular subunit (NEC), which includes the negative regulatory region (NRR) pre-viously believed to be essential for the functioning of Notch receptors is completely absent. In addition, the new recep-tors described herein incorporate an extracellular oligomer-ization domain to promote oligomer formation of the chi-meric receptors. Also provided are compositions and methods useful for producing such receptors, nucleic acids encoding same, engineered cells genetically modified with the nucleic acids, as well as methods for modulating an activity of a cell and/or for the treatment of various diseases such as cancers.

21 Claims, 17 Drawing Sheets

Specification includes a Sequence Listing.

(56)         References Cited

U.S. PATENT DOCUMENTS

| | | | |
|---|---|---|---|
| 2018/0355011 A1* | 12/2018 | Lim ................... | C07K 16/2803 |
| 2019/0345261 A1 | 11/2019 | Lebowitz et al. | |
| 2021/0130845 A1 | 5/2021 | Ostertag et al. | |
| 2021/0388347 A1 | 12/2021 | Iglesias et al. | |
| 2022/0009981 A1 | 1/2022 | Roberts et al. | |
| 2022/0073943 A1 | 3/2022 | Lubelski et al. | |
| 2022/0363728 A1 | 11/2022 | Emtage et al. | |
| 2023/0133209 A1 | 5/2023 | Benenson et al. | |
| 2024/0209357 A1 | 6/2024 | Benenson et al. | |
| 2025/0066435 A1 | 2/2025 | Drever et al. | |

FOREIGN PATENT DOCUMENTS

| | | |
|---|---|---|
| WO | WO-2021/061791 A1 | 4/2021 |
| WO | WO-2021/061856 A1 | 4/2021 |
| WO | WO-2021/061862 A1 | 4/2021 |
| WO | WO-2021/061863 A1 | 4/2021 |
| WO | WO-2021/061872 A1 | 4/2021 |

OTHER PUBLICATIONS

Dudani, J. S. et al. (Mar. 2018). Harnessing Protease Activity to Improve Cancer Care, *Annu. Rev. Cancer Biol.* 2:353-376.
Gordon, W.R. et al. (Jun. 22, 2015, e-published Jun. 4, 2015). "Mechanical Allostery: Evidence for a Force Requirement in the Proteolytic Activation of Notch," *Dev Cell* 33:729-736.
Gordon, W.R. et al. (Oct. 1, 2008). "The molecular logic of Notch signaling—a structural and biochemical perspective," *J. Cell Sci.* 121(Pt 19):3109-3119.
Morsut, L. et al. (Feb. 11, 2016, e-published Jan. 28, 2016). "Engineering Customized Cell Sensing and Response Behaviors Using Synthetic Notch Receptors," *Cell* 164(4):780-791.
Naso M.F. et al. "Adeno-Associated Virus (AAV) as a Vector for Gene Therapy," *BioDrugs* 31(4):317-334.
Nasri, M. et al. (Dec. 2014, e-published Mar. 6, 2014). "Production, purification and titration of a lentivirus-based vector for gene delivery purposes," *Cytotechnology* 66(6):1031-1038.
Porter, D.L. et al.(Aug. 25, 2011, e-published Aug. 10, 2011). "Chimeric Antigen Receptor-Modified T Cells in Chronic Lymphoid Leukemia," *N. Engl J Med.* 365(8):725-733.
Roybal, K.T. et al. (Oct. 6, 2016, e-published Sep. 29, 2016). "Engineering T cells with Customized Therapeutic Response Programs Using Synthetic Notch Receptors," *Cell* 167(2):419-432.
Sakuma, T. et al. (May 1, 2012). "Lentiviral vectors: basic to translational," *Biochem. J.* 443(3):603-618.
Samulski, R.J .et al. (Nov. 2014). "AAV-Mediated Gene Therapy for Research and Therapeutic Purposes," *Annu. Rev. Virol.* 1(1):427-451.
Vidarsson, G. et al. (Oct. 20, 2014). "IgG subclasses and allotypes: from structure to effector functions," *Frontiers Immunol.* 5:520.
Watson, D.J. et al. (2003). "Viral vectors for gene therapy: methods and protocols," Totowa, NJ, USA: Humana Press; 2003. pp. 383-404.
International Search Report mailed on Aug. 11, 2021, for PCT Application No. PCT/US2021/026430, filed Apr. 8, 2021, 4 pages.
Written Opinion mailed on Aug. 11, 2021, for PCT Application No. PCT/US2021/026430, filed Apr. 8, 2021, 6 pages.

* cited by examiner

FIG. 1A

Humanized Hinge-Notch Receptor human DNA-binding domain (DBD) fused to human p65 transactivation domain

FIG. 1B

Activation Profile
Humanized HingeNotch (HNF1A) pRay240

Activation Profile
Humanized RoboNotch (HNF1A) pRay241

Activation Profile
Humanized HingeNotch (HNF1A) pRay242
Flipped Transactivation Domain T cells only + K562s + CD19 K562s 24 hrs    48 hrs    72 hrs

0%    0%    0%

% max of cells

BFP reporter

T cells only    + K562s    + CD19 K562s anti-CD19 scFv truncated CD8 Hinge human p65
human HNF1α DBD

TF  TF

Activation Profile
Humanized HingeNotch (HNF1A) Notch1 Variant pRay 243

Activation Profile

Humanized HingeNotch (HNF1A) Notch1 Variant pRay244

Activation Profile
Humanized HingeNotch (HNF1A) Notch1 Variant pRay250

Activation Profile
Humanized HingeNotch (HNF1A) Notch1 Variant pRay251

T cells only
+ K562s
+ CD19 K562s 24 hrs     48 hrs     72 hrs

0%     9%     19%

% max of cells

BFP reporter anti-CD19 scFv
truncated CD8 hinge
Notch ICD (through aa1825)
human HNF1α DBD
human p65
TF
TF T cells only     + K562s     + CD19 K562s

Activation Profile
Humanized HingeNotch (PAX6) Notch1 Variant pRay253

Activation Profile
Humanized HingeNotch (PAX6) Notch1 Variant pRay254

Activation Profile
Humanized HingeNotch (PAX6) pRay255

HUMANIZED NOTCH RECEPTORS WITH HINGE DOMAIN

CROSS-REFERENCE TO RELATED APPLICATIONS

The present application is a U.S. National Phase Application of PCT International Application No. PCT/US2021/026430, filed on Apr. 8, 2021, designating the United States of America, which is an International Application of and claims priority to U.S. Provisional Patent Application Ser. No. 63/007,807, filed on Apr. 9, 2020; and U.S. Provisional Patent Application Ser. No. 63/165,588, filed on Mar. 24, 2021. The contents of the above-referenced applications are herein expressly incorporated by reference in their entireties, including any drawings.

STATEMENT REGARDING FEDERALLY SPONSORED R&D

This invention was made with government support under grant no. OD025751 awarded by The National Institutes of Health. The government has certain rights in the invention.

INCORPORATION OF THE SEQUENCE LISTING

This application contains a Sequence Listing which is hereby incorporated by reference in its entirety. The accompanying Sequence Listing text file, named "Sequence Listing_048536-678N01US_ST25.txt," was created on Oct. 6, 2022, and is 138 KB.

FIELD

The present disclosure relates generally to new synthetic cellular receptors that bind cell-surface ligands and have selectable specificities and activities. The disclosure also provides compositions and methods useful for producing such receptors, nucleic acids encoding same, host cells genetically modified with the nucleic acids, as well as methods for modulating gene expression, modulating an activity of a cell, and/or for the treatment of various health conditions or diseases, such as cancer.

BACKGROUND

Recent advances in genetic engineering and synthetic biology are enabling the development of novel gene therapies and engineered-cell therapies for the treatment of many diseases and health disorders. For example, a number of first-generation synthetic therapeutic systems including synthetic derivatives of Notch receptors, which are often referred as "SynNotch receptors," have gained significant attention in the recent years due to their considerable potential in the treatment of various types of malignancies. These first-generation SynNotch receptors contain structural modifications of wild-type Notch receptors with user-defined specificities, replacing the extracellular ligand-binding domain (which in wild-type Notch contains multiple EGF-like repeats) with an antibody derivative, and replacing the cytoplasmic domain with a transcription activator of choice, while still relying on the functionality of the Notch negative regulatory region (NRR) (KT Roybal et al., *Cell* 2016 Oct. 6; 167(2):419-32) and L. Morsut et al., *Cell* (2016) 164: 780-91).

However, the deployment of first-generation SynNotch receptor therapies in humans continues to present significant challenges for clinical development. One major potential side effect of first-generation engineered SynNotch receptor therapies is the ability of the engineered SynNotch receptor products to induce host immune responses. Immunogenicity risk factors can be associated with the presence of non-human or partially human sequences in the engineered SynNotch receptors, as well as with the presence of residual viral proteins or other non-human origin proteins used as part of the production of the first-generation engineered SynNotch receptors. These types of immune response have the potential to drive immune rejection of SynNotch-mediated cell therapies, for example possibly affecting engineered cell expansion and persistence, and therefore the overall safety and clinically meaningful response of the treatment.

In addition, first-generation engineered SynNotch receptors are large and approach the packaging limits of traditional lentiviral delivery schemes, preventing ease of delivery and addition of other useful molecular components. For example, the Notch negative regulatory regions (NRRs) span approximately 160 amino acids, making this domain alone the size of some mature proteins, such as insulin or epidermal growth factor (EGF). This is believed to reduce the efficiency of first-generation SynNotch receptor expression and, due to vector capacity-related size constraints, excludes the use of some cloning and transfection vectors.

SUMMARY

The present disclosure relates generally relates to a new class of chimeric oligomerizable Notch receptors containing a humanized transcriptional effector, engineered to modulate gene expression and cellular activities in a ligand-dependent manner. The activity of these fully humanized Notch receptors can be controlled by the presence of an extracellular ligand, allowing for spatial and temporal control of specific gene expression in mammalian cells, as well as for use in modulating cell activities or in treating various health conditions or diseases. Particularly, provided herein are fully humanized Notch receptors that, surprisingly, retain the ability to transduce signals in response to ligand binding despite the complete absence of the Notch extracellular subunit (NEC), including the negative regulatory region (NRR). More particularly, these receptors incorporate an extracellular oligomerization domain to promote formation of an oligomeric form, e.g., dimeric or trimeric forms of the chimeric receptors. Without being bound to any particular theory, this design facilitates oligomerization or clustering of receptors, which improves ligand-activated transcription modulation. Further, these receptors provide a range of sensitivity. Additionally, by completely omitting the native Notch NRR, polynucleotides encoding the receptors of the disclosure can be made smaller than first-generation SynNotch-encoding polynucleotides, which enables the use of vectors having more limited capacity, and facilitates the inclusion of additional elements that would otherwise be excluded by vector capacity-related size constraints.

Accordingly, the new chimeric synthetic Notch receptors described herein (termed "humanized HingeNotch receptors") are compact in size and, since they are fully humanized, are more amenable to the clinical cell manufacturing protocols and use in humans.

In one aspect, provided herein are chimeric polynucleotides including, from N-terminus to C-terminus: (a) an extracellular ligand-binding domain (ECD) having a binding affinity for a selected ligand; (b) a hinge domain capable of promoting oligomer formation of the chimeric polypeptide via intermolecular disulfide bonding; (c) a transmembrane domain (TMD) including one or more ligand-inducible proteolytic cleavage sites; and (d) an intracellular domain (ICD) including a human or humanized transcriptional effector, wherein binding of the selected ligand to the extracellular ligand-binding domain results in cleavage at a ligand-inducible proteolytic cleavage site located between the transcriptional effector and the hinge domain, and wherein the chimeric polypeptide does not include a LIN-12-Notch repeat (LNR) and/or a heterodimerization domain (HD) of a Notch receptor.

Non-limiting exemplary embodiments of the chimeric polypeptides according to the present disclosure include one or more of the following features. In some embodiments, the transmembrane domain further includes a stop-transfer-sequence. In some embodiments, the extracellular domain includes an antigen-binding moiety capable of binding to a ligand on the surface of a cell. In some embodiments, the cell is a pathogen. In some embodiments, the human cell is a tumor cell. In some embodiments, the human cell is a terminally-differentiated cell.

In some embodiments, the chimeric polynucleotides disclosed herein include an extracellular ligand-binding domain having a binding affinity for a selected ligand which includes a protein or a carbohydrate. In some embodiments, the ligand is a cluster of differentiation (CD) marker. In some embodiments, the CD marker is selected from the group consisting of CD1, CD1a, CD1b, CD1c, CD1d, CD1e, CD2, CD3d, CD3e, CD3g, CD4, CD5, CD7, CD8a, CD8b, CD19, CD20, CD21, CD22, CD23, CD25, CD27, CD28, CD33, CD34, CD40, CD45, CD48, CD52, CD59, CD66, CD70, CD71, CD72, CD73, CD79A, CD79B, CD80 (B7.1), CD86 (B7.2), CD94, CD95, CD134, CD140 (PDGFR4), CD152, CD154, CD158, CD178, CD181 (CXCR1), CD182 (CXCR2), CD183 (CXCR3), CD210, CD246, CD252, CD253, CD261, CD262, CD273 (PD-L2), CD274 (PD-L1), CD276 (B7H3), CD279, CD295, CD339 (JAG1), CD340 (HER2), EGFR, FGFR2, CEA, AFP, CA125, MUC-1, MAGE, alkaline phosphatase placental-like 2 (ALPPL2), B-cell maturation antigen (BCMA), green fluorescent protein (GFP), enhanced green fluorescent protein (EGFP), and signal regulatory protein α (SIRPα). In some embodiments, the ligand is selected from cell surface receptors, adhesion proteins, integrins, mucins, lectins, tumor associated antigens, and tumor-specific antigens. In some embodiments, the ligand is a tumor-associated antigen or a tumor-specific antigen. In some embodiments, the extracellular ligand-binding domain includes the ligand-binding portion of a receptor.

In some embodiments, the antigen-binding moiety is selected from the group consisting of an antibody, a nanobody, a diabody, a triabody, a minibody, an F(ab')2 fragment, an F(ab)v fragment, a single chain variable fragment (scFv), a single domain antibody (sdAb), and a functional fragment thereof. In some embodiments, the antigen-binding moiety includes an scFv. In some embodiments, the antigen-binding moiety specifically binds to a tumor-associated antigen selected from the group consisting of CD19, B7H3 (CD276), BCMA, CD123, CD171, CD179a, CD20, CD213A2, CD22, CD24, CD246, CD272, CD30, CD33, CD38, CD44v6, CD46, CD71, CD97, CEA, CLDN6, CLECL1, CS-1, EGFR, EGFRvIII, ELF2M, EpCAM, EphA2, Ephrin B2, FAP, FLT3, GD2, GD3, GM3, GPRCSD, HER2 (ERBB2/neu), IGLL1, IL-11Rα, KIT (CD117), MUC1, NCAM, PAP, PDGFR-β, PRSS21, PSCA, PSMA, ROR1, SSEA-4, TAG72, TEM1/CD248, TEM7R, TSHR, VEGFR2, BCMA (CD269), ALPI, citrullinated vimentin, cMet, and Axl. In some embodiments, the tumor-associated antigen is CD19, BCMA, CEA, HER2, MUC1, CD20, ALPPL2, SIRPα, or EGFR. In some embodiments, the tumor-associated antigen is CD19. In some embodiments, the one or more ligand-inducible proteolytic cleavage sites includes a γ-secretase cleavage site. In some embodiments, the transcriptional effector includes a transcriptional activator, or a transcriptional repressor. In some embodiments, the intracellular domain includes a nuclear localization sequence. In some embodiments, the transcriptional effector includes: (i) a DNA-binding domain and (ii) an effector domain through which the transcriptional effector exerts it effect. In some embodiments, the DNA-binding domain is N-terminally linked to the effector domain. In some embodiments, the DNA-binding domain is C-terminally linked to the effector domain. In some embodiments, the DNA-binding domain is derived from a human hepatocyte nuclear factor 1 homeobox A (HNF1α) protein, a human hepatocyte nuclear factor 1 homeobox B (HNF1β) protein, a human paired box protein (Pax-6), a human paired box protein (Pax-1) protein, a human paired box protein (Pax-2) protein, a human paired box protein (Pax-3) protein, a human paired box protein (Pax-4), or a human paired box protein (Pax-7). In some embodiments, the DNA-binding domain is derived from a human hepatocyte nuclear factor 1 homeobox A (HNF1α) protein. In some embodiments, the HNF1α DNA-binding domain includes the amino acid sequence of SEQ ID NO: 52 or a functional variant thereof. In some embodiments, the DNA-binding domain is derived from a human paired box protein (Pax6). In some embodiments, the Pax6 DNA-binding domain includes the amino acid sequence of SEQ ID NO: 53 or a functional variant thereof.

In some embodiments, the effector domain is selected from the group consisting of a transcriptional activation domain, a transcriptional repressor domain, and an epigenetic effector domain. In some embodiments, the transcriptional activation domain is derived from human nuclear factor NFκB p65 subunit (p65). In some embodiments, the transcriptional activation domain is derived from human nuclear factor NFκB p65 subunit (p65). In some embodiments, the p65 effector domain includes the amino acid sequence of any one of SEQ ID NOS: 54-55 or a functional variant thereof.

In some embodiments, the chimeric polypeptides disclosed herein include an additional proteolytic cleavage site, a signal sequence, a detectable label, a tumor-specific cleavage site, a disease-specific cleavage site, and combinations thereof.

In some embodiments, the hinge domain of the chimeric polypeptides disclosed herein is derived from a CD8α hinge domain, a CD28 hinge domain, a CD152 hinge domain, a PD-1 hinge domain, a CTLA4 hinge domain, an OX40 hinge domain, an IgG1 hinge domain, an IgG2 hinge domain, an IgG3 hinge domain, and an IgG4 hinge domain, or a functional variant of any thereof. In some embodiments, the hinge domain is derived from a CD8α hinge domain or a functional variant thereof. In some embodiments, the hinge domain is derived from a CD28 hinge domain or a functional variant thereof. In some embodiments, the hinge domain is derived from an OX40 hinge domain or a functional variant thereof. In some embodiments, the hinge domain is derived from an IgG4 hinge domain or a functional variant thereof.

In some embodiments, the hinge domain includes an amino acid sequence having at least 80% sequence identity to any one of SEQ ID NOS: 15-19.

In some embodiments, the stop-transfer-sequence (STS) of the chimeric polypeptides disclosed herein includes an amino acid sequence having at least 80% sequence identity to any one of SEQ ID NOS: 31-51.

In some embodiments, the transmembrane domain of the chimeric polypeptides disclosed herein includes an amino acid sequence having at least 80% sequence identity to any one of SEQ ID NOS: 21-30.

In some embodiments, the chimeric polypeptides disclosed herein include (a) a hinge domain including an amino acid sequence having at least 80% sequence identity to any one of SEQ ID NOS: 15-19; (b) a transmembrane domain (TMD) including an amino acid sequence having at least 80% sequence identity to SEQ ID NOS: 21-30; and (c) a STS domain including an amino acid sequence having at least 80% sequence identity to any one of SEQ ID NO: 31-51.

In some embodiments, the chimeric polypeptide includes an amino acid sequence of a length shorter than 500, shorter than 600, shorter than 700, shorter than 800, or shorter than 900 amino acid residues. In some embodiments, the chimeric polypeptide includes an amino acid sequence is of a length shorter than 600 amino acid residues.

In some embodiments, the chimeric polypeptide includes an amino acid sequence having at least 80% sequence identity to any one of SEQ ID NOS: 2, 4-12, and 65-66.

In some embodiments, the following domains are derived from human polypeptides: (a) the extracellular ligand-binding domain, (b) the hinge domain, (c) the TMD, and (d) the ICD. In some embodiments, the following domains are substantially non-immunogenic in a human subject: (a) the extracellular ligand-binding domain, (b) the hinge domain, (c) the TMD, and (d) the ICD. In some embodiments, the ICD is substantially non-immunogenic in a human subject.

In another aspect, provided herein are recombinant nucleic acids including a nucleotide sequence that encodes a chimeric polypeptide as disclosed herein. In some embodiments, the nucleotide sequence is incorporated into an expression cassette or an expression vector. In some embodiments, the expression vector is a viral vector. In some embodiments, the viral vector is a lentiviral vector, an adenovirus vector, an adeno-associated virus vector, or a retroviral vector. In some embodiments, the recombinant nucleic acid further include a nucleic acid sequence encoding a protein of interest operably linked to a promoter, wherein expression of the protein of interest is modulated by the transcriptional effector.

In another aspect, provided herein are recombinant cells including (a) a chimeric polypeptide as disclosed herein and/or (b) a recombinant nucleic acid as disclosed herein. Also provided, in a related aspect, are cell cultures including at least one recombinant cell as disclosed herein and a culture medium. In some embodiments, the recombinant cell is a prokaryotic cell including a recombinant nucleic acid as disclosed herein. In some embodiments, the recombinant nucleic acid is a cloning vector. In some embodiments, the recombinant cell is a eukaryotic cell. In some embodiments, the eukaryotic cell is a mammalian cell. In some embodiments, the mammalian cell is an immune cell, a neuron, an epithelial cell, and endothelial cell, or a stem cell. In some embodiments, the immune cell is a B cell, a monocyte, a natural killer cell, a basophil, an eosinophil, a neutrophil, a dendritic cell, a macrophage, a regulatory T cell, a helper T cell, a cytotoxic T cell, or other T cell. In some embodiments, the recombinant cell includes a first chimeric polypeptide and a second chimeric polypeptide as disclosed herein; and/or b) a first nucleic acid and a second nucleic acid as disclosed herein; wherein the first chimeric polypeptide and the second chimeric polypeptide do not have the same sequence, and/or the first nucleic acid or the second nucleic acid do not have the same sequence. In some embodiments, the first chimeric polypeptide modulates the expression and/or activity of the second chimeric polypeptide. In some embodiments, the recombinant cell further includes an expression cassette encoding a protein of interest operably linked to a promoter, wherein expression of the protein of interest is modulated by the transcriptional effector. In some embodiments, the protein is heterologous to the cell. In some embodiments, the promoter is a phosphoglycerate kinase (PGK) promoter or a yeast GAL4 promoter. In some embodiments, the protein of interest is a cytokine, a cytotoxin, a chemokine, an immunomodulator, a pro-apoptotic factor, an anti-apoptotic factor, a hormone, a differentiation factor, a de-differentiation factor, an immune cell (e.g., TCR or CAR), or a reporter. In some embodiments, the expression cassette is incorporated into a second recombinant nucleic acid molecule that is separate from the recombinant nucleic acid molecule encoding the chimeric polypeptide. In some embodiments, the expression cassette is incorporated into the same recombinant nucleic acid molecule that encodes the chimeric polypeptide.

In another aspect, provided herein are pharmaceutical compositions including a pharmaceutical acceptable carrier and one or more of the following: (a) a recombinant nucleic acid as disclosed herein, and (b) a recombinant cell as disclosed herein. In some embodiments, the disclosed pharmaceutical composition includes a recombinant nucleic acid as disclosed herein and a pharmaceutically acceptable carrier. In some embodiments, the recombinant nucleic acid is encapsulated in a viral capsid or a lipid nanoparticle.

In another aspect, provided herein are methods for modulating an activity of a target cell in a subject, including administering to the subject an effective number of the recombinant eukaryotic cells as disclosed herein, wherein the recombinant cells modulate an activity of the target cell in the subject.

Another aspect relates to methods for modulating an activity of a cell, including: (a) providing a recombinant cell as disclosed herein; and (b) contacting the recombinant cell with the selected ligand, wherein binding of the selected ligand to the extracellular ligand-binding domain results in cleavage of a ligand-inducible proteolytic cleavage site and release of the transcriptional effector, wherein the release of the transcriptional effector results in modulation of an activity of the recombinant cell. In some embodiments, the step of contacting the recombinant cell with the selected ligand is carried out in vivo, ex vivo, or in vitro. In some embodiments, the activity of the cell to be modulated is selected from the group consisting of: expression of a selected gene, proliferation, apoptosis, non-apoptotic death, differentiation, dedifferentiation, migration, secretion of a molecule, cellular adhesion, and cytolytic activity. In some embodiments, the transcriptional effector modulates expression of a gene. In some embodiments, the transcriptional effector modulates expression of a heterologous gene product. In some embodiments, the gene product is selected from the group consisting of chemokine, a chemokine receptor, a chimeric antigen receptor, a cytokine, a cytokine receptor, a differentiation factor, a growth factor, a growth factor receptor, a hormone, a metabolic enzyme, a pathogen-derived protein, a proliferation inducer, a receptor, an RNA guided nuclease, a site-specific nuclease, a T cell receptor, a toxin, a toxin derived protein, a transcriptional regulator, a transcriptional activator, a transcriptional repressor, a translational regulator, a translational activator, a translational repressor, an activating immuno-receptor, an antibody, an apoptosis inhibitor, an apoptosis inducer, an engineered T cell receptor, an immuno-activator, an immuno-inhibitor, and an inhibiting immuno-receptor. In some embodiments, the released transcriptional effector modulates differentiation of the cell, and wherein the cell is an immune cell, a stem cell, a progenitor cell, or a precursor cell.

In another aspect, provided herein are methods for inhibiting an activity of a target cell in a subject, including administering to the subject an effective number of the recombinant cells as disclosed herein, wherein the recombinant cells inhibit an activity of the target cell in the subject. In some embodiments, the target cell is a pathogenic cell. In some embodiments, the pathogenic cell is a cancer cell. In some embodiments, the target cancer cell is an acute myeloma leukemia cell, an anaplastic lymphoma cell, an astrocytoma cell, a B-cell cancer cell, a breast cancer cell, a colon cancer cell, an ependymoma cell, an esophageal cancer cell, a glioblastoma cell, a glioma cell, a leiomyosarcoma cell, a liposarcoma cell, a liver cancer cell, a lung cancer cell, a mantle cell lymphoma cell, a melanoma cell, a neuroblastoma cell, a non-small cell lung cancer cell, an oligodendroglioma cell, an ovarian cancer cell, a pancreatic cancer cell, a peripheral T-Cell lymphoma cell, a renal cancer cell, a sarcoma cell, a stomach cancer cell, a carcinoma cell, a mesothelioma cell, or a sarcoma cell.

Another aspect relates to methods for treating or aiding in the treatment of a health condition (e.g., disease) in a subject, including administering to the subject an effective number of the recombinant cells of the disclosure, wherein the recombinant cells treat the health condition in the subject.

Another aspect of the disclosure relates to methods for making a recombinant cell of the disclosure, including (a) providing a cell capable of protein expression and (b) contacting the provided cell with a recombinant nucleic acid of the disclosure. In some embodiments, the cell is obtained by leukapheresis performed on a sample obtained from a subject, and the cell is contacted ex vivo. In some embodiments, the recombinant nucleic acid is encapsulated in a viral capsid or a lipid nanoparticle.

In another aspect, some embodiments of the disclosure relate to systems for modulating an activity of a cell, inhibiting a target cancer cell, or treating or aiding in the treatment of a health condition (e.g., disease) in a subject in need thereof, wherein the systems include one or more of: a chimeric polypeptide of the disclosure; a nucleic acid of the disclosure; a recombinant cell of the disclosure; and/or a pharmaceutical composition of the disclosure.

Yet another aspect of the disclosure is the use of one or more of the following: (i) a chimeric polypeptide of the disclosure; (ii) a polynucleotide of the disclosure; (iii) a recombinant cell of the disclosure; and (iv) a pharmaceutical composition of the disclosure; for the treatment of a health condition. In some embodiments, the health condition is a disease, such as a cancer.

Another aspect of the disclosure is the use of one or more of the following: (i) a chimeric polypeptide of the disclosure; (ii) a polynucleotide of the disclosure; (iii) a recombinant cell of the disclosure; or (iv) a pharmaceutical composition of the disclosure; for the manufacture of a medicament for the treatment of a health condition, e.g., disease.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

BRIEF DESCRIPTION OF THE DRAWINGS

Figures 1A, 1B:
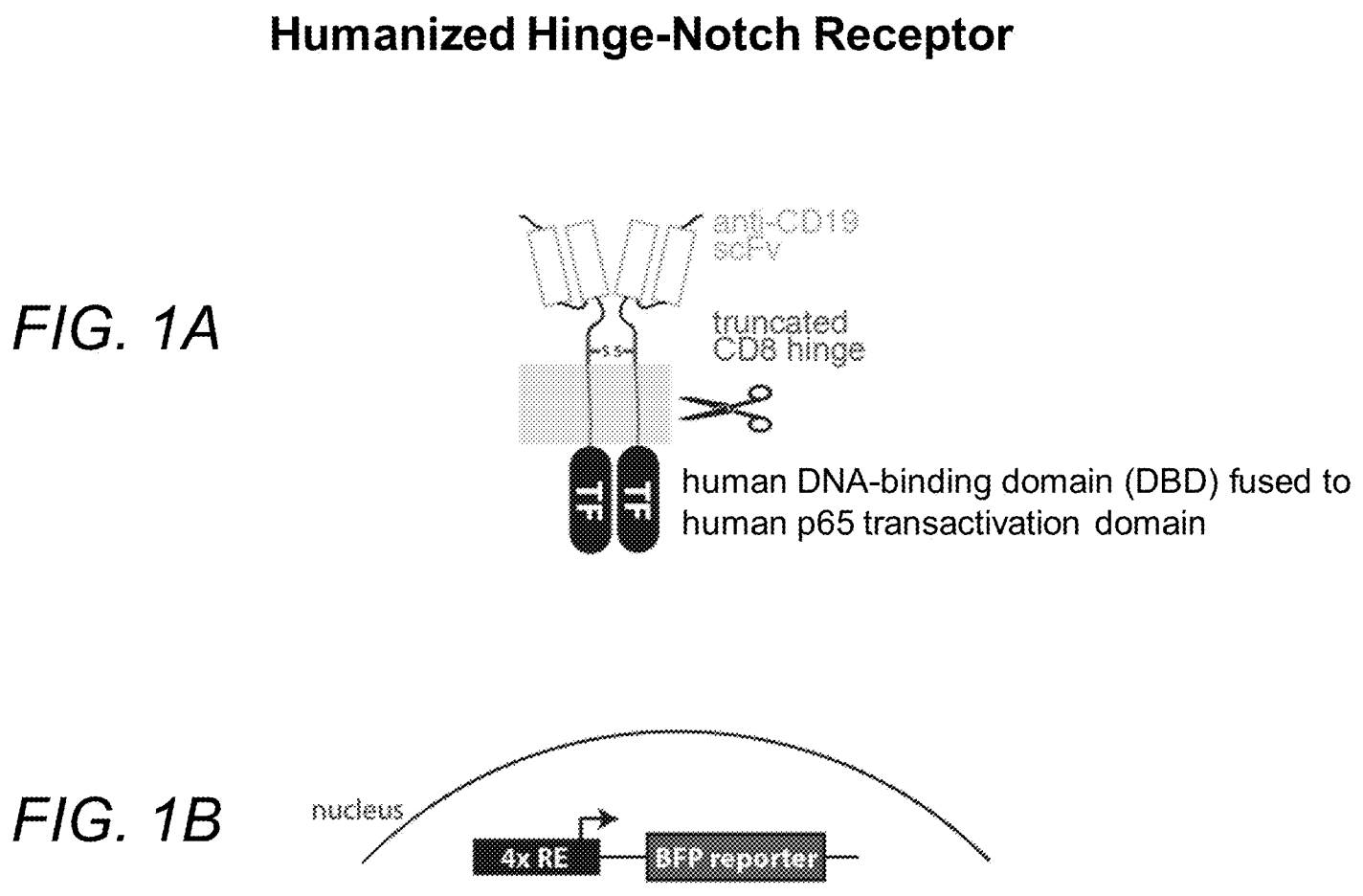

FIG. 1A depicts a schematic of a non-limiting example of a humanized next-generation SynNotch receptor. In this example, a humanized HingeNotch is depicted, where a ligand-recognition domain, anti-CD19 scFv, is fused to a CD8 hinge domain, followed by a Notch transmembrane domain and a humanized transcriptional effector. The transcriptional effector is derived from the DNA-binding domain (DBD) of a human protein, fused to the transactivation domain from human nuclear factor NF-kappa-B p65 subunit (p65). Ligand binding triggers γ-secretase-mediated cleavage of the transmembrane domain, resulting in transcription effector release and translocation to the nucleus. FIG. 1B is a diagram of an exemplary design of a blue fluorescent protein (BFP) reporter whose expression is placed under control of a response-element (RE). Four copies of a DNA sequence recognized by the DNA-binding domain (DBD) in the receptor depicted in FIG. 1A are placed upstream of a minimal promoter and a BFP reporter. Release of the transcription factor, which is triggered by ligand binding to the receptor, results in transcription of the BFP reporter.

FIG. 3A depicts a schematic of the pRay239 receptor, which is a humanized "MiniNotch" receptor containing the following features, in N-terminus to C-terminus direction: antiCD19scFv-Notch1deltaNRR-Notch2STS-HNF1αDBD-p65(361-551). FIG. 3B depicts the activation profile of the receptor pRay239. Approximately 1×10⁵ double positive T cells expressing anti-CD19 receptors and response vectors were cultured alone (upper trace), with 1×10⁵ K562 cells (middle trace), or with 1×10⁵ CD19+K562 cells (lower trace) for 24, 48 or 72 hours. Transcriptional activation of an inducible BFP reporter was measured using a Fortessa X-50 (BD). Percent cells activated by CD19+K562s (lower trace % s) is indicated.

Figures 4A, 4B:
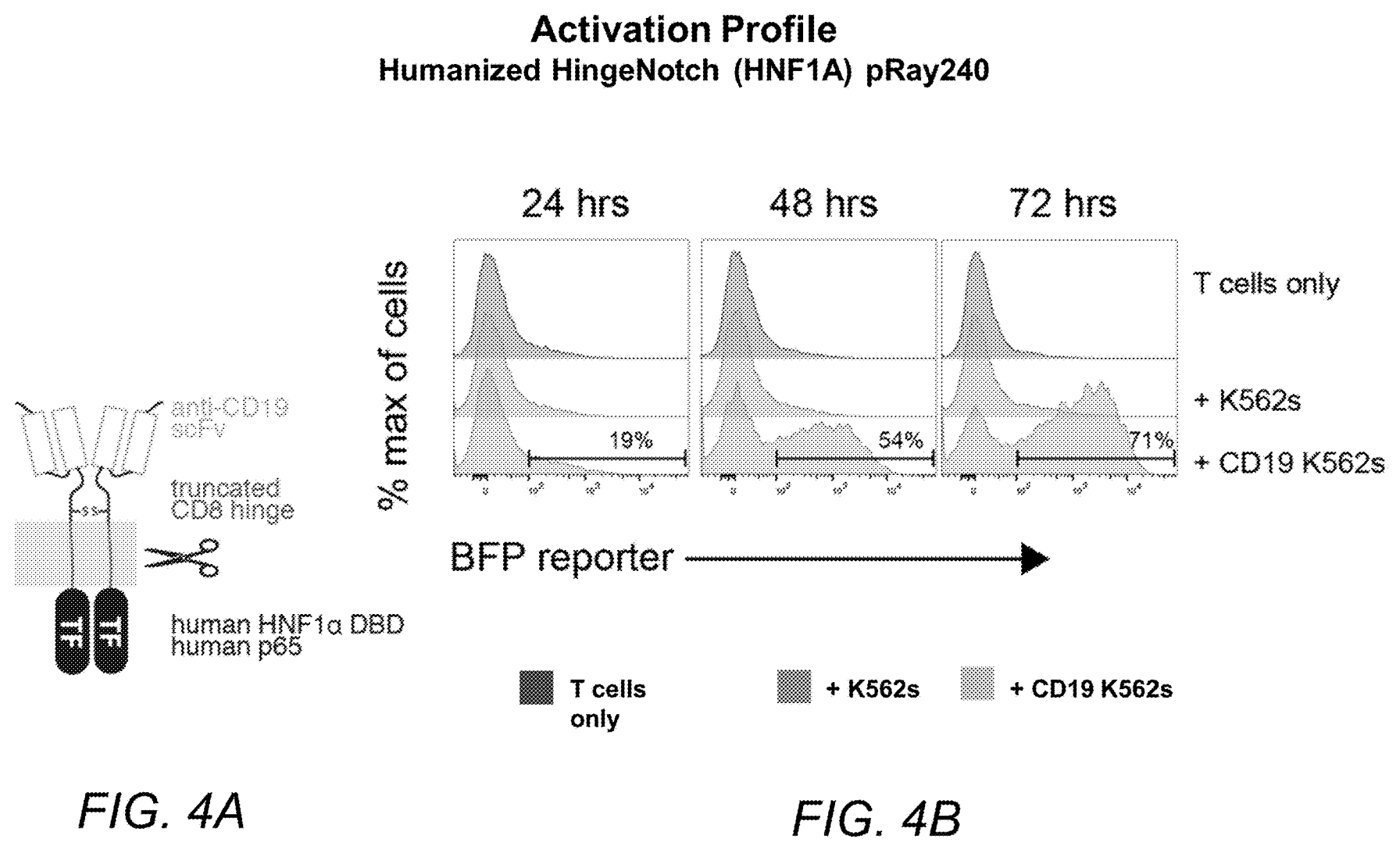

FIGS. 4A-4B schematically summarize the results from experiments performed to assess functionality of pRay240, which is an exemplary humanized "HingeNotch" receptor according to some embodiments of the disclosure. FIG. 4A depicts a schematic of the pRay240 receptor, which is a humanized "HingeNotch" receptor containing the following features, in N-terminus to C-terminus direction: antiCD19scFv-CD8Hinge2-Notch1TMD-Notch2STS- HNF1αDBD-p65(361-551). FIG. 4B depicts the receptor activation profile of the receptor as determined by the same procedure described in FIG. 3B.

Figures 5A, 5B:
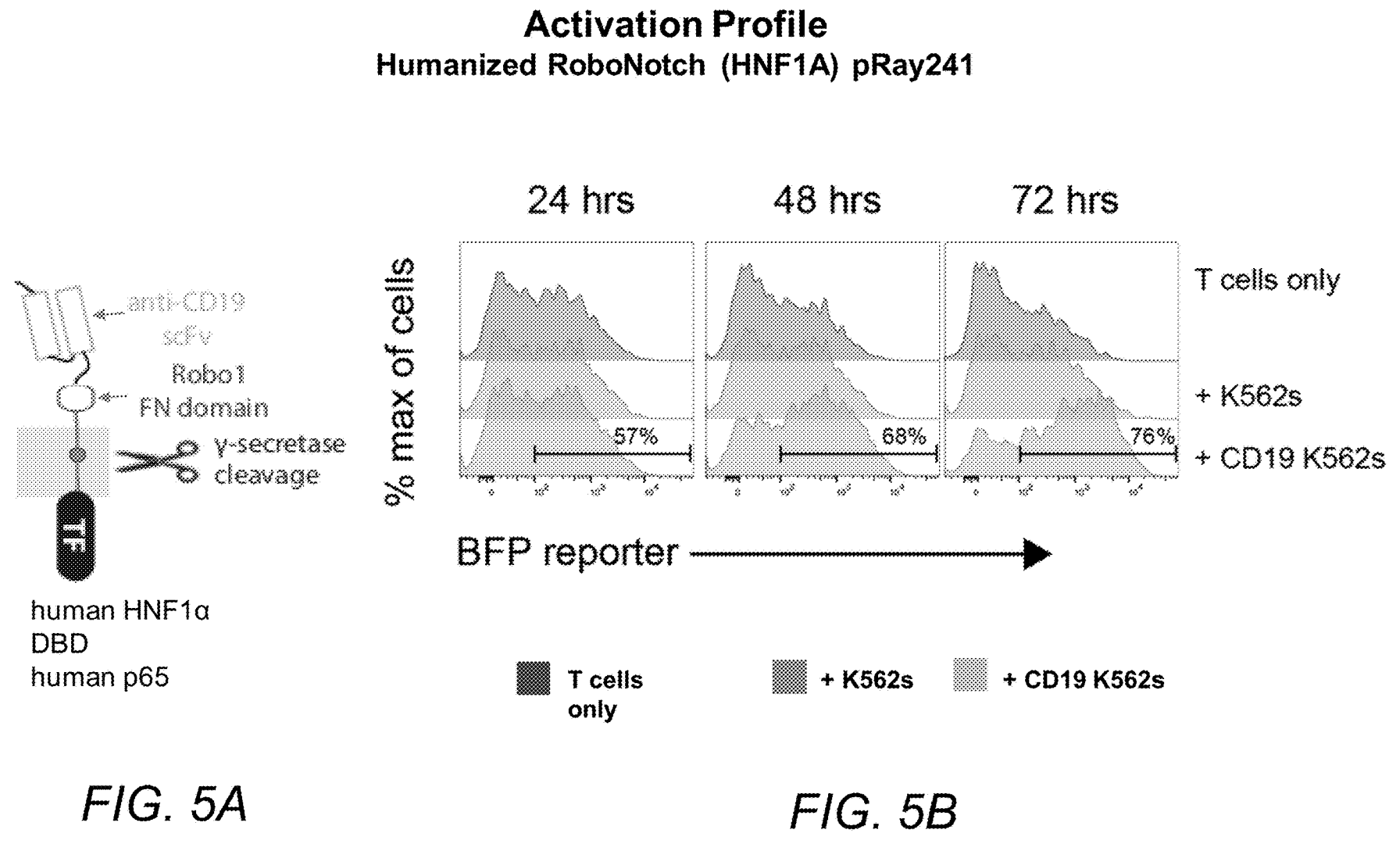

FIGS. 5A-5B schematically summarize the results from experiments performed to assess functionality of pRay241, which is an exemplary humanized "RoboNotch" receptor. FIG. 5A depicts a schematic of the pRay241 receptor, which is a humanized "RoboNotch" receptor containing the following features, in N-terminus to C-terminus direction: antiCD19scFv-RoboFn-Notch1TMD-HNF1αDBD-p65 (361-551). FIG. 5B depicts the activation profile of the receptor as determined by the same procedure described in FIG. 3B.

FIG. 6A depicts a schematic of the pRay242 receptor, which is a humanized "HingeNotch" receptor variant with flipped DBD and TAD, containing the following features, in N-terminus to C-terminus direction: antiCD19scFv-CD8Hinge2-Notch1TMD-Notch2STS-p65(361-551)-HNF1αDBD. FIG. 6B depicts the activation profile of the receptor as determined by the same procedure described in FIG. 3B.

FIG. 7A depicts a schematic of the pRay243 receptor, which is another humanized "HingeNotch" receptor variant with Notch1 extension (1878) and an HNF1α DNA-binding domain, which contains the following features, in N-terminus to C-terminus direction: antiCD19scFv-CD8Hinge2-Notch1(1758-1878)-HNF1αDBD-p65(361-551). FIG. 7B depicts the activation profile of the receptor as determined by the same procedure described in FIG. 3B.

FIG. 8A depicts a schematic of the pRay244 receptor, which is a humanized "HingeNotch" receptor variant with Notch1 extension (1788) and an HNF1α DNA-binding domain, which contains the following features, in N-terminus to C-terminus direction: antiCD19scFv-CD8Hinge2-Notch1 (1758-1788)-HNF1αDBD-p65(361-551). FIG. 8B depicts the activation profile of the receptor as determined by the same procedure described in FIG. 3B.

FIG. 9A depicts a schematic of the pRay250 receptor, which is a humanized "HingeNotch" receptor variant with Notch1 extension (1800) and an HNF1α DNA-binding domain, which contains the following features, in N-terminus to C-terminus direction: antiCD19scFv-CD8Hinge2-Notch1 (1758-1800)-HNF1αDBD-p65(361-551). FIG. 9B depicts the activation profile of the receptor as determined by the same procedure described in FIG. 3B.

FIG. 10A depicts a schematic of the pRay251, which is a humanized "HingeNotch" receptor variant with Notch1 extension (1825) and an HNF1α DNA-binding domain, which contains the following features, in N-terminus to C-terminus direction: antiCD19scFv-CD8Hinge2-Notch1(1758-1825)-HNF1αDBD-p65(361-551). FIG. 10B depicts the activation profile of the receptor as determined by the same procedure described in FIG. 3B.

FIG. 11A depicts a schematic of the pRay252 receptor, which is a humanized "HingeNotch" receptor variant with Notch1 extension (1850) and an HNF1α DNA-binding domain, which contains the following features, in N-terminus to C-terminus direction: antiCD19scFv-CD8Hinge2-Notch1 (1758-1850)-HNF1αDBD-p65(361-551). FIG. 11B depicts the activation profile of the receptor as determined by the same procedure described in FIG. 3B.

FIG. 13A depicts a schematic of the pRay253 receptor, which is a humanized "HingeNotch" receptor variant with Notch1 extension (1878) and a Pax6 DNA-binding domain, which contains the following features, in N-terminus to C-terminus direction: antiCD19scFv-CD8Hinge2-Notch1(1758-1878)-Pax6DBD-p65(428-551). FIG. 13B depicts the activation profile of the receptor pRay253. Approximately $1 \times 10^5$ double positive T cells expressing anti-CD19 receptors and response vectors were cultured alone (upper trace), with $1 \times 10^5$ K562 cells (middle trace), or with $1 \times 10^5$ CD19+K562 cells (lower trace) for 24, 48 or 72 hours. Transcriptional activation of an inducible BFP reporter was measured using a Fortessa X-50 (BD). Percent cells activated by CD19+ K562s (lower trace % s) is indicated.

FIG. 14A depicts a schematic of the pRay254 receptor, which is a humanized "HingeNotch" receptor variant with Notch1 extension (1788) and a Pax6 DNA-binding domain, which contains the following features, in N-terminus to C-terminus direction: antiCD19scFv-CD8Hinge2-Notch1(1758-1788)-Pax6DBD-p65(428-551). FIG. 14B depicts the activation profile of the receptor as determined by the same procedure described in FIG. 13B.

FIGS. 15A-15B schematically summarize the results from experiments performed to assess functionality of pRay255, yet another exemplary humanized "HingeNotch" receptor according to some embodiments of the disclosure. FIG. 15A depicts a schematic of the pRay255 receptor, which is a humanized "HingeNotch" receptor variant with a Pax6 DNA-binding domain, which contains the following features, in N-terminus to C-terminus direction: antiCD19scFv- CD8Hinge2-Notch1TMD-Notch2STS-Pax6DBD-p65(428-551). FIG. 15B depicts the activation profile of the receptor as determined by the same procedure described in FIG. 13B.

DETAILED DESCRIPTION OF THE DISCLOSURE

Figure 2:
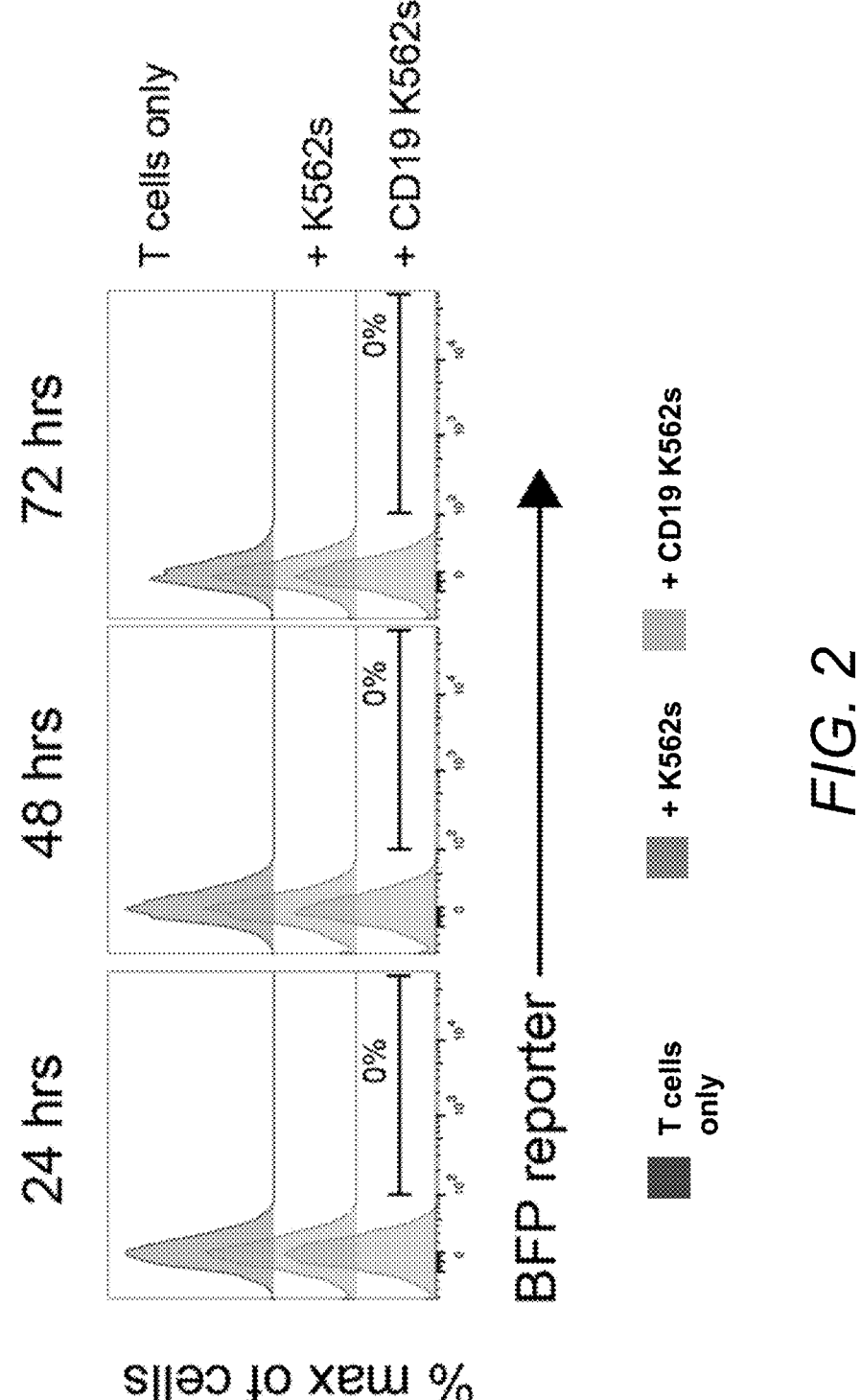
FIG. 2 schematically summarizes the results of experiments performed to evaluate the activation profile of primary human CD4+ T cells containing a (4×)HNF1α-response element reporter in the absence of a receptor to activate its transcription. In these experiments, activation over a 72-hr period of primary human CD4+ T cells containing the (4×)HNF1α-response element reporter. Approximately 1×10⁵ T cells were cultured alone (upper trace), with 1×10⁵ K562 cells (middle trace), or with 1×10⁵ CD19⁺ K562 cells (lower trace) for 24, 48 or 72 hours, and transcriptional activation of an inducible BFP reporter was measured using a Fortessa X-50 (BD). Percent cells activated by CD19⁺ K562s (lower trace % s) is indicated.
Figures 3A, 3B:
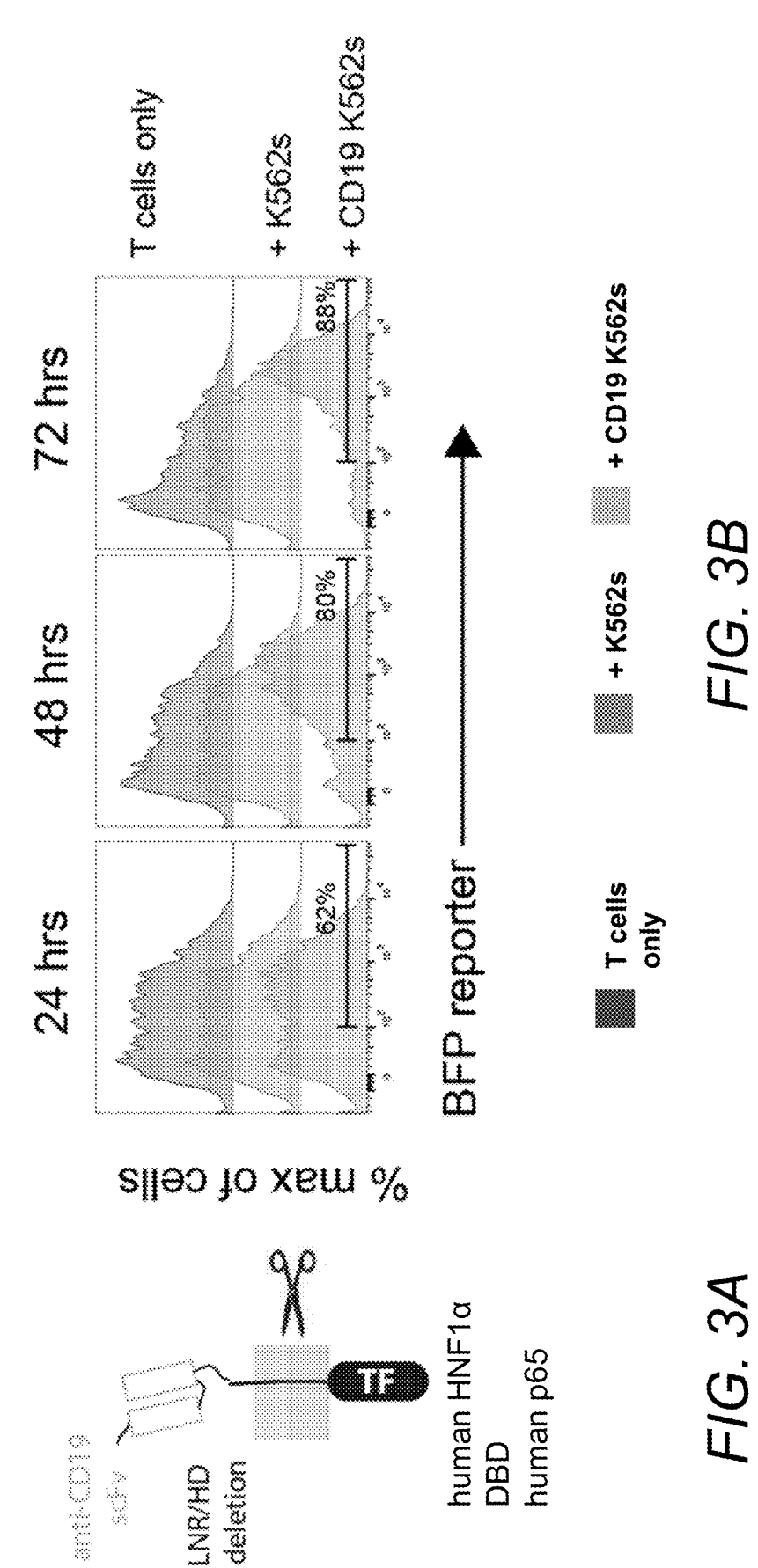
FIGS. 3A-3B schematically summarize the results from experiments performed to assess functionality of pRay239, which is an exemplary humanized "MiniNotch" receptor.
Figures 6A, 6B:
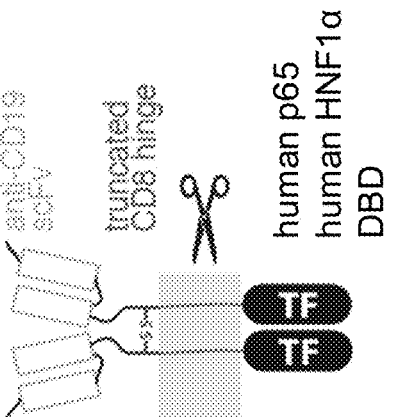
FIGS. 6A-6B schematically summarize the results from experiments performed to assess functionality of pRay242, an exemplary humanized "HingeNotch" receptor.
Figures 7A, 7B:
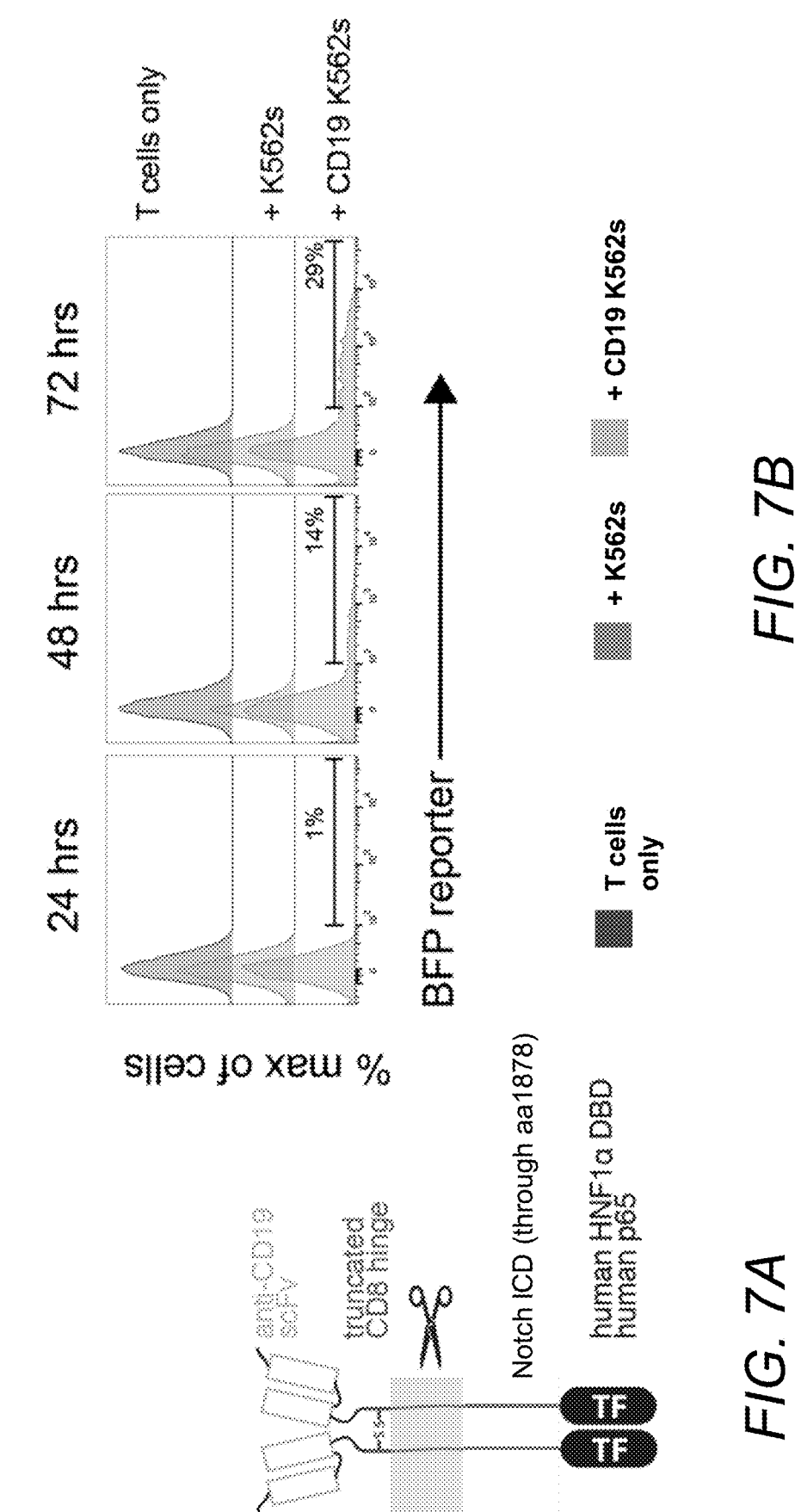
FIGS. 7A-7B schematically summarize the results from experiments performed to assess functionality of pRay243, another exemplary humanized "HingeNotch" receptor according to some embodiments of the disclosure.
Figures 8A, 8B:
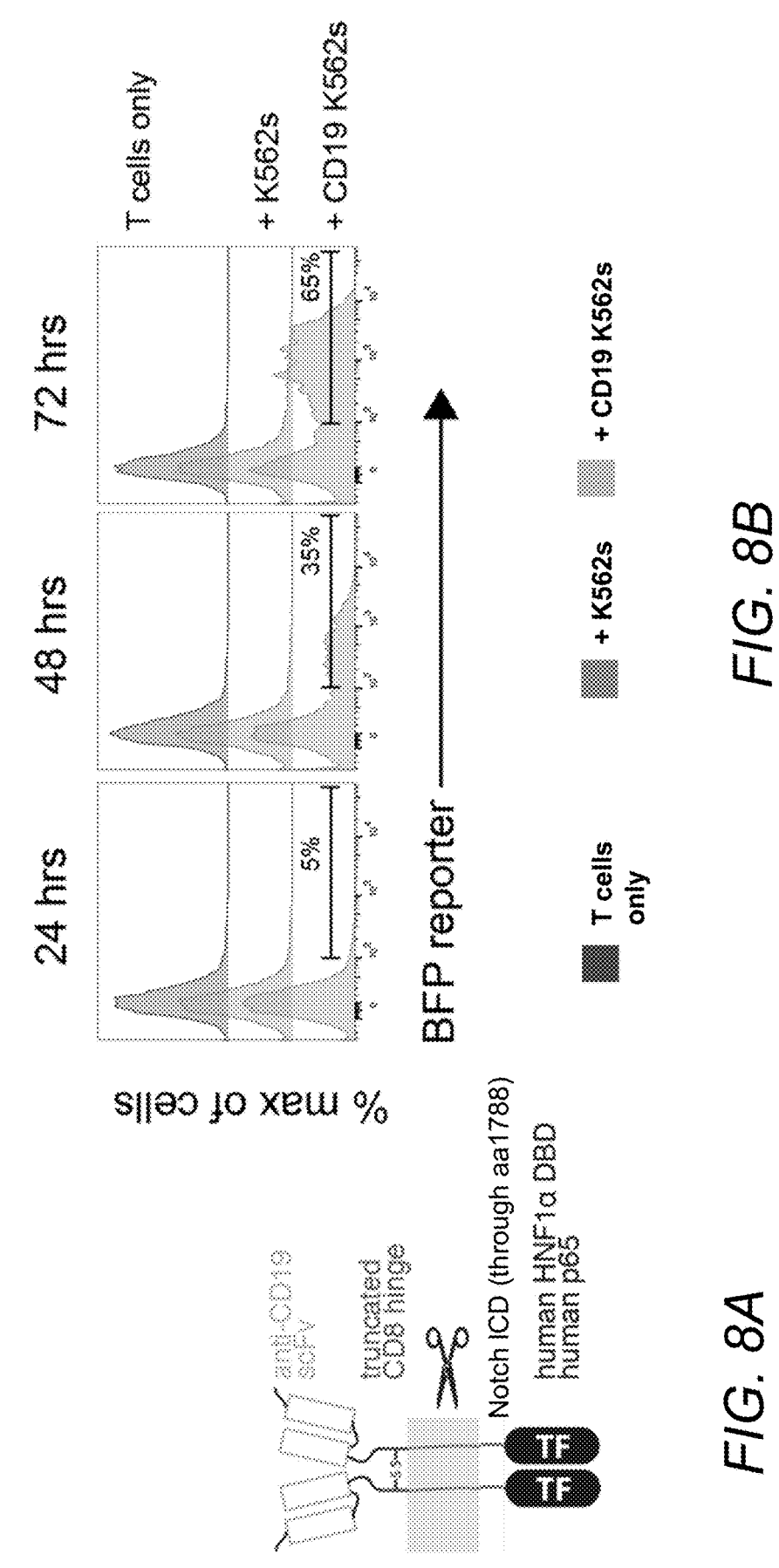
FIGS. 8A-8B schematically summarize the results from experiments performed to assess functionality of pRay244, another exemplary humanized "HingeNotch" receptor according to some embodiments of the disclosure.
Figures 9A, 9B:
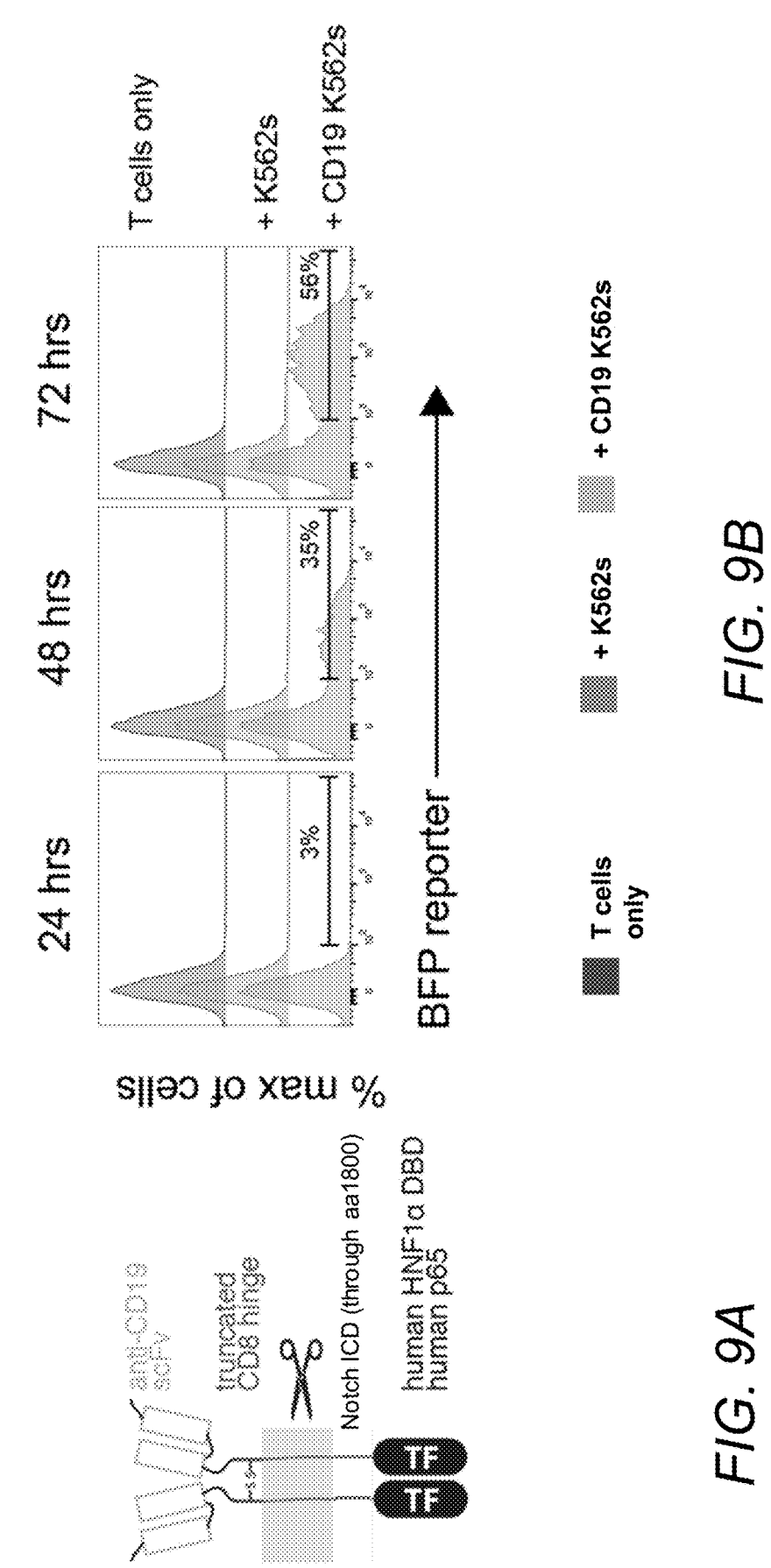
FIGS. 9A-9B schematically summarize the results from experiments performed to assess functionality of pRay250, another exemplary humanized "HingeNotch" receptor according to some embodiments of the disclosure.
Figures 10A, 10B:
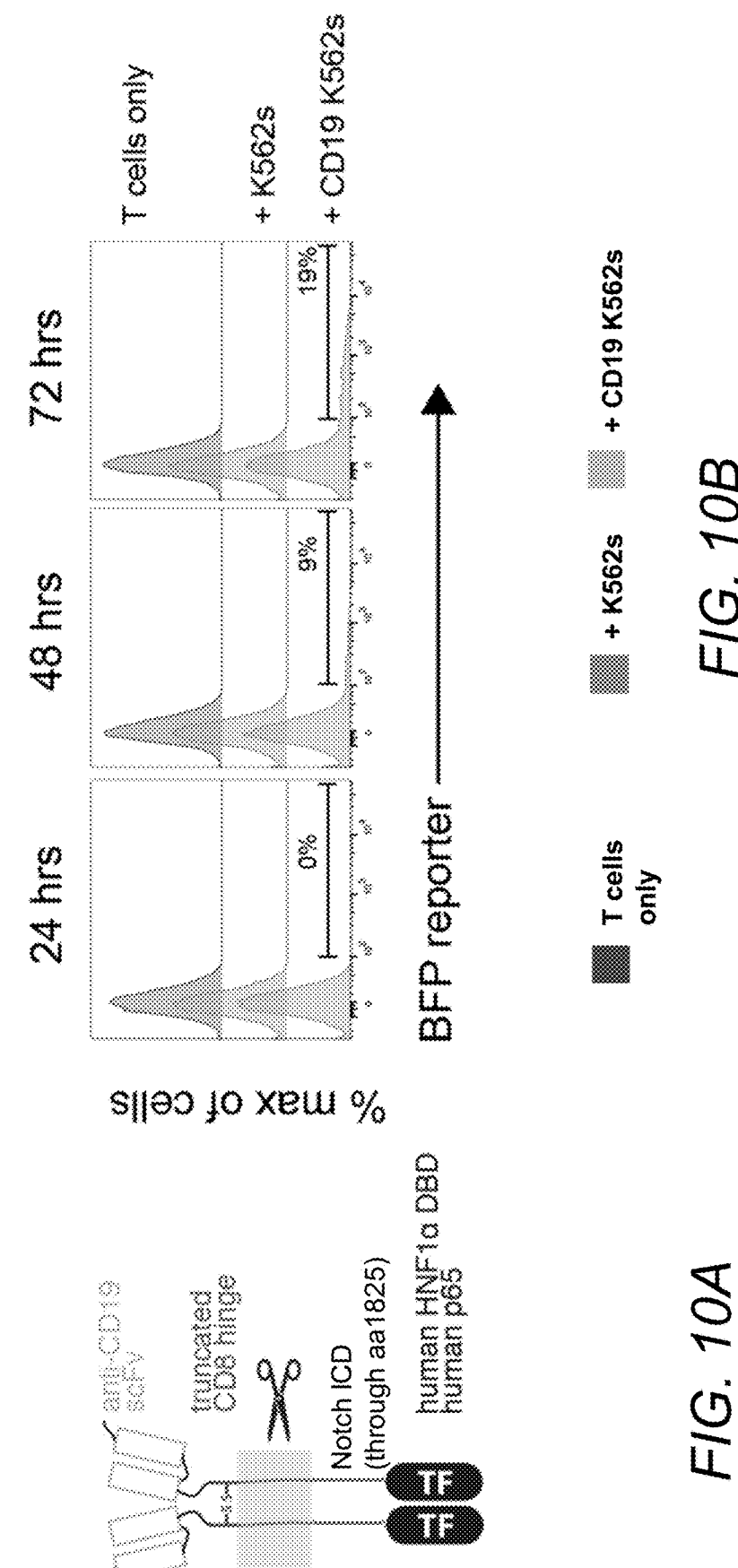
FIGS. 10A-10B schematically summarize the results from experiments performed to assess functionality of pRay251, another exemplary humanized "HingeNotch" receptor according to some embodiments of the disclosure.
Figures 11A, 11B:
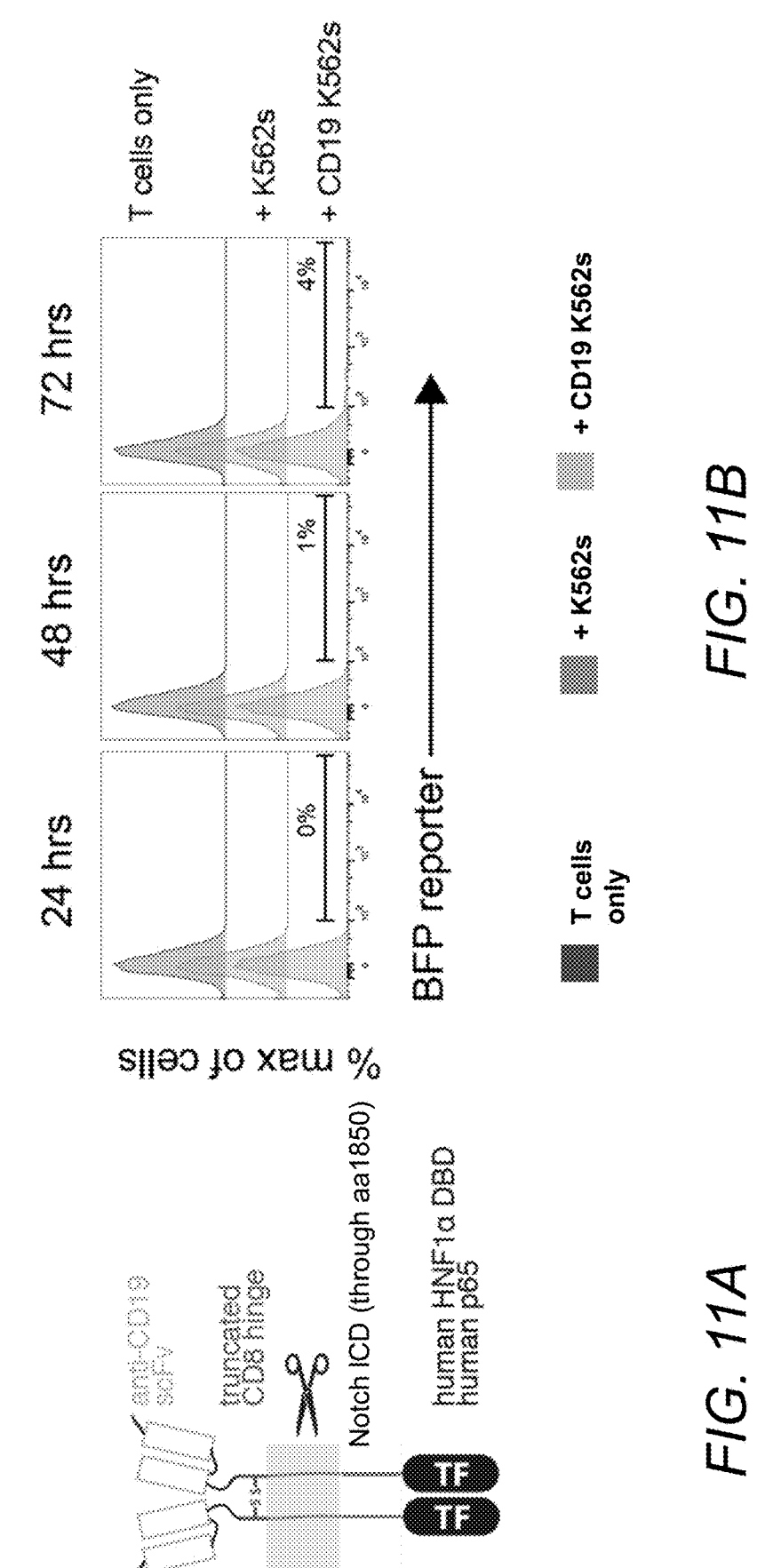
FIGS. 11A-11B schematically summarize the results from experiments performed to assess functionality of pRay252, another exemplary humanized "HingeNotch" receptor according to some embodiments of the disclosure.

The present disclosure generally relates to, among other things, a new class of chimeric oligomerizable Notch receptors containing a humanized transcriptional effector, engineered to modulate transcriptional regulation in a ligand-dependent manner. The activity of these fully humanized Notch receptors can be controlled by the presence of an extracellular ligand, allowing for spatial and temporal control of specific gene expression in mammalian cells, as well as for use in modulating cell activities or in treating various health conditions, such as diseases (e.g., cancers). Particularly, the new receptors (termed "humanized HingeNotch"), even though derived from Notch, do not require the Notch NEC subunit, particularly the NRR previously believed to be essential for the functioning of the receptors. This new class of receptors is synthetic and recombinant, and does not occur in nature. As described below, the chimeric Notch polypeptides disclosed herein can be synthetic polypeptides, and can be engineered, designed, or modified so as to provide desired and/or improved properties, e.g., modulating transcription. The demonstration that the new humanized HingeNotch receptors lacking the NRR herein are not only functional but demonstrate enhanced biologic activity is surprising and is contrary to the teachings in the field. In addition, the new chimeric receptors described herein incorporate an extracellular oligomerization domain to promote formation of oligomeric forms, e.g., dimeric or trimeric forms of the chimeric receptors. It is believed that this design facilitates oligomerization and/or clustering of the receptors, and improves ligand-dependent activation. In some embodiments, the receptors disclosed herein bind a target cell-surface ligand, which triggers proteolytic cleavage of the chimeric receptor and release of a transcriptional effector that modulates a custom transcriptional program in the cell. The disclosure also provides compositions and methods useful for producing such receptors, nucleic acids encoding same, cells genetically modified with the nucleic acids, as well as methods for modulating an activity of a cell and/or for the treatment of various diseases such as cancers. As described in Example 11-12 and FIGS. 16A-16B and 17 below, a number of humanized HingeNotch receptors of the disclosure can target cell killing and induce BCMA-CAR circuits. In particular, in vivo experiments shown in FIG. 16B demonstrate that a dual-vector circuit of fully humanized receptor described herein could effectively and specifically clear tumors in a dual-antigen model, thus offering a non-immunogenic solution for specific targeting of tumors. Furthermore, in vitro experiments shown in FIG. 17 demonstrate the Pax6-based receptors of the disclosure are small enough to fit into a single lentiviral vector configuration. Accordingly, without being bound to any particular theory, this single-vector design/formulation would allow such a circuit to enter current approved production pipelines for clinical applications, and also opens up the ability to utilize various delivery options such as targeted integration via CRISPR/Cas9 methods.

In the following detailed description, reference is made to the accompanying drawings, which form a part hereof. In the drawings, similar symbols generally identify similar components, unless context dictates otherwise. The illustrative alternatives described in the detailed description, drawings, and claims are not meant to be limiting. Other alternatives may be used and other changes may be made without departing from the spirit or scope of the subject matter presented here. It will be readily understood that the aspects, as generally described herein, and illustrated in the Figures, can be arranged, substituted, combined, and designed in a wide variety of different configurations, all of which are explicitly contemplated and make part of this application.

Definitions

The singular form "a", "an", and "the" include plural references unless the context clearly dictates otherwise. For example, the term "a cell" includes one or more cells, including mixtures thereof. "A and/or B" is used herein to include all of the following alternatives: "A", "B", "A or B", and "A and B."

The terms "administration" and "administering", as used herein, refer to the delivery of a composition or formulation as disclosed herein by an administration route including, but not limited to, intravenous, intra-arterial, intracranial, intra-muscular, intraperitoneal, subcutaneous, intramuscular, or combinations thereof. The term includes, but is not limited to, administration by a medical professional and self-administration.

"Cancer" refers to the presence of cells possessing several characteristics typical of cancer-causing cells, such as uncontrolled proliferation, immortality, metastatic potential, rapid growth and proliferation rate, and certain characteristic morphological features. Cancer cells can aggregate into a mass, such as a tumor, or can exist alone within a subject. A tumor can be a solid tumor, a soft tissue tumor, or a metastatic lesion. As used herein, the term "cancer" also encompasses other types of non-tumor cancers. Non-limiting examples include blood cancers or hematological cancers, such as leukemia. Cancer can include premalignant, as well as malignant cancers.

The term "human" when used in reference to a polynucleotide sequence or polypeptide sequence will be understood to encompass polynucleotide sequences or polypeptide sequences that are derived from a human source, e.g., (i) those isolated from a human, (ii) modified, designed and/or synthesized based on human polynucleotides or polypeptides, and are functionally and structurally related to the original human proteins. As such, the term "human derived gene/protein" will be understood to encompass not only the original gene/protein isolated from human cells but also a gene/protein obtained by modifying the human gene/protein, a gene/protein designed based on the original human gene/protein, and a gene/protein synthesized, in vitro or in vivo, based on the original human gene/protein. It should be understood that human nucleotide sequences and proteins encoded thereby often include some degree of variation across the entire spectrum of allelic sequences within the global populations. Accordingly, the term "human" when used in reference to a polynucleotide sequence or polypeptide sequence will be understood to encompass polynucleotide sequences or polypeptide sequences having about 95, 96, 97, 98, 99, 99.5, or about 100% identical to a human polynucleotide sequences or polypeptide sequence.

The term "humanized" as used herein when used in reference to a polynucleotide sequence or polypeptide sequence will be understood to encompass non-human sequences, e.g., polynucleotide sequences or polypeptide sequences having less than about 95% sequence identity to a human protein, which have been engineered or modified such that they are not immunogenic, or only minimally immunogenic, to an average human subject.

The terms "cell", "cell culture", and "cell line" refer not only to the particular subject cell or cell line but also to the progeny or potential progeny of such a cell, cell culture, or cell line, without regard to the number of transfers or passages in culture. It should be understood that not all progeny are exactly identical to the parental cell. This is because certain modifications may occur in succeeding generations due to either mutations (e.g., deliberate or inadvertent mutations) or environmental influences (e.g., methylation or other epigenetic modifications), such that progeny may not, in fact, be identical to the parent cell, but are still included within the scope of the term as used herein, so long as the progeny retain the same functionality as that of the original cell, cell culture, or cell line.

The term "modulating", in relation to the expression or activity of a polypeptide refers to a change in the expression or activity of the polypeptide. Modulation includes both activation (e.g., increase, induce, stimulate) and repression or inhibition (e.g., decrease, reduce, inhibit), or otherwise affecting the expression or activity of the polypeptide. The term may also refer to decreasing, reducing, inhibiting, increasing, inducing, activating, or otherwise affecting the activity of a gene encoding the polypeptide which can include, but is not limited to, modulating transcriptional activity.

The term "operably linked", as used herein, denotes a physical or functional linkage between two or more elements, e.g., polypeptide sequences or polynucleotide sequences, which permits them to operate in their intended fashion.

The term "percent identity", as used herein in the context of two or more nucleic acids or proteins, refers to two or more sequences or subsequences that are the same or have a specified percentage of nucleotides or amino acids that are the same (e.g., about 60% sequence identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the complement of a sequence. This definition also includes sequences that have deletions and/or additions, as well as those that have substitutions. Sequence identity can be calculated over a region that is at least about 20 amino acids or nucleotides in length, or over a region that is 10-100 amino acids or nucleotides in length, or over the entire length of a given sequence. Sequence identity can be calculated using published techniques and widely available computer programs, such as the GCS program package (Devereux et al, *Nucleic Acids Res.* 12:387, 1984), BLASTP, BLASTN, FASTA (Atschul et al., *J Mol Biol* 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

As used herein, and unless otherwise specified, a "therapeutically effective amount" or a "therapeutically effective number" of an agent is an amount or number sufficient to provide a therapeutic benefit in the treatment or management of a health condition, such as a disease (e.g., a cancer), or to delay or minimize one or more symptoms associated with the disease. A therapeutically effective amount or number of a compound means an amount or number of therapeutic agent, alone or in combination with other therapeutic agents, which provides a therapeutic benefit in the treatment or management of the disease. The term "therapeutically effective amount" can encompass an amount or number that improves overall therapy of the disease, reduces or avoids symptoms or causes of the disease, or enhances therapeutic efficacy of another therapeutic agent. An example of an "effective amount" is an amount sufficient to contribute to the treatment, prevention, or reduction of a symptom or symptoms of a disease, which could also be referred to as a "therapeutically effective amount." A "reduction" of a symptom means decreasing of the severity or frequency of the symptom(s), or elimination of the symptom(s). The exact amount of a composition including a "therapeutically effective amount" will depend on the purpose of the treatment, and will be ascertainable by one skilled in the art using known techniques (see, e.g., Lieberman, *Pharmaceutical Dosage Forms* (vols. 1-3, 2010); Lloyd, *The Art, Science and Technology of Pharmaceutical Compounding* (2016); Pickar, Dosage Calculations (2012); and *Remington: The Science and Practice of Pharmacy,* 22nd Edition, 2012, Gennaro, Ed., Lippincott, Williams & Wilkins).

As used herein, a "subject" or an "individual" includes animals, such as human (e.g., human subject) and non-human animals. In some embodiments, a "subject" or "individual" is a patient under the care of a physician. Thus, the subject can be a human patient or a subject who has, is at risk of having, or is suspected of having a disease of interest (e.g., cancer) and/or one or more symptoms of the disease. The subject can also be a subject who is diagnosed with a risk of the condition of interest at the time of diagnosis or later. The term "non-human animals" includes all vertebrates, e.g., mammals, e.g., rodents, e.g., mice, non-human primates, and other mammals, such as e.g., sheep, dogs, cows, chickens, and non-mammals, such as amphibians, reptiles, etc.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

All ranges disclosed herein also encompass any and all possible sub-ranges and combinations of sub-ranges thereof. Any listed range can be recognized as sufficiently describing and enabling the same range being broken down into at least equal halves, thirds, quarters, fifths, tenths, etc. As a non-limiting example, each range discussed herein can be readily broken down into a lower third, middle third and upper third, and so forth. As will also be understood by one skilled in the art all language such as "up to", "at least", "greater than", "less than", and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

Notch Receptors

Notch receptors are transmembrane proteins that mediate cell-cell contact signaling and play a central role in development and other aspects of cell-to-cell communication. Notch receptors have a modular domain organization. The Notch extracellular subunit (NEC) of wild type Notch receptors consist of a series of N-terminal epidermal growth factor (EGF)-like repeats that are responsible for ligand binding. O-linked glycosylation of these EGF repeats, including modification by O-fucose, Fringe, and Rumi glycosyltransferases, also modulates the activity of Notch receptors in response to different ligand subtypes in flies and mammals. The EGF repeats are followed by three LIN-12/Notch repeat (LNR) modules, which are unique to Notch receptors, and are widely reported to participate in preventing premature receptor activation. The heterodimerization (HD) domain of Notch1 is divided by furin cleavage during expression, so that its N-terminal part terminates the Notch extracellular subunit (NEC), and its C-terminal half constitutes the beginning of the Notch transmembrane (NTM) subunit. The N-terminal and C-terminal portions of the HD domain bind to each other, and hold the receptor together by non-covalent interactions. Following the extracellular HD-C region of the NEC is a transmembrane segment and an intracellular region (ICN), which includes a transcriptional activator.

Notch receptors mediate cell-cell contact signaling and play a central role in development and other aspects of cell-to-cell communication, e.g., communication between two contacting cells, in which one contacting cell is a "receiver" cell and the other contacting cell is a "sender" cell. Notch receptors expressed in a receiver cell recognize their ligands (e.g., the delta/serrate/lag, or "DSL" family of proteins), expressed on a sending cell. The engagement of notch and delta on these contacting cells leads to two-step proteolysis of the notch receptor that ultimately causes the release of the intracellular portion of the receptor from the membrane into the cytoplasm. Notch has a metalloprotease cleavage site (denoted "S2"), which is normally protected from cleavage by the Notch negative regulatory region (NRR), a domain consisting of three LNR modules and the HD of the NEC. It is believed that this two-step proteolysis is regulated by the force exerted by the sending cell: the DSL ligand pulls on the Notch receptor and changes the conformation of the negative regulatory region, exposing the metalloprotease site. That site is then cleaved by a constitutively active protease, releasing the extracellular binding portion and negative regulatory region (NRR) of the receptor. Release of the extracellular binding portion of the receptor in turn exposes another intramembrane cleavage site(s) (denoted "S3"), which is/are cleaved by γ-secretase within the cell membrane to release the nuclear homing intracellular domain from the cell membrane. W. R. Gordon et al., *Dev Cell* (2015) 33:729-36. This released domain alters receiver cell behavior by functioning as a transcriptional effector.

Notch receptors are involved in and are required for a variety of cellular functions during development and are important for the function of a vast number of cell-types across species. Evolutionary divergence of vertebrates and invertebrates has been accompanied by at least two rounds of gene duplication involving the Notch receptors: flies possess a single Notch gene, worms two (GLP-1 and LIN-12), and mammals four (NOTCH1-4). Transduction of Notch signals relies on three key events: (i) ligand recognition, (ii) conformational exposure of the ligand-dependent cleavage site, and (iii) assembly of nuclear transcriptional activation complexes.

Canonical Notch signals are transduced by a process called regulated intramembrane proteolysis. Notch receptors are normally maintained in a resting, proteolytically resistant conformation on the cell surface, but ligand binding initiates a proteolytic cascade that releases the intracellular portion of the receptor (also known as intracellular notch (ICN) or Notch intracellular domain (NICD)) from the membrane. The critical, regulated cleavage step is effected by ADAM metalloproteases and occurs at a site called S2 immediately external to the plasma membrane. This truncated receptor, dubbed NEXT (for Notch extracellular truncation), remains membrane tethered until it is processed at site S3 by γ-secretase, a multiprotein enzyme complex.

After γ-secretase-mediated cleavage, the ICN ultimately enters the nucleus, where it assembles a transcriptional activation complex that contains a DNA-binding transcription factor termed CSL (C-promoter-binding factor in mammals; also known as RBP-J)/Suppressor of hairless in *Drosophila melanogaster* or Lag1 in *Caenorhabditis elegans*), and a transcriptional coactivator of the Mastermind/Lag-3 family. This complex then engages additional coactivator proteins such as p300 to recruit the basal transcription machinery and activate the expression of downstream target genes.

Additional information regarding Notch receptors and Notch-mediated cell signaling can be found in, for example, W. R. Gordon et al., *Dev Cell* (2015) 33:729-36 and W. R. Gordon et al., *J. Cell Sci*. (2008) 121:3109-19, both of which are hereby incorporated by reference.

Compositions of the Disclosure

As described in greater detail below, one aspect of the present disclosure relates to a new class of chimeric Notch receptors that include a humanized transcriptional effector and are engineered to modulate transcriptional regulation in a ligand-dependent manner with various advantages over existing first-generation SynNotch receptors. For example, since natural Notch receptors are large with the NEC subunit containing several dozen tandem EGF-like repeats, by omitting the Notch negative regulatory regions, or even the entire NEC subunit, polynucleotides encoding the receptors of the disclosure can be made smaller than natural Notch receptors and existing SynNotch-encoding polynucleotides, which enables the use of vectors having more limited capacity, or the inclusion of additional elements that would otherwise be excluded by vector capacity-related size constraints.

In addition, the new receptors incorporate an extracellular oligomerization domain to promote formation of oligomeric forms, e.g., dimeric or trimeric forms of the chimeric receptors. Without being bound to any particular theory, this design facilitates oligomerization or clustering of the receptors to activate or increase ligand-dependent modulation of the response element. The combination of a fully humanized transcriptional effector and an extracellular oligomerization domain forms unique therapeutic Notch receptor systems that are artificial, scalable, and regulatable for the expression of desired genes and response elements, and have no or minimal immunogenicity, and therefore have a reduced risk of eliciting immunologic rejection of therapy. This is especially important because cell therapies are difficult and expensive to produce, and it is important for the engineered cells to have long-lived persistent activity in the patient. If the cell therapy is (or may be) eliminated quickly due to an immune response to non-human components of the receptors, further development of such therapies may cease due to unacceptable risk. The new class of humanized receptors disclosed herein is designed to mitigate this risk.

As described in the Examples, certain chimeric polypeptide receptors have been tested and validated in primary human T cells. These new receptors are expected to show similar performance in mouse models as well as models in other suitable animals or in vitro systems. The receptors disclosed herein may be engineered into various immune cell types for enhanced discrimination and elimination of tumors, or in engineered cells for control of autoimmunity and tissue regeneration. Accordingly, engineered cells, such as immune cells engineered to express one of more of the chimeric receptors disclosed herein, are also within the scope of the disclosure.

Chimeric Polypeptides

As outlined above, some embodiments of the present disclosure relate to novel, non-naturally occurring chimeric polypeptides engineered to modulate transcriptional regulation in a ligand-dependent manner. In particular, the new chimeric receptors, even though derived from Notch, do not require the Notch negative regulatory regions (NRRs) previously believed to be essential for the functioning of the receptors. Furthermore, the new engineered receptors described herein incorporate an extracellular oligomerization domain (e.g., hinge domain) to promote oligomerization to form higher order oligomeric, e.g., dimeric or trimeric, forms of the chimeric receptors. In some embodiments, the hinge domain includes polypeptide motifs capable of promoting oligomer formation of the chimeric polypeptide via intermolecular disulfide bonding. The extracellular oligomerization domain can replace part or all of the Notch extracellular domain. In some embodiments, the receptors disclosed herein bind a target cell-surface ligand, which triggers proteolytic cleavage of the receptors and release of a transcriptional effector that modulates a custom transcriptional program in the cell.

In some embodiments, provided herein is a chimeric polypeptide including, from N-terminus to C-terminus: (a) an ECD having a binding affinity for a selected ligand; (b) a hinge domain capable of promoting oligomer formation of the chimeric polypeptide via intermolecular disulfide bonding; (c) a TMD including one or more ligand-inducible proteolytic cleavage sites; and (d) an ICD including a human or humanized transcriptional effector, wherein binding of the selected ligand to the ECD induces cleavage at a ligand-inducible proteolytic cleavage site(s) between the transcriptional effector and the hinge domain, and wherein the chimeric polypeptide does not include a LIN-12-Notch repeat (LNR) and/or a heterodimerization domain (HD) of a Notch receptor.

Extracellular Domains (ECD)

As outlined above, the ECD of the chimeric polypeptide receptors (e.g., humanized HingeNotch receptors) in some embodiments of the disclosure has a binding affinity for one or more target ligands. The target ligand is expressed on a cell surface, or is otherwise anchored, immobilized, or restrained so that it can exert a mechanical force on the chimeric receptor. As such, without being bound to any particular theory, binding of the ECD of a chimeric receptor provided herein to a cell-surface ligand does not necessarily remove the target ligand from the target cell surface, but exerts a mechanical pulling force on the chimeric receptor. For example, an otherwise soluble ligand may be targeted if it is bound to a surface, or to a molecule in the extracellular matrix. In some embodiments, the target ligand is a cell-surface ligand. Non-limiting examples of suitable ligand types include cell surface receptors; adhesion proteins; carbohydrates, lipids, glycolipids, lipoproteins, and lipopolysaccharides that are surface-bound; integrins; mucins; and lectins. In some embodiments, the ligand is a protein. In some embodiments, the ligand is a carbohydrate.

In some embodiments, the ligand is a cluster of differentiation (CD) marker. In some embodiments, the CD marker is selected from the group consisting of CD1, CD1a, CD1b, CD1c, CD1d, CD1e, CD2, CD3d, CD3e, CD3g, CD4, CD5, CD7, CD8a, CD8b, CD19, CD20, CD21, CD22, CD23, CD25, CD27, CD28, CD33, CD34, CD40, CD45, CD48, CD52, CD59, CD66, CD70, CD71, CD72, CD73, CD79A, CD79B, CD80 (B7.1), CD86 (B7.2), CD94, CD95, CD134, CD140 (PDGFR4), CD152, CD154, CD158, CD178, CD181 (CXCR1), CD182 (CXCR2), CD183 (CXCR3), CD210, CD246, CD252, CD253, CD261, CD262, CD273 (PD-L2), CD274 (PD-L1), CD276 (B7H3), CD279, CD295, CD339 (JAG1), CD340 (HER2), EGFR, FGFR2, CEA, AFP, CA125, MUC-1, and MAGE.

In some embodiments, the extracellular domain includes the ligand-binding portion of a receptor. In some embodiments, the extracellular domain includes an antigen-binding moiety that binds to one or more target antigens. In some embodiments, the antigen-binding moiety includes one or more antigen-binding determinants of an antibody or a functional antigen-binding fragment thereof. One skilled in the art will readily understand that the term "functional fragment thereof" or "functional variant thereof" refers to a molecule having quantitative and/or qualitative biological activity in common with the wild-type molecule from which the fragment or variant was derived. For example, a functional fragment or a functional variant of an antibody is one which retains essentially the same ability to bind to the same epitope as the antibody from which the functional fragment or functional variant was derived. For instance, an antibody capable of binding to an epitope of a cell surface receptor may be truncated at the N-terminus and/or C-terminus, and the retention of its epitope binding activity assessed using assays known to those of skill in the art. In some embodiments, the antigen-binding moiety is selected from the group consisting of an antibody, a nanobody, a diabody, a triabody, or a minibody, an F(ab')2 fragment, an F(ab) fragment, a single chain variable fragment (scFv), and a single domain antibody (sdAb), or a functional fragment thereof. In some embodiments, the antigen-binding moiety includes an scFv.

The antigen-binding moiety can include naturally-occurring amino acid sequences or can be engineered, designed, or modified to provide desired and/or improved properties such as, e.g., binding affinity. Generally, the binding affinity of an antigen-binding moiety, e.g., an antibody, for a target antigen (e.g., CD19 antigen) can be calculated by the Scatchard method described by Frankel et al., *Mol. Immunol,* 16:101-06, 1979. In some embodiments, binding affinity is measured by an antigen/antibody dissociation rate. In some embodiments, binding affinity is measured by a competition radioimmunoassay. In some embodiments, binding affinity is measured by ELISA. In some embodiments, antibody affinity is measured by flow cytometry. An antibody that "selectively binds" an antigen (such as CD19) is an antigen-binding moiety that does not significantly bind other antigens but binds the target antigen with high affinity, e.g., with an equilibrium constant (KD) of 100 nM or less, such as 60 nM or less, for example, 30 nM or less, such as, 15 nM or less, or 10 nM or less, or 5 nM or less, or 1 nM or less, or 500 pM or less, or 400 pM or less, or 300 pM or less, or 200 pM or less, or 100 pM or less.

A skilled artisan can select an ECD based on the desired localization or function of a cell that is genetically modified to express a chimeric polypeptide (humanized HingeNotch receptor) of the present disclosure. For example, a chimeric polypeptide with an ECD including an antibody specific for a HER2 antigen can target cells to HER2-expressing breast cancer cells. In some embodiments, the ECD of the disclosed humanized HingeNotch receptors is capable of binding a tumor-associated antigen (TAA) or a tumor-specific antigen (TSA). A skill artisan will understand that TAAs include a molecule, such as e.g., protein, present on tumor cells and on normal cells, or on many normal cells, but at much lower concentration than on tumor cells. In contrast, TSAs generally include a molecule, such as e.g., protein which is present on tumor cells but absent from normal cells.

In some cases, the antigen-binding moiety is specific for an epitope present in an antigen that is expressed by a tumor cell, i.e., a tumor-associated antigen. The tumor-associated antigen can be an antigen associated with, e.g., a breast cancer cell, a B cell lymphoma, a pancreatic cancer, a Hodgkin lymphoma cell, an ovarian cancer cell, a prostate cancer cell, a mesothelioma, a lung cancer cell, a non-Hodgkin B-cell lymphoma (B-NHL) cell, an ovarian cancer cell, a prostate cancer cell, a mesothelioma cell, a melanoma cell, a chronic lymphocytic leukemia cell, an acute lymphocytic leukemia cell, a neuroblastoma cell, a glioma, a glioblastoma, a colorectal cancer cell, etc. It will also be understood that a tumor-associated antigen may also be expressed by a non-cancerous cell. In some embodiments, the antigen-binding domain is specific for an epitope present in a tissue-specific antigen. In some embodiments, the antigen-binding domain is specific for an epitope present in a disease-associated antigen.

Non-limiting examples of suitable target antigens include CD19, B7H3 (CD276), BCMA (CD269), alkaline phosphatase, placental-like 2 (ALPPL2), green fluorescent protein (GFP), enhanced green fluorescent protein (EGFP), signal regulatory protein $\alpha$ (SIRP$\alpha$), CD123, CD171, CD179$\alpha$, CD20, CD213A2, CD22, CD24, CD246, CD272, CD30, CD33, CD38, CD44v6, CD46, CD71, CD97, CEA, CLDN6, CLECL1, CS-1, EGFR, EGFRvIII, ELF2M, EpCAM, EphA2, Ephrin B2, FAP, FLT3, GD2, GD3, GM3, GPRCSD, HER2 (ERBB2/neu), IGLL1, IL-11R$\alpha$, KIT (CD 117), MUC1, NCAM, PAP, PDGFR-$\beta$, PRSS21, PSCA, PSMA, ROR1, SSEA-4, TAG72, TEM1/CD248, TEM7R, TSHR, VEGFR2, ALPI, citrullinated vimentin, cMet, and Axl.

In some embodiments, the target antigen is selected from CD19, B7H3 (CD276), BCMA (CD269), ALPPL2, CD123, CD171, CD179$\alpha$, CD20, CD213A2, CD22, CD24, CD246, CD272, CD30, CD33, CD38, CD44v6, CD46, CD71, CD97, CEA, CLDN6, CLECL1, CS-1, EGFR, EGFRvIII, ELF2M, EpCAM, EphA2, Ephrin B2, FAP, FLT3, GD2, GD3, GM3, GPRCSD, HER2 (ERBB2/neu), IGLL1, IL-11R$\alpha$, KIT (CD117), MUC1, NCAM, PAP, PDGFR-$\beta$, PRSS21, PSCA, PSMA, ROR1, SSEA-4, TAG72, TEM1/CD248, TEM7R, TSHR, VEGFR2, ALPI, citrullinated vimentin, cMet, Axl, GPC2, human epidermal growth factor receptor 2 (Her2/neu), CD276 (B7H3), IL-13R$\alpha$1, IL-13R$\alpha$2, $\alpha$-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD123, CD93, CD99, CD117, chromogranin, cytokeratin, desmin, glial fibrillary acidic protein (GFAP), gross cystic disease fluid protein (GCDFP-15), ALK, DLK1, FAP, NY-ESO, WT1, HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysin, thyroglobulin, thyroid transcription factor-1, AOC3 (VAP-1), CAM-3001, CCL11 (eotaxin-1), CD125, CD147 (basigin), CD154 (CD40L), CD2, CD20, CD23 (IgE receptor), CD25 (a subunit of the heterodimeric IL-2 receptor), CD3, CD4, CD5, IFN-α, IFN-γ, IgE, IgE Fc region, IL-1, IL-12, IL-23, IL-13, IL-17, IL-17A, IL-22, IL-4, IL-5, IL-5, IL-6, IL-6 receptor, integrin α4, integrin α4β7, LFA-1 (CD11α), myostatin, OX-40, scleroscin, SOST, TGFβ1, TNF-α, VEGF-A, pyruvate kinase isoenzyme type M2 (tumor M2-PK), CD20, CD5, CD7, CD3, TRBC1, TRBC2, BCMA, CD38, CD123, CD93, CD34, CD1α, SLAMF7/CS1, FLT3, CD33, CD123, TALLA-1, CSPG4, DLL3, Kappa light chain, Lamba light chain, CD16/FcγRIII, CD64, FITC, CD22, CD27, CD30, CD70, GD2 (ganglioside G2), GD3, EGFRvIII (epidermal growth factor variant III), EGFR and isovariants thereof, TEM-8, sperm protein 17 (Sp17), mesothelin. Further non-limiting examples of suitable antigens include PAP (prostatic acid phosphatase), prostate stem cell antigen (PSCA), prostein, NKG2D, TARP (T cell receptor gamma alternate reading frame protein), Trp-p8, STEAP1 (six-transmembrane epithelial antigen of the prostate 1), an abnormal ras protein, an abnormal p53 protein, integrin β3 (CD61), galactin, K-Ras (V-Ki-ras2 Kirsten rat sarcoma viral oncogene), Ral-B, GPC2, CD276 (B7H3), or IL-13Rα. In some embodiments, the antigen is Her2. In some embodiments, the antigen is ALPPL2. In some embodiments, the antigen is BCMA. In some embodiments, the antigen-binding moiety of the ECD is specific for a reporter protein, such as GFP and eGFP. Non-limiting examples of such antigen-binding moiety include a LaG17 anti-GFP nanobody. In some embodiments, the antigen-binding moiety of the ECD includes an anti-BCMA fully-humanized VH domain (FHVH). In some embodiments, the antigen is signal regulatory protein α (SIRPα).

Additional antigens suitable for targeting by the chimeric polypeptide receptors disclosed herein include, but are not limited to GPC2, human epidermal growth factor receptor 2 (Her2/neu), CD276 (B7H3), IL-13Rα1, IL-13Rα2, α-fetoprotein (AFP), carcinoembryonic antigen (CEA), cancer antigen-125 (CA-125), CA19-9, calretinin, MUC-1, epithelial membrane protein (EMA), epithelial tumor antigen (ETA). Other suitable target antigens include, but are not limited to, tyrosinase, melanoma-associated antigen (MAGE), CD34, CD45, CD123, CD93, CD99, CD117, chromogranin, cytokeratin, desmin, glial fibrillary acidic protein (GFAP), gross cystic disease fluid protein (GCDFP-15), ALK, DLK1, FAP, NY-ESO, WT1, HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysin, thyroglobulin, thyroid transcription factor-1.

Additional antigens suitable for targeting by the chimeric receptors disclosed herein include, but are not limited to, those associated with an inflammatory disease such as, AOC3 (VAP-1), CAM-3001, CCL11 (eotaxin-1), CD125, CD147 (basigin), CD154 (CD40L), CD2, CD20, CD23 (IgE receptor), CD25 (a subunit of the heteromeric of IL-2 receptor), CD3, CD4, CD5, IFN-α, IFN-γ, IgE, IgE Fc region, IL-1, IL-12, IL-23, IL-13, IL-17, IL-17A, IL-22, IL-4, IL-5, IL-5, IL-6, IL-6 receptor, integrin α4, integrin α4β7, LFA-1 (CD11α), myostatin, OX-40, scleroscin, SOST, TGFβ1, TNF-α, and VEGF-A.

Further antigens suitable for targeting by the chimeric polypeptides disclosed herein include, but are not limited to the pyruvate kinase isoenzyme type M2 (tumor M2-PK), CD20, CD5, CD7, CD3, TRBC1, TRBC2, BCMA, CD38, CD123, CD93, CD34, CD1α, SLAMF7/CS1, FLT3, CD33, CD123, TALLA-1, CSPG4, DLL3, Kappa light chain, Lamba light chain, CD16/FcγRIII, CD64, FITC, CD22, CD27, CD30, CD70, GD2 (ganglioside G2), GD3, EGFRvIII (epidermal growth factor variant III), EGFR and isovariants thereof, TEM-8, sperm protein 17 (Sp17), mesothelin. Further non-limiting examples of suitable antigens include PAP (prostatic acid phosphatase), prostate stem cell antigen (PSCA), prostein, NKG2D, TARP (T cell receptor gamma alternate reading frame protein), Trp-p8, STEAP1 (six-transmembrane epithelial antigen of the prostate 1), an abnormal ras protein, an abnormal p53 protein, integrin β3 (CD61), galactin, K-Ras (V-Ki-ras2 Kirsten rat sarcoma viral oncogene), and Ral-B. In some embodiments, the antigen is GPC2, CD19, Her2/neu, CD276 (B7H3), IL-13Rα1, or IL-13Rα2.

In some embodiments, the antigen is Her2. In some embodiments, the antigen is ALPPL2. In some embodiments, the antigen is BCMA. In some embodiments, the antigen-binding moiety of the ECD is specific for a reporter protein, such as GFP and eGFP. Non-limiting examples of such antigen-binding moiety include a LaG17 anti-GFP nanobody. In some embodiments, the antigen-binding moiety of the ECD includes an anti-BCMA fully-humanized VH domain (FHVH).

In some embodiments, antigens suitable for targeting by the chimeric polypeptides disclosed herein include ligands derived from a pathogen. For example, the antigen can be HER2 produced by HER2-positive breast cancer cells. In some embodiments, the antigen can be CD19 that is expressed on B-cell leukemia. In some embodiments, the antigen can be EGFR that is expressed on glioblastoma multiform (GBM) but much less expressed so on healthy CNS tissue. In some embodiments, the antigen can be CEA that is associated with cancer in adults, for example colon cancer.

In some embodiments, the antigen-binding moiety of the ECD is specific for a cell surface target, where non-limiting examples of cell surface targets include CD19, CD30, Her2, CD22, ENPP3, EGFR, CD20, CD52, CD11α, and α-integrin. In some embodiments, the chimeric polypeptides disclosed herein include an extracellular domain having an antigen-binding moiety that binds CD19, BCMA, CEA, HER2, MUC1, CD20, ALPPL2, BCMA, or EGFR. In some embodiments, the chimeric polypeptides provided herein (e.g., humanized HingeNotch receptors) include an extracellular domain including an antigen-binding moiety that binds CD19. In some embodiments, the chimeric polypeptides provided herein (e.g., Hinge-Notch receptors) include an extracellular domain including an antigen-binding moiety that binds ALPPL2. In some embodiments, the chimeric polypeptides provided herein (e.g., Hinge-Notch receptors) include an extracellular domain including an antigen-binding moiety that binds BCMA. In some embodiments, the chimeric polypeptides provided herein (e.g., Hinge-Notch receptors) include an extracellular domain including an antigen-binding moiety that binds Her2.

In some embodiments, the chimeric polypeptides disclosed herein (e.g., humanized HingeNotch receptors) include an extracellular domain including an antigen-binding moiety that binds CD19, ALPPL2, BCMA, or Her2. In some embodiments, the antigen-binding moiety includes an amino acid sequence having at least 70%, at least 75%, at least 80%, at least 85%, at least 90%, at least 95%, at least 96%, at least 97%, at least 98%, at least 99% sequence identity to SEQ ID NO: 13 in the Sequence Listing. In some embodiments, the antigen-binding moiety includes an amino acid sequence having at least 90% sequence identity to SEQ ID NO: 13. In some embodiments, the antigen-binding moiety includes an amino acid sequence having at least 95% sequence identity to SEQ ID NO: 13. In some embodiments, the antigen-binding moiety includes an amino acid sequence having 100% sequence identity to SEQ ID NO: 13. In some embodiments, the antigen-binding moiety includes an amino acid sequence having the sequence of SEQ ID NO: 13, wherein one, two, three, four, or five of the amino acid residues in SEQ ID NO: 13 is substituted by a different amino acid residue.

Hinge Domain

As outlined above, the Notch extracellular domains located N-terminally to the TMD of the chimeric polypeptide of the disclosure include an oligomerization domain (e.g., hinge domain) containing one or more polypeptide motifs that promote oligomer formation of the chimeric polypeptides via intermolecular disulfide bonding. In these instances, within the chimeric Notch receptors disclosed herein, the hinge domain generally includes a flexible oligo- or polypeptide connector region between the ECD and the TMD. Thus, the hinge domain provides flexibility between the ECD and TMD and also provides sites for intermolecular disulfide bonding between two or more chimeric polypeptide monomers to form an oligomeric complex. In some embodiments, the hinge domain includes motifs that promote dimer formation of the chimeric polypeptides disclosed herein. In some embodiments, the hinge domain includes motifs that promote trimer formation of the chimeric polypeptides disclosed herein (e.g., a hinge domain derived from OX40).

Hinge polypeptide sequences suitable for the compositions and methods of the disclosure can be naturally-occurring hinge polypeptide sequences (e.g., those from naturally-occurring immunoglobulins). Alternatively, a hinge polypeptide sequence can be a synthetic sequence that corresponds to a naturally-occurring hinge polypeptide sequence, or can be an entirely synthetic hinge sequence, or can be engineered, designed, or modified to provide desired and/or improved properties, e.g., modulating transcription. Suitable hinge polypeptide sequences include, but are not limited to, those derived from IgA, IgD, and IgG subclasses, such as IgG1 hinge domain, IgG2 hinge domain, IgG3 hinge domain, and IgG4 hinge domain, or a functional variant thereof. In some embodiments, the hinge polypeptide sequence contains one or more CXXC motifs. In some embodiments, the hinge polypeptide sequence contains one or more CPPC motifs. Additional information in this regard can be found in, for example, a recent review by Vidarsson G. et al., *Frontiers Immunol*. Oct. 20, 2014, which is hereby incorporated by reference in its entirety.

Accordingly, in some embodiments, the hinge domain includes a hinge polypeptide sequence derived from an IgG1 hinge domain or a functional variant thereof. In some embodiments, the hinge domain includes a hinge polypeptide sequence derived from an IgG2 hinge domain or a functional variant thereof. In some embodiments, the hinge domain includes a hinge polypeptide sequence derived from an IgG3 hinge domain or a functional variant thereof. In some embodiments, the hinge domain includes a hinge polypeptide sequence derived from an IgG4 hinge domain or a functional variant thereof. In some embodiments, the hinge domain includes a hinge polypeptide sequence derived from an IgA hinge domain or a functional variant thereof. In some embodiments, the hinge domain includes a hinge polypeptide sequence derived from an IgD hinge domain or a functional variant thereof.

Additional hinge polypeptide sequences suitable for the compositions and methods disclosed herein include, but are not limited to, hinge polypeptide sequences derived from a CD8α hinge domain, a CD28 hinge domain, a CD152 hinge domain, a PD-1 hinge domain, a CTLA4 hinge domain, an OX40 hinge domain, an FcγRIIIα hinge domain, and functional variants thereof. In some embodiments, the hinge domain includes a hinge polypeptide sequence derived from a CD8α hinge domain or a functional variant thereof. In some embodiments, the hinge domain includes a hinge polypeptide sequence derived from a CD28 hinge domain or a functional variant thereof. In some embodiments, the hinge domain includes a hinge polypeptide sequence derived from an OX40 hinge domain or a functional variant thereof. In some embodiments, the hinge domain includes a hinge polypeptide sequence derived from an IgG4 hinge domain or a functional variant thereof.

The length and/or amino acid composition of the hinge domain are selected to confer flexibility and the capacity for oligomerization. One skilled in the art will readily appreciate that the length and amino acid composition of the hinge polypeptide sequence can be optimized to vary the orientation and/or proximity of the ECD and the TMD relative to one another, as well as of the chimeric polypeptide monomers to one another, to achieve a desired activity of the chimeric polypeptide of the disclosure. In some embodiments, a single-chain peptide including about one to 100 amino acid residues (e.g., 2, 3, 4, 5, 6, 7, 8, 9, 10, 11, 12, 13, 14, 15, 16, 17, 18, 19, 20, etc. amino acid residues) can be used as a hinge domain. In some embodiments, the hinge domain includes about 5 to 50, about 10 to 60, about 20 to 70, about 30 to 80, about 40 to 90, about 50 to 100, about 60 to 80, about 70 to 100, about 30 to 60, about 20 to 80, about 30 to 90 amino acid residues. In some embodiments, the hinge domain includes about 1 to 10, about 5 to 15, about 10 to 20, about 15 to 25, about 20 to 40, about 30 to 50, about 40 to 60, about 50 to 70 amino acid residues. In some embodiments, the hinge domain includes about 40 to 70, about 50 to 80, about 60 to 80, about 70 to 90, or about 80 to 100 amino acid residues. In some embodiments, the hinge domain includes about 1 to 10, about 5 to 15, about 10 to 20, about 15 to 25 amino acid residues. In some embodiments, the hinge domain includes a sequence having at least 80% sequence identity, such as, at least 80%, at least 85%, at least 90%, at least 95%, at least 96%, at least 97%, at least 98%, or 99% sequence identity to a sequence selected from the group consisting of SEQ ID NOS: 15-19 in the Sequence Listing. In some embodiments, the hinge domain includes an amino acid sequence having at least 90% sequence identity to a sequence selected from the group consisting of SEQ ID NOS: 15-19. In some embodiments, the hinge domain includes an amino acid sequence having at least 95% sequence identity to a sequence selected from the group consisting of SEQ ID NOS: 15-19. In some embodiments, the hinge domain includes an amino acid sequence having about 100% sequence identity to a sequence selected from the group consisting of SEQ ID NOS: 15-19. In some embodiments, the hinge domain includes an amino acid sequence having a sequence selected from the group consisting of SEQ ID NOS: 15-19, wherein one, two, three, four, or five of the amino acid residues in any one of the SEQ ID NOS: 15-19 is substituted by a different amino acid residue.

In some embodiments, the hinge domain includes a sequence having at least 80% sequence identity, such as, at least 80%, at least 85%, at least 90%, at least 95%, at least 96%, at least 97%, at least 98%, or 99% sequence identity to SEQ ID NO: 15 in the Sequence Listing. In some embodiments, the hinge domain includes an amino acid sequence having at least 90% sequence identity to SEQ ID NO: 15. In some embodiments, the hinge domain includes an amino acid sequence having at least 95% sequence identity to SEQ ID NO: 15. In some embodiments, the hinge domain includes an amino acid sequence having about 100% sequence identity to SEQ ID NO: 15. In some embodiments, the hinge domain includes an amino acid sequence having the sequence of SEQ ID NO: 15, wherein one, two, three, four, or five of the amino acid residues in SEQ ID NO: 15 is substituted by a different amino acid residue.

Transmembrane Domain (TMD)

As outlined above, the chimeric polypeptides of the disclosure include a transmembrane domain including one or more ligand-inducible proteolytic cleavage sites.

Examples of proteolytic cleavage sites in a Notch receptor (e.g., S2 or S3) are as described above. Additional proteolytic cleavage sites suitable for the compositions and methods disclosed herein include, but are not limited to, a metalloproteinase cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). For example, the cleavage sequence of MMP-9 is Pro-X-X-Hy (wherein, X represents an arbitrary residue; Hy, a hydrophobic residue such as Leu, Ile, Val, Phe, Trp, Tyr, Val, Met, and Pro), e.g., Pro-X-X-Hy-(Ser/Thr), e.g., Pro-Leu/Gln-Gly-Met-Thr-Ser (SEQ ID NO: 76) or Pro-Leu/Gln-Gly-Met-Thr (SEQ ID NO: 77). Another example of a suitable protease cleavage site is a plasminogen activator cleavage site, e.g., a urokinase-type plasminogen activator (uPA) or a tissue plasminogen activator (tPA) cleavage site. Another example of a suitable protease cleavage site is a prolactin cleavage site. Specific examples of cleavage sequences of uPA and tPA include sequences comprising Val-Gly-Arg. Another exemplary protease cleavage site that can be included in a proteolytically cleavable linker is a tobacco etch virus (TEV) protease cleavage site, e.g., Glu-Asn-Leu-Tyr-Thr-Gln-Ser (SEQ ID NO: 78), where the protease cleaves between the glutamine and the serine. Another example of a protease cleavage site that can be included in a proteolytically cleavable linker is an enterokinase cleavage site, e.g., Asp-Asp-Asp-Asp-Lys (SEQ ID NO: 79), where cleavage occurs after the lysine residue. Another example of a protease cleavage site that can be included in a proteolytically cleavable linker is a thrombin cleavage site, e.g., Leu-Val-Pro-Arg (SEQ ID NO: 80). Additional suitable linkers comprising protease cleavage sites include sequences cleavable by the following proteases: a PreScission™ protease (a fusion protein comprising human rhinovirus 3C protease and glutathione-S-transferase), a thrombin, cathepsin B, Epstein-Barr virus protease, MMP-3 (stromelysin), MMP-7 (matrilysin), MMP-9; thermolysin-like MMP, matrix metalloproteinase 2 (MMP-2), cathepsin L; cathepsin D, matrix metalloproteinase 1 (MMP-1), urokinase-type plasminogen activator (uPA), membrane type 1 matrix metalloproteinase (MT-MMP), stromelysin 3 (or MMP-11), thermolysin, fibroblast collagenase and stromelysin-1, matrix metalloproteinase 13 (collagenase-3), tissue-type plasminogen activator (tPA), human prostate-specific antigen, kallikrein (hK3), neutrophil elastase, and calpain (calcium activated neutral protease). Proteases that are not native to the host cell in which the receptor is expressed (for example, TEV) can be used as a further regulatory mechanism, in which activation of the humanized HingeNotch is not possible until the protease is expressed or otherwise provided. Additionally, a protease may be tumor-associated or disease-associated (expressed to a significantly higher degree than in normal tissue), and serve as an independent regulatory mechanism. For example, some matrix metalloproteases are highly expressed in certain cancer types.

Generally, the TMD suitable for the chimeric polypeptides and Hinge-Notch receptors disclosed herein can be any transmembrane domain of a Type 1 transmembrane receptor including at least one γ-secretase cleavage site. Detailed description of the structure and function of the γ-secretase complex as well as its substrate proteins, including amyloid precursor protein (APP) and Notch, can, for example, be found in a recent review by Zhang et al., *Frontiers Cell Neurosci* (2014). Non-limiting suitable TMDs from Type 1 transmembrane receptors include those from CLSTN1, CLSTN2, APLP1, APLP2, LRP8, APP, BTC, TGBR3, SPN, CD44, CSF1R, CXCL16, CX3CL1, DCC, DLL1, DSG2, DAG1, CDH1, EPCAM, EPHA4, EPHB2, EFNB1, EFNB2, ErbB4, GHR, HLA-A, and IFNAR2, wherein the TMD includes at least one γ-secretase cleavage site. Additional TMDs suitable for the compositions and methods described herein include, but are not limited to, transmembrane domains from Type 1 transmembrane receptors IL1R1, IL1R2, IL6R, INSR, ERN1, ERN2, JAG2, KCNE1, KCNE2, KCNE3, KCNE4, KL, CHL1, PTPRF, SCN1B, SCN3B, NPR3, NGFR, PLXDC2, PAM, AGER, ROBO1, SORCS3, SORCS1, SORL1, SDC1, SDC2, SPN, TYR, TYRP1, DCT, VASN, FLT1, CDH5, PKHD1, NECTIN1, PCDHGC3, NRG1, LRP1B, CDH2, NRG2, PTPRK, SCN2B, Nradd, and PTPRM. In some embodiments, the TMD of the chimeric polypeptides or Notch receptors of the present disclosure is a TMD derived from the TMD of a member of the calsyntenin family, such as, alcadein alpha and alcadein gamma.

In some embodiments, the TMD for the chimeric polypeptides disclosed herein is one of the transmembrane domains known for Notch receptors. In some embodiments, the TMD of the chimeric polypeptides or Notch receptors of the disclosure is a TMD derived from a different Notch receptor. For example, in a humanized HingeNotch receptor based on human Notch1, the Notch1 TMD can be substituted with a Notch3 TMD, or a Notch TMD from a non-human animal such as *Danio rerio, Drosophila melanogaster, Xenopus laevis*, or *Gallus gallus*.

In some embodiments, the transmembrane domain includes an amino acid sequence exhibiting at least 70%, at least 75%, at least 80%, at least 85%, at least 90%, at least 95%, at least 96%, at least 97%, at least 98%, at least 99% sequence identity to one or more of SEQ ID NOS: 21-30 in the Sequence Listing. In some embodiments, the transmembrane domain includes an amino acid sequence having at least 90% sequence identity to a sequence selected from the group consisting of SEQ ID NOS: 21-30. In some embodiments, the transmembrane domain includes an amino acid sequence having at least 95% sequence identity to a sequence selected from the group consisting of SEQ ID NOS: 21-30. In some embodiments, the transmembrane domain includes an amino acid sequence having about 100% sequence identity to one or more of SEQ ID NOS: 21-30. In some embodiments, the transmembrane domain includes an amino acid sequence having a sequence selected from the group consisting of SEQ ID NOS: 21-30, wherein one, two, three, four, or five of the amino acid residues in any one of the SEQ ID NOS: 21-30 is substituted by a different amino acid residue.

In some embodiments, the transmembrane domain includes an amino acid sequence exhibiting at least 70%, at least 75%, at least 80%, at least 85%, at least 90%, at least 95%, at least 96%, at least 97%, at least 98%, at least 99% sequence identity to SEQ ID NO: 21 in the Sequence Listing. In some embodiments, the transmembrane domain includes an amino acid sequence having at least 90% sequence identity to SEQ ID NO: 21. In some embodiments, the transmembrane domain includes an amino acid sequence having at least 95% sequence identity to SEQ ID NO: 21. In some embodiments, the transmembrane domain includes an amino acid sequence having about 100% sequence identity to SEQ ID NO: 21. In some embodiments, the transmembrane domain includes an amino acid sequence having the sequence of SEQ ID NO: 21, wherein one, two, three, four, or five of the amino acid residues in SEQ ID NOS: 21-30 is substituted by a different amino acid residue.

In some embodiments, the amino acid substitution(s) within the TMD includes one or more substitutions within a "GV" motif of the TMD. In some embodiments, at least one of such substitution(s) is a substitution to alanine. For example, one, two, three, four, five, or more of the amino acid residues of the sequence FMYVAAAAFVLL-FFVGCGVLLS (SEQ ID NO: 21), may be substituted by a different amino acid residue. In some embodiments, the amino acid residue at position 18 and/or 19 of the "GV" motif within SEQ ID NO: 17 is substituted by a different amino acid residue. In some embodiments, the glycine residue at position 18 of SEQ ID NO: 21 is substituted by a different amino acid residue. In some embodiments, the valine residue at position 19 of SEQ ID NO: 21 is substituted by a different amino acid residue. In some embodiments, the transmembrane domain includes an amino acid sequence having a sequence corresponding to SEQ ID NO: 21 with a mutation at the position corresponding to position 18 of SEQ ID NO: 21, such as G18A mutations. In some embodiments, the transmembrane domain includes an amino acid sequence having a sequence corresponding to SEQ ID NO: 17 with a mutation at the position corresponding to position 19 of SEQ ID NO: 21, such as V19A mutations.

Stop-Transfer-Sequence (STS)

In some embodiments, the chimeric polypeptides of the disclosure include a stop-transfer-sequence (STS) which constitutes a highly-charged domain located C-terminally to the TMD. Without being bound to any particular theory, such a highly-charged domain between the TMD and the ICD prevents the ICD from entering the membrane. The STS is linked to the TMD and the ICD in the following order, from N-terminus to C-terminus, TMD-STS-ICD. The length and/or amino acid composition of the STS can be selected to achieve the desired receptor sensitivity. In some embodiments, the STS includes about 4 to about 40 amino acid residues (e.g., 4, 5, 6, 7, 8, 9, 10, 11, 12, 13, 14, 15, 16, 17, 18, 19, or 20, etc. amino acid residues). In some embodiments, the STS includes about 4 to 15, about 6 to 20, about 8 to 25, about 10 to 30, about 12 to 35, about 14 to 40, about 5 to 40, about 10 to 35, about 15 to 30, about 20 to 25, about 20 to 40, about 10 to 30, about 4 to 20, or about 5 to 25 amino acid residues. In some embodiments, the STS includes about 4 to 10, about 5 to 12, about 6 to 14, about 7 to 18, about 8 to 20, about 9 to 22, about 10 to 24, or about 11 to 26 amino acid residues. In some embodiments, the STS includes about 4 to 10 residues, such as, 4, 5, 6, 7, 8, 9, or 10 amino acid residues. In some embodiments, the STS includes a sequence having at least 80% sequence identity, such as, at least 80%, at least 85%, at least 90%, at least 95%, at least 96%, at least 97%, at least 98%, or 99% sequence identity to a sequence selected from the group consisting of SEQ ID NOS: 31-51 in the Sequence Listing. In some embodiments, the STS includes an amino acid sequence having at least 90% sequence identity to a sequence selected from the group consisting of SEQ ID NOS: 31-51. In some embodiments, the STS includes an amino acid sequence having at least 95% sequence identity to a sequence selected from the group consisting of SEQ ID NOS: 31-51. In some embodiments, the STS includes an amino acid sequence having about 100% sequence identity to a sequence selected from the group consisting of SEQ ID NOS: 31-51. In some embodiments, the STS includes an amino acid sequence having a sequence selected from the group consisting of SEQ ID NOS: 31-51, wherein one, two, three, four, or five of the amino acid residues in any one of the SEQ ID NOS: 31-51 is substituted by a different amino acid residue.

In some embodiments, the STS includes a sequence having at least 70%, 80% sequence identity, such as, at least 70%, at least 75%, at least 80%, at least 85%, at least 90%, at least 95%, at least 96%, at least 97%, at least 98%, or 99% sequence identity to a STS sequence from Notch1, Notch2, Notch3, Notch4, CLSTN1, CLSTN2, CSF1R, CXCL16, DAG1, GHR, PTPRF, AGER, KL, NRG1, LRP1B, Jag2, EPCAM, KCNE3, CDH2, NRG2, PTPRK, BTC, EPHA3, IL1R2, or PTPRM. In some embodiments, the STS includes a sequence comprising only Lys (K) or Arg (R) in the first four amino acid residues. In some embodiments, the STS includes one, two, three, four, five, or more basic residues. In some embodiments, the STS includes five, four, three, two, one, or zero aromatic residues or residues with hydrophobic and/or bulky side chains.

In some embodiments, the STS includes a sequence having at least 80% sequence identity, such as, at least 80%, at least 85%, at least 90%, at least 95%, at least 96%, at least 97%, at least 98%, or 99% sequence identity to a sequence selected from the group consisting of SEQ ID NOS: 31-36 in the Sequence Listing. In some embodiments, the STS includes an amino acid sequence having at least 90% sequence identity to a sequence selected from the group consisting of SEQ ID NOS: 31-36. In some embodiments, the STS includes an amino acid sequence having at least 95% sequence identity to a sequence selected from the group consisting of SEQ ID NOS: 31-36. In some embodiments, the STS includes an amino acid sequence having about 100% sequence identity to a sequence selected from the group consisting of SEQ ID NOS: 31-36. In some embodiments, the STS includes an amino acid sequence having a sequence selected from the group consisting of SEQ ID NOS: 31-36, wherein one, two, three, four, or five of the amino acid residues in any one of the SEQ ID NOS: 31-36 is substituted by a different amino acid residue. In some embodiments, the STS includes a sequence having at least 70% sequence identity, such as, at least 70%, at least 75%, at least 80%, at least 85%, at least 90%, at least 95%, at least 96%, at least 97%, at least 98%, or 99% sequence identity to a STS sequence from Notch1, Notch2, Notch3, Notch4, CLSTN1, CLSTN2, JAG2, PTPRF, LRP1B, NRG2, KCNE2, KCNE3, KCNE4, AGER, PKHD1, GHR, PTPRM, DAG1, NRG1, EPCAM, KL, PTPRK, CXCL16, or any one listed in Tables 3 and 4. In some embodiments, the STS includes a sequence comprising only Lys (K) or Arg (R) in the first four amino acid residues. In some embodiments, the STS includes one, two, three, four, five, or more basic residues. In some embodiments, the STS comprises five, four, three, two, one, or zero aromatic residues or residues with hydrophobic and/or bulky side chains.

Intracellular Domain (ICD)

As outlined above, the chimeric polypeptides of the disclosure include a transcriptional effector. The transcriptional effector of the disclosure is a polypeptide element that acts to activate or inhibit the transcription of a promoter-driven DNA sequence. Transcriptional effectors suitable for the compositions and methods of the disclosure can be naturally-occurring transcriptional effectors or can be engineered, designed, or modified so as to provide desired and/or improved properties, e.g., modulating transcription. In some embodiments, the transcriptional effector is a human transcriptional effector. In some embodiments, the transcriptional effector is a humanized transcriptional effector.

As discussed above, the engineered Notch receptors of the present disclosure are advantageous in that they can provide the ability to trigger a custom transcriptional program in engineered cells. In some embodiments, transcriptional effector of the disclosure is a custom transcriptional effector that drives transcription off a specific sequence that only appears once in the engineered cell.

In some embodiments, the chimeric polypeptides of the disclosure a transcriptional effector comprising a DNA-binding domain (DBD) operably linked to another domain through which the transcriptional effector exerts it effect (effector domain). As described in further detail below, exemplary effector domains suitable for the engineered Notch receptors of the disclosure include, but are not limited to, transcriptional activating domains, transcriptional repressor domains, epigenetic effector domains, and DNA modifying enzymes.

Exemplary types of suitable DBDs for the humanized HingeNotch receptors disclosed herein include, but are not limited to homeodomains, leucine zipper domains, HMG-box domains, forkhead/winged helix domains, basic Helix-Loop-Helix (bHLH) domains, Helix-Turn-Helix (HTH) domains, T-box domains, and zinc finger domains.

In some embodiments, the DBD used in the transcriptional effector are derived from human transcription factors. For example, transcription factors from which DBDs can be obtained include human homeodomain-containing polypeptides, such as, for example, Oct-3/4, Cdx-2, Gbx2, Gsh1, HesX1, HoxAI O, HoxA1, and HoxB1. Additional human homeodomain-containing polypeptides from which suitable DBDs can be obtained include Irx2, Isl1, Meisl, Meox2, Nanog, Nkx2.2, Onecut, Otx1, Oxt2, Pax5, Pax6, Pdx1, Tcf1, Tcf2, and Zfhx1.

In some embodiments, DBDs used in the transcriptional effector disclosed herein are derived from human zinc finger domain-containing polypeptides, such as, for example, Klf-4, Atbfl, Esrrb, Gcnf, Jarid2, Jmjdl a, Jmjd2c, Klf-3, Klf-5, Mel-18, Myst3, and Nad. Additional human zinc finger domain-containing polypeptides from which suitable DBDs can be obtained include REST, Rex-1, Rybp, Sall4, SalM, Tif1, YY1, Zeb2, Zfp281, Zfp57, Zic3, Coup-Tf1, Coup-Tf2, Bmi1, Rnf2, Mta1, Pias1, Pias2, Pias3, and Piasy.

In some embodiments, DBDs incorporated into the transcriptional effector of the humanized HingeNotch receptors disclosed herein are derived from human HMG-box domain containing polypeptides, such as, for example, Sox-2, Sox-6, Sox-9, Sox-10, Sox-15, Lef1, Tcf-7, Tcf7l1. Human bHLH domain-containing proteins from which suitable DBDs can be obtained include, but are not limited to c-Myc, L-Myc, N-Myc, Hand1, Mad1, Mad3, Mad4, Mxi1, Myf5, Neurog2, Ngn3, Olig2, Tcf3, and f4. Non-limiting examples of fork-head/winged helix domain polypeptides from which suitable DBDs can be obtained include Foxd and Foxd3.

In some embodiments, DBDs incorporated into the transcriptional effector of the humanized HingeNotch receptors disclosed herein are derived from (i) HTH domain containing polypeptides, such as BAF155 and the like; (ii) leucine zipper domain containing polypeptides such as, for example, C/EBPβ and mafa; (iii) T-box domain containing polypeptides such as, for example, Eomes and Tbx-3; (vi) RFX domain containing polypeptides such as Rfx4 and the like; and (v) STAT domain containing polypeptides such as Stat3 and the like.

In some embodiments, DBDs incorporated into the transcriptional effector of the humanized HingeNotch receptors disclosed herein can be derived from a human hepatocyte nuclear factor 1 homeobox A (HNF1α) protein, a human hepatocyte nuclear factor 1 homeobox B (HNF1β) protein, a human paired box protein (Pax-6), a human paired box protein (Pax-1) protein, a human paired box protein (Pax-2) protein, a human paired box protein (Pax-3) protein, a human paired box protein (Pax-4), or a human paired box protein (Pax-7).

In some embodiments, the DNA-binding domain is derived from a human hepatocyte nuclear factor 1 homeobox A (HNF1α) protein. In some embodiments, the HNF1α DNA-binding domain includes the amino acid sequence of SEQ ID NO: 52 or a functional variant thereof In some embodiments, the DNA-binding domain is derived from a human paired box protein, Pax6. In some embodiments, the Pax6 DNA-binding domain includes the amino acid sequence of SEQ ID NO: 53 or a functional variant thereof.

As outlined above, the transcriptional effector of the humanized HingeNotch receptors disclosed herein includes a second domain through which the transcriptional effector exerts its effect (effector domain). In some embodiments, the transcriptional effector directly regulates differentiation of the cell. It will be understood by one having ordinary skill in the art that a transcriptional effector can be a transcriptional activator or a transcriptional repressor. Exemplary effector domains suitable for the engineered Notch receptors of the disclosure include, but are not limited to, transcriptional activating domains, transcriptional repressor domains, epigenetic effector domains, and DNA modifying enzymes. In some embodiments, the transcriptional effector is a transcriptional repressor. In some embodiments, the transcriptional effector is a transcriptional activator. In some embodiments, the transcriptional effector directly regulates differentiation of the cell. In some embodiments, the transcriptional effector indirectly modulates (e.g., regulates) differentiation of the cell by modulating the expression of a second transcription factor.

Accordingly, in some embodiments, the effector domain of the transcriptional effector includes a transcription-activating domain. Non-limiting examples of transcription-activating domains suitable for use in the compositions and methods disclosed herein include a p65 activation domain of NFκB; and a histone acetyltransferase core domain of the human E1A-associated protein p300 (p300 HAT core activation domain). In some embodiments, the effector domain of the transcriptional effector includes a p65 activation domain of NFκB.

In some embodiments, the effector domain of the transcriptional effector includes a human or humanized transcription repressor domain. Non-limiting examples of transcription repressor domains suitable for use in the compositions and methods disclosed herein include a Kruppel associated box repression domain (KRAB); a Repressor Element Silencing Transcription Factor repression domain (REST); a WRPW motif of the hairy-related basic helix-loop-helix repressor proteins repression domain (WRPW); a DNA (cytosine-5)-methyltransferase 3B repression domain (DNMT3B); and an HP1 alpha chromoshadow repression domain. In some embodiments, the transcription repressor domain includes a KRAB repressor domain.

In some embodiments, the effector domain of the transcriptional effector includes a human or humanized epigenetic effector domain. Examples of epigenetic effector domain suitable for use in the compositions and methods disclosed herein include, but are not limited to, DNA methyltransferases DNMT (DNMT1, DNMT3), HAT1, GCN5, PCAF, MLL, SET, DOT1, SUV39H, G9a, KAT2A/B, EZH1/2, TET1/2, SIRT family protein effector domains, histone deacetylases, LSD1, and KDM family protein effector domains.

Effectors domains suitable for the compositions and methods of the disclosure can be naturally-occurring transcriptional effectors or can be engineered, designed, or modified so as to provide desired and/or improved properties, e.g., modulating transcription a eukaryotic cell. In some embodiments, the effector domain is derived from an animal protein. In some embodiments, the effector domain is derived from a mammalian protein. In some embodiments, the effector domain is derived from non-human primate protein. In some embodiments, the effector domain is derived from a human protein.

In some embodiments, the DBD of the transcriptional effector is N-terminally linked to its effector domain.

In some embodiments, the ICD of the chimeric receptors disclosed herein further includes a nuclear localization signal sequence (NLS). NLSs are short peptide motifs that mediate the nuclear importation of proteins by binding to their receptors, known as importins (karyopherins).

Chimeric polypeptides and humanized HingeNotch receptors of the present disclosure can be chimeric polypeptides of any length, including chimeric polypeptides that are generally between about 100 amino acids (aa) to about 1000 aa, e.g., from about 100 aa to about 200 aa, from about 150 aa to about 250 aa, from about 200 aa to about 300 aa, from about 250 aa to about 350 aa, from about 300 aa to about 400 aa, from about 350 aa to about 450 aa, from about 400 aa to about 500 aa in length. In some embodiments, the disclosed chimeric polypeptides are at least about 100, 200, 300, 400, 500, 600, 700, 750, 800, 850, 900, 950, or 1,000 aa in length. In some embodiments, the disclosed chimeric polypeptides are less than about 1,500, 1,400, 1,300, 1,200, 1,100, 1,000, 950, 900, 850, 800, 750, 700, 600, 500, 400, 350, 300, 250, or 200 aa in length. In some embodiments, the disclosed chimeric polypeptides are generally between about 400 aa to about 450 aa, from about 450 aa to about 500 aa, from about 500 aa to about 550 aa, from about 550 aa to about 600 aa, from about 600 aa to about 650 aa, from about 650 aa to about 700 aa, from about 700 aa to about 750 aa, from about 750 aa to about 800 aa, from about 800 aa to about 850 aa, from about 850 aa to about 900 aa, from about 900 aa to about 950 aa, or from about 950 aa to about 1000 aa in length. In some cases, the chimeric polypeptides of the present disclosure have a length of about 300 aa to about 400 aa. In some cases, the chimeric polypeptides of the present disclosure have a length of about 300 aa to about 350 aa. In some cases, the chimeric polypeptides of the present disclosure have a length of about 300 aa to about 325 aa. In some cases, the chimeric polypeptides of the present disclosure have a length of about 350 aa to about 400 aa. In some cases, the chimeric polypeptides of the present disclosure have a length of 591 aa to 920 aa.

In some embodiments, the chimeric polypeptides of the present disclosure include an amino acid sequence of a length shorter than 500, shorter than 600, shorter than 700, shorter than 800, or shorter than 900 amino acid residues. In some embodiments, the chimeric polypeptide includes an amino acid sequence is of a length shorter than 600 amino acid residues. In some embodiments, the chimeric polypeptides of the present disclosure include an amino acid sequence of a length shorter than 600 amino acid residues. In some embodiments, the chimeric polypeptides of the present disclosure include an amino acid sequence of a length shorter than 500 amino acid residues.

Additional Domains

In some embodiments, the Notch extracellular domains located N-terminally to the TMD can further include additional domains, for example a membrane localization signal such as a CD8α signal, a detectable marker such as a myc tag or his tag, and the like. Without being bound to any particular theory, it may be beneficial to incorporate additional domains N-terminally to the hinge domain. It is also contemplated that the chimeric polypeptides as described herein can be further engineered to include one or more additional features such as a signal sequence, a detectable label, a tumor-specific cleavage site, a disease-specific cleavage site, or combinations thereof. For example, several proteases (such as matrix metalloproteases) are upregulated in cancers, allowing tumor-specific cleavage specificity not via a specific cleavage site but via higher levels of specific proteases. Additional information in this regard can be found in, for example, J. S. Dudani et al., *Annu Rev Cancer Biol* (2018), 2:353-76, which is incorporated herein by reference.

In some embodiments, the chimeric polypeptide of the disclosure includes: (a) a hinge domain including an amino acid sequence having at least 80% sequence identity to any one of SEQ ID NO: 15-19; (b) a transmembrane domain including an amino acid sequence having at least 80% sequence identity to SEQ ID NO: 21-30; and (c) a stop-transfer-sequence domain including an amino acid sequence having at least 80% sequence identity to any one of SEQ ID NOS: 31-51. In some embodiments, the chimeric polypeptide of the disclosure includes: (a) a hinge domain including an amino acid sequence having at least 90% sequence identity to any one of SEQ ID NO: 15-19; (b) a transmembrane domain including an amino acid sequence having at least 90% sequence identity to SEQ ID NO: 21-30; and (c) a stop-transfer-sequence domain including an amino acid sequence having at least 90% sequence identity to any one of SEQ ID NOS: 31-51. In some embodiments, the chimeric polypeptide of the disclosure includes: (a) a hinge domain including an amino acid sequence having at least 95% sequence identity to any one of SEQ ID NO: 15-19; (b) a transmembrane domain including an amino acid sequence having at least 95% sequence identity to SEQ ID NO: 21-30; and (c) a stop-transfer-sequence domain including an amino acid sequence having at least 95% sequence identity to any one of SEQ ID NOS: 31-51.

In some embodiments, the chimeric polypeptide of the disclosure includes an amino acid sequence having at least about 80%, 90%, 95%, 96%, 97%, 98%, 99%, or 100% sequence identity to a chimeric receptor disclosed herein. In some embodiments, provided herein are chimeric polypeptides including an amino acid sequence having at least about 80%, 90%, 95%, 96%, 97%, 98%, 99%, or 100% sequence identity to any one of SEQ ID NOS: 2, 4-12, and 65-66 identified in the Sequence Listing. In some embodiments, the chimeric polypeptides include an amino acid sequence having at least about 80%, 90%, 95%, 96%, 97%, 98%, 99%, or 100% sequence identity to any one of SEQ ID NO: 2. In some embodiments, the chimeric polypeptides include an amino acid sequence having at least about 80%, 90%, 95%, 96%, 97%, 98%, 99%, or 100% sequence identity to any one of SEQ ID NO: 2. In some embodiments, the chimeric polypeptides include an amino acid sequence having at least about 80%, 90%, 95%, 96%, 97%, 98%, 99%, or 100% sequence identity to any one of SEQ ID NO: 4. In some embodiments, the chimeric polypeptides include an amino acid sequence having at least about 80%, 90%, 95%, 96%, 97%, 98%, 99%, or 100% sequence identity to any one of SEQ ID NO: 5. In some embodiments, the chimeric polypeptides include an amino acid sequence having at least about 80%, 90%, 95%, 96%, 97%, 98%, 99%, or 100% sequence identity to any one of SEQ ID NO: 6. In some embodiments, the chimeric polypeptides include an amino acid sequence having at least about 80%, 90%, 95%, 96%, 97%, 98%, 99%, or 100% sequence identity to any one of SEQ ID NO: 7. In some embodiments, the chimeric polypeptides include an amino acid sequence having at least about 80%, 90%, 95%, 96%, 97%, 98%, 99%, or 100% sequence identity to any one of SEQ ID NO: 8. In some embodiments, the chimeric polypeptides include an amino acid sequence having at least about 80%, 90%, 95%, 96%, 97%, 98%, 99%, or 100% sequence identity to any one of SEQ ID NO: 9. In some embodiments, the chimeric polypeptides include an amino acid sequence having at least about 80%, 90%, 95%, 96%, 97%, 98%, 99%, or 100% sequence identity to any one of SEQ ID NO: 10. In some embodiments, the chimeric polypeptides include an amino acid sequence having at least about 80%, 90%, 95%, 96%, 97%, 98%, 99%, or 100% sequence identity to SEQ ID NO: 11. In some embodiments, the chimeric polypeptides include an amino acid sequence having at least about 80%, 90%, 95%, 96%, 97%, 98%, 99%, or 100% sequence identity to SEQ ID NO: 12. In some embodiments, the chimeric polypeptides include an amino acid sequence having at least about 80%, 90%, 95%, 96%, 97%, 98%, 99%, or 100% sequence identity to SEQ ID NO: 65. In some embodiments, the chimeric polypeptides include an amino acid sequence having at least about 80%, 90%, 95%, 96%, 97%, 98%, 99%, or 100% sequence identity to SEQ ID NO: 66.

In some embodiments, the following domains are derived from human polypeptides: (a) the extracellular ligand-binding domain, (b) the hinge domain, (c) the TMD, and (d) the ICD. In some embodiments, the following domains are substantially non-immunogenic in a human subject: (a) the extracellular ligand-binding domain, (b) the hinge domain, (c) the TMD, and (d) the ICD. In some embodiments, the ICD is substantially non-immunogenic in a human subject. Methods and systems suitable for determine immunogenicity of a protein in human cells are known in the art. For example, immunogenicity can be predicted in vitro by incubating cells with the protein and monitoring surface expression of receptors on antigen-presenting cells, T cell proliferation, or cytokine release. Identification of T cell epitopes in silico may also be useful for predicting antigenicity of novel polypeptide sequences.

Nucleic Acid Molecules

In another aspect, provided herein are various nucleic acid molecules including nucleotide sequences encoding the chimeric polypeptides of the disclosure. In some embodiments, expression cassettes and expression vectors contain these nucleic acid molecules operably linked to heterologous nucleic acid sequences such as, for example, regulatory sequences which allow in vivo expression of the receptor in a host cell.

Nucleic acid molecules of the present disclosure can be of any length, including for example, between about 1.5 Kb and about 50 Kb, between about 5 Kb and about 40 Kb, between about 5 Kb and about 30 Kb, between about 5 Kb and about 20 Kb, or between about 10 Kb and about 50 Kb, for example between about 15 Kb to 30 Kb, between about 20 Kb and about 50 Kb, between about 20 Kb and about 40 Kb, about 5 Kb and about 25 Kb, or about 30 Kb and about 50 Kb.

In some embodiments, provided herein is a nucleic acid molecule including a nucleotide sequence encoding a chimeric polypeptide including, from N-terminus to C-terminus: (a) an extracellular ligand-binding domain having a binding affinity for a selected ligand; (b) a hinge domain capable of promoting oligomer formation of the chimeric polypeptide via intermolecular disulfide bonding; (c) a transmembrane domain including one or more ligand-inducible proteolytic cleavage sites; and (d) an intracellular domain including a human or humanized transcriptional effector, wherein binding of the selected ligand to the extracellular ligand-binding domain induces cleavage at a ligand-inducible proteolytic cleavage site between the transcriptional effector and the hinge domain, and wherein the chimeric polypeptide does not include a LIN-12-Notch repeat (LNR) and/or a heterodimerization domain (HD) of a Notch receptor.

In some embodiments, the nucleotide sequence is incorporated into an expression cassette or an expression vector. It will be understood that an expression cassette generally includes a construct of genetic material that contains coding sequences and enough regulatory information to direct proper transcription and/or translation of the coding sequences in a recipient cell, in vivo and/or ex vivo. Generally, the expression cassette may be inserted into a vector for targeting to a desired host cell and/or into a subject. As such, in some embodiments, an expression cassette of the disclosure include a coding sequence for the chimeric polypeptide as disclosed herein, which is operably linked to expression control elements, such as a promoter, and optionally, any or a combination of other nucleic acid sequences that affect the transcription or translation of the coding sequence.

In some embodiments, the nucleotide sequence is incorporated into a cloning vector or an expression vector. It will be understood by one skilled in the art that the term "vector" generally refers to a recombinant polynucleotide construct designed for transfer between host cells, and that may be used for the purpose of transformation, e.g., the introduction of heterologous DNA into a host cell. As such, in some embodiments, the vector can be a replicon, such as a plasmid, phage, or cosmid, into which another DNA segment may be inserted so as to bring about the replication of the inserted segment. In some embodiments, the expression vector can be an integrating vector. In some embodiments, the nucleotide sequence is incorporated into a cloning vector.

In some embodiments, the expression vector can be a viral vector. As will be appreciated by one of skill in the art, the term "viral vector" is widely used to refer either to a nucleic acid molecule (e.g., a transfer plasmid) that includes virus-derived nucleic acid elements that generally facilitate transfer of the nucleic acid molecule or integration into the genome of a cell or to a viral particle that mediates nucleic acid transfer. Viral particles will generally include various viral components and sometimes also host cell components in addition to nucleic acid(s). The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, including LTRs that are primarily derived from a lentivirus, which is a genus of retrovirus.

In some embodiments, provided herein are nucleic acid molecules encoding a polypeptide with an amino acid sequence having at least about 80%, 90%, 95%, 96%, 97%, 98%, 99%, or 100% sequence identity to a chimeric receptor disclosed herein. In some embodiments, provided herein are nucleic acid molecules encoding a polypeptide with an amino acid sequence having at least about 80%, 90%, 95%, 96%, 97%, 98%, 99%, or 100% sequence identity to any one of SEQ ID NOS: 2, 4-12, and 65-66 as identified in the Sequence Listing. In some embodiments, the nucleic acid molecules encode a polypeptide with an amino acid sequence having at least about 80%, 90%, 95%, 96%, 97%, 98%, 99%, or 100% sequence identity to SEQ ID NO: 2. In some embodiments, the nucleic acid molecules encode a polypeptide with an amino acid sequence having at least about 80%, 90%, 95%, 96%, 97%, 98%, 99%, or 100% sequence identity to SEQ ID NO: 4. In some embodiments, the nucleic acid molecules encode a polypeptide with an amino acid sequence having at least about 80%, 90%, 95%, 96%, 97%, 98%, 99%, or 100% sequence identity to SEQ ID NO: 5. In some embodiments, the nucleic acid molecules encode a polypeptide with an amino acid sequence having at least about 80%, 90%, 95%, 96%, 97%, 98%, 99%, or 100% sequence identity to SEQ ID NO: 6. In some embodiments, the nucleic acid molecules encode a polypeptide with an amino acid sequence having at least about 80%, 90%, 95%, 96%, 97%, 98%, 99%, or 100% sequence identity to SEQ ID NO: 7. In some embodiments, the nucleic acid molecules encode a polypeptide with an amino acid sequence having at least about 80%, 90%, 95%, 96%, 97%, 98%, 99%, or 100% sequence identity to SEQ ID NO: 8. In some embodiments, the nucleic acid molecules encode a polypeptide with an amino acid sequence having at least about 80%, 90%, 95%, 96%, 97%, 98%, 99%, or 100% sequence identity to SEQ ID NO: 9. In some embodiments, the nucleic acid molecules encode a polypeptide with an amino acid sequence having at least about 80%, 90%, 95%, 96%, 97%, 98%, 99%, or 100% sequence identity to SEQ ID NO: 10. In some embodiments, the nucleic acid molecules encode a polypeptide with an amino acid sequence having at least about 80%, 90%, 95%, 96%, 97%, 98%, 99%, or 100% sequence identity to SEQ ID NO: 11. In some embodiments, the nucleic acid molecules encode a polypeptide with an amino acid sequence having at least about 80%, 90%, 95%, 96%, 97%, 98%, 99%, or 100% sequence identity to SEQ ID NO: 12. In some embodiments, the nucleic acid molecules encode a polypeptide with an amino acid sequence having at least about 80%, 90%, 95%, 96%, 97%, 98%, 99%, or 100% sequence identity to SEQ ID NO: 65. In some embodiments, the nucleic acid molecules encode a polypeptide with an amino acid sequence having at least about 80%, 90%, 95%, 96%, 97%, 98%, 99%, or 100% sequence identity to SEQ ID NO: 66.

The nucleic acid sequences encoding the chimeric receptors can be optimized for expression in the host cell of interest. For example, the G-C content of the sequence can be adjusted to average levels for a given cell, as calculated by reference to known genes expressed in the host cell. Methods for codon usage optimization are known in the art. Codon usages within the coding sequence of the chimeric receptor disclosed herein can be optimized to enhance expression in the host cell, such that about 1%, about 5%, about 10%, about 25%, about 50%, about 75%, or up to 100% of the codons within the coding sequence have been optimized for expression in a particular host cell.

Some embodiments disclosed herein relate to vectors or expression cassettes including a recombinant nucleic acid molecule encoding the chimeric receptors disclosed herein. The expression cassette generally contains coding sequences and sufficient regulatory information to direct proper transcription and/or translation of the coding sequences in a recipient cell, in vivo and/or ex vivo. The expression cassette may be inserted into a vector for targeting to a desired host cell and/or into a subject. An expression cassette can be inserted into a plasmid, cosmid, virus, autonomously replicating polynucleotide molecule, phage, as a linear or circular, single-stranded or double-stranded, DNA or RNA polynucleotide molecule, derived from any source, capable of genomic integration or autonomous replication, including a nucleic acid molecule where one or more nucleic acid sequences has been linked in a functionally operative manner, i.e., operably linked.

Also provided herein are vectors, plasmids, or viruses containing one or more of the nucleic acid molecules encoding a chimeric receptor disclosed herein. The nucleic acid molecules can be contained within a vector that is capable of directing their expression in, for example, a cell that has been transformed/transduced with the vector. Suitable vectors for use in eukaryotic and prokaryotic cells are known in the art and are commercially available, or readily prepared by a skilled artisan. See for example, Sambrook, J., & Russell, D. W. (2012). *Molecular Cloning: A Laboratory Manual* (4th ed.). Cold Spring Harbor, NY: Cold Spring Harbor Laboratory and Sambrook, J., & Russel, D. W. (2001). *Molecular Cloning: A Laboratory Manual* (3rd ed.). Cold Spring Harbor, NY: Cold Spring Harbor Laboratory (jointly referred to herein as "Sambrook"); Ausubel, F. M. (1987). *Current Protocols in Molecular Biology*. New York, NY: Wiley (including supplements through 2014); Bollag, D. M. et al. (1996). *Protein Methods*. New York, NY: Wiley-Liss; Huang, L. et al. (2005). *Nonviral Vectors for Gene Therapy*. San Diego: Academic Press; Kaplitt, M. G. et al. (1995). *Viral Vectors: Gene Therapy and Neuroscience Applications*. San Diego, CA: Academic Press; Lefkovits, I. (1997). *The Immunology Methods Manual: The Comprehensive Sourcebook of Techniques*. San Diego, CA: Academic Press; Doyle, A. et al. (1998). *Cell and Tissue Culture: Laboratory Procedures in Biotechnology*. New York, NY: Wiley; Mullis, K. B., Ferré, F. & Gibbs, R. (1994). *PCR: The Polymerase Chain Reaction*. Boston: Birkhauser Publisher; Greenfield, E. A. (2014). *Antibodies: A Laboratory Manual* (2nd ed.). New York, NY: Cold Spring Harbor Laboratory Press; Beaucage, S. L. et al. (2000). *Current Protocols in Nucleic Acid Chemistry*. New York, NY: Wiley, (including supplements through 2014); and Makrides, S. C. (2003). *Gene Transfer and Expression in Mammalian Cells*. Amsterdam, NL: Elsevier Sciences B.V., the disclosures of which are incorporated herein by reference).

DNA vectors can be introduced into eukaryotic cells via conventional transformation or transfection techniques. Suitable methods for transforming or transfecting host cells can be found in Sambrook et al. (2012, supra) and other standard molecular biology laboratory manuals, such as, calcium phosphate transfection, DEAE-dextran mediated transfection, transfection, microinjection, cationic lipid-mediated transfection, electroporation, transduction, scrape loading, ballistic introduction, nucleoporation, hydrodynamic shock, and infection.

Viral vectors that can be used in the disclosure include, for example, retrovirus vectors, adenovirus vectors, and adeno-associated virus vectors, lentivirus vectors, herpes virus, simian virus 40 (SV40), and bovine papilloma virus vectors (see, for example, Gluzman (Ed.), *Eukaryotic Viral Vectors*, CSH Laboratory Press, Cold Spring Harbor, NY). For example, a chimeric receptor as disclosed herein can be produced in a eukaryotic host, such as a mammalian cells (e.g., COS cells, NIH 3T3 cells, or HeLa cells). These cells are available from many sources, including the American Type Culture Collection (Manassas, VA). In selecting an expression system, care should be taken to ensure that the components are compatible with one another. Artisans of ordinary skill are able to select and design expression systems suitable and functional in a selected engineered cell. If further guidance is required in selecting an expression system, skilled artisans may consult P. Jones, "Vectors: Cloning Applications", John Wiley and Sons, New York, NY, 2009).

The nucleic acid molecules provided can contain naturally occurring sequences, or sequences that differ from those that occur naturally, but, due to the degeneracy of the genetic code, encode the same polypeptide, e.g., antibody. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (e.g., either a sense or an antisense strand).

The nucleic acid molecules are not limited to sequences that encode polypeptides (e.g., antibodies); some or all of the non-coding sequences that lie upstream or downstream from a coding sequence (e.g., the coding sequence of a chimeric receptor) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

Recombinant Cells and Cell Cultures

The nucleic acid of the present disclosure can be introduced into a host cell, such as, for example, a human T lymphocyte, to produce a recombinant cell containing the nucleic acid molecule. Accordingly, some embodiments of the disclosure relate to methods for making a recombinant cell, including (a) providing a cell capable of protein expression and (b) contacting the provided cell with a recombinant nucleic acid of the disclosure.

Introduction of the nucleic acid molecules of the disclosure into cells can be achieved by methods known to those skilled in the art such as, for example, viral infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Accordingly, in some embodiments, the nucleic acid molecules can be delivered by viral or non-viral delivery vehicles known in the art. For example, the nucleic acid molecule can be stably integrated in the host genome, or can be episomally replicating, or present in the recombinant cell as a mini-circle expression vector for transient expression. Accordingly, in some embodiments, the nucleic acid molecule is maintained and replicated in the recombinant cell as an episomal unit. In some embodiments, the nucleic acid molecule is stably integrated into the genome of the recombinant cell. Stable integration can be achieved using classical random genomic recombination techniques or with more precise techniques such as guide RNA-directed CRISPR/Cas9 genome editing, or DNA-guided endonuclease genome editing with NgAgo (*Natronobacterium gregoryi* Argonaute), or TALENs genome editing (transcription activator-like effector nucleases). In some embodiments, the nucleic acid molecule is present in the recombinant cell as a mini-circle expression vector for transient expression.

The nucleic acid molecules can be encapsulated in a viral capsid or a lipid nanoparticle, or can be delivered by viral or non-viral delivery means and methods known in the art, such as electroporation. For example, introduction of nucleic acids into cells may be achieved by viral transduction. In a non-limiting example, adeno-associated virus (AAV) is engineered to deliver nucleic acids to target cells via viral transduction. Several AAV serotypes have been described, and all of the known serotypes can infect cells from multiple diverse tissue types. AAV is capable of transducing a wide range of species and tissues in vivo with no evidence of toxicity, and it generates relatively mild innate and adaptive immune responses.

Lentiviral-derived vector systems are also useful for nucleic acid delivery and gene therapy via viral transduction. Lentiviral vectors offer several attractive properties as gene-delivery vehicles, including: (i) sustained gene delivery through stable vector integration into host genome; (ii) the capability of infecting both dividing and non-dividing cells; (iii) broad tissue tropisms, including important gene- and cell-therapy-target cell types; (iv) no expression of viral proteins after vector transduction; (v) the ability to deliver complex genetic elements, such as polycistronic or intron-containing sequences; (vi) a potentially safer integration site profile; and (vii) a relatively easy system for vector manipulation and production.

In some embodiments, host cells can be genetically engineered (e.g., transduced or transformed or transfected) with, for example, a vector construct of the present application that can be, for example, a viral vector or a vector for homologous recombination that includes nucleic acid sequences homologous to a portion of the genome of the host cell, or can be an expression vector for the expression of the polypeptides of interest. These cells can be either untransformed cells or cells that have already been transfected with at least one nucleic acid molecule.

In some embodiments, the recombinant cell is a prokaryotic cell or a eukaryotic cell. In some embodiments, the cell is in vivo. In some embodiments, the cell is ex vivo. In some embodiments, the cell is in vitro. In some embodiments, the recombinant cell is a prokaryotic cell including a recombinant nucleic acid as disclosed herein. In some embodiments, the recombinant prokaryotic cell includes a recombinant nucleic acid which is a cloning vector. In some embodiments, the recombinant cell is a eukaryotic cell. In some embodiments, the recombinant cell is an animal cell. In some embodiments, the animal cell is a mammalian cell. In some embodiments, the animal cell is a human cell. In some embodiments, the cell is a non-human primate cell. In some embodiments, the mammalian cell is an immune cell, a neuron, an epithelial cell, and endothelial cell, or a stem cell. In some embodiments, the recombinant cell is an immune system cell, e.g., a lymphocyte (e.g., a T cell or NK cell), or a dendritic cell. In some embodiments, the immune cell is a B cell, a monocyte, a natural killer (NK) cell, a basophil, an eosinophil, a neutrophil, a dendritic cell, a macrophage, a regulatory T cell, a helper T cell ($T_H$), a cytotoxic T cell ($T_{CTL}$), or other T cell. In some embodiments, the immune system cell is a T lymphocyte.

In some embodiments, the cell is a stem cell. In some embodiments, the cell is a hematopoietic stem cell. In some embodiments of the cell, the cell is a lymphocyte. In some embodiments, the cell is a precursor T cell or a T regulatory (Treg) cell. In some embodiments, the cell is a CD34+, CD8+, or a CD4+ cell. In some embodiments, the cell is a CD8+T cytotoxic lymphocyte cell selected from the group consisting of naïve CD8+ T cells, central memory CD8+ T cells, effector memory CD8+ T cells, and bulk CD8+ T cells. In some embodiments of the cell, the cell is a CD4+T helper lymphocyte cell selected from the group consisting of naïve CD4+ T cells, central memory CD4+ T cells, effector memory CD4+ T cells, and bulk CD4+ T cells. In some embodiments, the cell can be obtained by leukapheresis performed on a sample obtained from a subject. In some embodiments, the subject is a human patient.

In some embodiments, the recombinant cell further includes a first and a second nucleic acid molecule as disclosed herein, wherein the first nucleic acid molecule and the second nucleic acid molecule do not have the same sequence. In some embodiments, the recombinant cell further includes a first and a second chimeric polypeptide as disclosed herein, wherein the first chimeric polypeptide and the second chimeric polypeptide do not have the same sequence. In some embodiments, the first chimeric polypeptide modulates the expression and/or activity of the second chimeric polypeptide.

In some embodiments, the recombinant cell further includes an expression cassette or vector encoding a protein of interest operably linked to a promoter, wherein expression of the protein is modulated by the chimeric receptor's transcriptional effector. In some embodiments, the protein of interest is heterologous to the recombinant cell. In some embodiments, the heterologous protein is one that is not normally found in the cell, e.g., not normally produced by the cell. In some embodiments, the expression vector encodes a copy of a protein that is already present in the cell. Exemplary types of proteins suitable for use with the compositions and methods disclosed herein include cytokines, cytotoxins, chemokines, immunomodulators, pro-apoptotic factors, anti-apoptotic factors, hormones, differentiation factors, dedifferentiation factors, immune cell receptors, or reporters.

In some embodiments, the immune cell receptor is a T-cell receptor (TCR). In some embodiments, the immune cell receptor is a chimeric antigen receptor (CAR). In some embodiments, the expression cassette encoding the protein of interest is incorporated into the same nucleic acid molecule that encodes the chimeric receptor of the disclosure. In some embodiments, the expression cassette encoding the protein of interest is incorporated into a second expression vector that is separate from the nucleic acid molecule encoding the chimeric receptor of the disclosure. In another aspect, provided herein are cell cultures including at least one recombinant cell as disclosed herein, and a culture medium. Generally, the culture medium can be any suitable culture medium for culturing the cells described herein. Techniques for transforming a wide variety of the above-mentioned cells and species are known in the art and described in the technical and scientific literature. Accordingly, cell cultures including at least one recombinant cell as disclosed herein are also within the scope of this application. Methods and systems suitable for generating and maintaining cell cultures are known in the art.

Pharmaceutical Compositions

In some embodiments, the nucleic acids and/or recombinant cells of the disclosure can be incorporated into compositions, including pharmaceutical compositions. Such compositions include one or more of the nucleic acids and/or recombinant cells as disclosed herein, and a pharmaceutically acceptable excipient, e.g., a carrier.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be generally to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above.

In some embodiments, the chimeric polypeptides and Notch receptors of the disclosure can also be administered by transfection or infection using methods known in the art, including but not limited to the methods described in McCaffrey et al. (*Nature* 418:6893, 2002), Xia et al. (*Nature Biotechnol.* 20:1006-10, 2002), or Putnam (*Am. J. Health Syst. Pharm.* 53:151-60, 1996, erratum at *Am. J. Health Syst. Pharm.* 53:325, 1996).

As described in greater detail below, in some embodiments, the recombinant cells of the disclosure can be formulated for administration to a subject using techniques known to the skilled artisan. For example, formulations comprising populations of recombinant cells can include pharmaceutically acceptable excipient(s). Excipients included in the formulations will have different purposes depending, for example, on the recombinant cells used and the mode of administration. Examples of generally used excipients included, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents. The formulations comprising recombinant cells can have been prepared and cultured in the absence of non-human components, e.g., in the absence of animal serum. A formulation can include one population of recombinant cells, or more than one, such as two, three, four, five, six or more populations of recombinant cells.

Formulations comprising population(s) of recombinant cells can be administered to a subject using modes and techniques known to the skilled artisan. Exemplary modes include, but are not limited to, intravenous injection. Other modes include, without limitation, intratumoral, intradermal, subcutaneous (S.C., s.q., sub-Q, Hypo), intramuscular (i.m.), intraperitoneal (i.p.), intra-arterial, intramedullary, intracardiac, intra-articular (joint), intrasynovial (joint fluid area), intracranial, intraspinal, and intrathecal (spinal fluids). Devices useful for parenteral injection of infusion of the formulations can be used to effect such administration.

Methods of the Disclosure

Administration of any one of the therapeutic compositions described herein, e.g., chimeric polypeptides, humanized HingeNotch receptors, nucleic acids, recombinant cells, and pharmaceutical compositions, can be used to treat patients for relevant diseases, such as cancers and chronic infections. In some embodiments, the nucleic acids, recombinant cells, and pharmaceutical compositions described herein can be incorporated into therapeutic agents for use in methods of treating or aiding in the treatment of a subject who has, who is suspected of having, or who may be at high risk for developing one or more diseases.

Accordingly, in one aspect, some embodiments of the disclosure relate to methods for inhibiting an activity of a target cell in a subject, the methods include administering to the subject a first therapy including one or more of nucleic acids, recombinant cells, and pharmaceutical compositions as disclosed herein, wherein the first therapy inhibits the target cell. For example, the target cell may be inhibited if its proliferation is reduced, if its pathologic or pathogenic behavior is reduced, if it is destroyed or killed, etc. Inhibition includes a reduction of the measured pathologic or pathogenic behavior of at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In some embodiments, the methods include administering to the subject an effective number of the recombinant cells disclosed herein, wherein the recombinant cells inhibit an activity of the target cells in the subject. Generally, the target cells of the disclosed methods can be any cell type in a subject and can be, for example an acute myeloma leukemia cell, an anaplastic lymphoma cell, an astrocytoma cell, a B-cell cancer cell, a breast cancer cell, a colon cancer cell, an ependymoma cell, an esophageal cancer cell, a glioblastoma cell, a glioma cell, a leiomyosarcoma cell, a liposarcoma cell, a liver cancer cell, a lung cancer cell, a mantle cell lymphoma cell, a melanoma cell, a neuroblastoma cell, a non-small cell lung cancer cell, an oligodendroglioma cell, an ovarian cancer cell, a pancreatic cancer cell, a peripheral T cell lymphoma cell, a renal cancer cell, a sarcoma cell, a stomach cancer cell, a carcinoma cell, a mesothelioma cell, or a sarcoma cell. In some embodiments, the target cell is a pathogenic cell.

In another aspect, some embodiments of the disclosure relate to methods for aiding in the treatment of a disease in a subject in need thereof, the methods including administering to the subject a first therapy including one or more of the recombinant cells including a chimeric polypeptide as disclosed herein, and/or pharmaceutical compositions as disclosed herein, wherein the first therapy treats the disease in the subject. In some embodiments, the methods include administering to the subject a first therapy including an effective number of the recombinant cells as disclosed herein, wherein the recombinant cells treat the disease.

In another aspect, some embodiments of the disclosure relate to methods for assisting or aiding in the treatment of a disease in a subject in need thereof, the methods including administering to the subject a first therapy including one or more of chimeric polypeptides, humanized HingeNotch receptors, nucleic acids, recombinant cells, and pharmaceutical compositions as disclosed herein, and a second therapy, wherein the first and second therapies together treat the disease in the subject. In some embodiments, the methods include administering to the subject a first therapy including an effective number of the recombinant cells as disclosed herein, wherein the recombinant cells treat the disease.

Administration of Recombinant Cells to a Subject

In some embodiments, the methods of the disclosure involve administering an effective amount or number of the recombinants cells to a subject in need of such treatment. This administering step can be accomplished using any method of implantation delivery in the art. For example, the recombinant cells can be infused directly in the subject's bloodstream or otherwise administered to the subject.

In some embodiments, the methods disclosed herein include administering, which term is used interchangeably with the terms "introducing", implanting", and "transplanting", recombinant cells into a subject, by a method or route that results in at least partial localization of the introduced cells at a desired site such that a desired effect(s) is/are produced. The recombinant cells or their differentiated progeny can be administered by any appropriate route that results in delivery to a desired location in the subject where at least a portion of the administered cells or components of the cells remain viable. The period of viability of the cells after administration to a subject can be as short as a few hours, e.g., twenty-four hours, to a few days, to as long as several years, or even the lifetime of the subject, i.e., long-term engraftment.

When provided prophylactically, the recombinant cells described herein can be administered to a subject in advance of a symptom of a disease or condition to be treated. Accordingly, in some embodiments the prophylactic administration of a recombinant cell population prevents the occurrence of symptoms of the disease or condition.

When provided therapeutically in some embodiments, recombinant cells are provided at (or after) the onset of a symptom or indication of a disease or condition, e.g., upon the onset of disease or condition.

For use in the various embodiments described herein, an effective amount of recombinant cells as disclosed herein, can be at least $10^2$ cells, at least $5\times10^2$ cells, at least $10^3$ cells, at least $5\times10^3$ cells, at least $10^4$ cells, at least $5\times10^4$ cells, at least $10^5$ cells, at least $2\times10^5$ cells, at least $3\times10^5$ cells, at least $4\times10^5$ cells, at least $5\times10^5$ cells, at least $6\times10^5$ cells, at least $7 \times 10^5$ cells, at least $8 \times 10^5$ cells, at least $9 \times 10^5$ cells, at least $1 \times 10^6$ cells, at least $2 \times 10^6$ cells, at least $3 \times 10^6$ cells, at least $4 \times 10^6$ cells, at least $5 \times 10^6$ cells, at least $6 \times 10^6$ cells, at least $7 \times 10^6$ cells, at least $8 \times 10^6$ cells, at least $9 \times 10^6$ cells, or multiples thereof. The recombinant cells can be derived from one or more donors or can be obtained from an autologous source. In some embodiments, the recombinant cells are expanded in culture prior to administration to a subject in need thereof.

In some embodiments, the delivery of a recombinant cell composition (e.g., a composition including a plurality of recombinant cells according to any of the cells described herein) into a subject by a method or route results in at least partial localization of the cell composition at a desired site. A composition including recombinant cells can be administered by any appropriate route that results in effective treatment in the subject, e.g., administration results in delivery to a desired location in the subject where at least a portion of the composition delivered, e.g., at least $1 \times 10^4$ cells, is delivered to the desired site for a period of time. Modes of administration include injection, infusion, instillation. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion. In some embodiments, the route is intravenous. For the delivery of cells, delivery by injection or infusion is a standard mode of administration.

In some embodiments, the recombinant cells are administered systemically, e.g., via infusion or injection. For example, a population of recombinant cells are administered other than directly into a target site, tissue, or organ, such that it enters, the subject's circulatory system and, thus, is subject to metabolism and other similar biological processes.

The efficacy of a treatment including any of the compositions provided herein for the treatment of a disease or condition can be determined by a skilled clinician. However, one skilled in the art will appreciate that a treatment is considered effective if any one or all of the signs or symptoms or markers of disease are improved or ameliorated. Efficacy can also be measured by failure of a subject to worsen as assessed by decreased hospitalization or need for medical interventions (e.g., progression of the disease is halted or at least slowed). Methods of measuring these indicators are known to those of skill in the art and/or described herein. Treatment includes any treatment of a disease in a subject or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

In some embodiments of the disclosed methods, the subject is a mammal. In some embodiments, the mammal is a human. In some embodiments, the subject has or is suspected of having a disease associated with inhibition of cell signaling mediated by a cell surface ligand or antigen. The diseases suitable for being treated by the compositions and methods of the disclosure include, but are not limited to, cancers, autoimmune diseases, inflammatory diseases, and infectious diseases. In some embodiments, the disease is a cancer or a chronic infection.

Additional Therapies

As discussed above, the recombinant cells, and pharmaceutical compositions described herein can be administered in combination with one or more additional therapeutic agents such as, for example, chemotherapeutics or anti-cancer agents or anti-cancer therapies. Administration "in combination with" one or more additional therapeutic agents includes simultaneous (concurrent) and consecutive administration in any order. In some embodiments, the one or more additional therapeutic agents, chemotherapeutics, anti-cancer agents, or anti-cancer therapies is selected from the group consisting of chemotherapy, radiotherapy, immunotherapy, hormonal therapy, toxin therapy, and surgery. "Chemotherapy" and "anti-cancer agent" are used interchangeably herein. Various classes of anti-cancer agents can be used. Non-limiting examples include: alkylating agents, antimetabolites, anthracyclines, plant alkaloids, topoisomerase inhibitors, podophyllotoxin, antibodies (e.g., monoclonal or polyclonal), tyrosine kinase inhibitors (e.g., imatinib mesylate (Gleevec® or Glivec®)), hormone treatments, soluble receptors and other antineoplastics.

Accordingly, in some embodiments, the disclosed treatment methods further include administering to the subject a second therapy. Generally, the second therapy can be any therapy known in the art. Non-limiting examples of therapies suitable for use in combination with the therapeutic compositions disclosed herein include chemotherapy, radiotherapy, immunotherapy, hormonal therapy, toxin therapy, and surgery. In some embodiments, the second therapy includes one or more additional therapeutic agents such as, for example, chemotherapeutics or anti-cancer agents or anti-cancer therapies. In some embodiments, the first therapy and the second therapy are administered together in the same composition. In some embodiments, the first therapy and the second therapy are administered in separate compositions. In some embodiments, the first therapy and the second therapy are administered at the same time. In some embodiments, the first therapy and the second therapy are administered sequentially. In some embodiments, the first therapy is administered before the second therapy. In some embodiments, the first therapy is administered after the second therapy. In some embodiments, the first therapy and the second therapy are administered in rotation.

Methods for Modulating an Activity of a Cell

In another aspect, provided herein are various methods for modulating an activity of a cell. The methods include the steps of: (a) providing an effective amount of any of the recombinant cells provided herein, and (b) contacting it with a selected ligand, wherein binding of the selected ligand to the extracellular ligand-binding domain induces cleavage of a ligand-inducible proteolytic cleavage site and releases the transcriptional effector, wherein the released transcriptional effector modulates an activity of the recombinant cell. One skilled in the art upon reading the present disclosure will appreciate that the disclosed methods can be carried out in vivo, ex vivo, or in vitro.

Non-limiting exemplary cellular activities that can be modulated using the methods provide herein include, but are not limited to, gene expression, proliferation, apoptosis, non-apoptotic death, differentiation, dedifferentiation, migration, secretion of a gene product, cellular adhesion, and cytolytic activity.

In some embodiments, the released transcriptional effector modulates expression of a gene product of the cell. In some embodiments, the released transcriptional effector modulates expression of a heterologous gene product in the cell. A heterologous gene product is one that is not normally found in the native cell, e.g., not normally produced by the cell. For example, the cell can be genetically modified with a nucleic acid including a nucleotide sequence encoding a heterologous gene product.

In some embodiments, the heterologous gene product is a secreted gene product. In some embodiments, the heterologous gene product is a cell surface gene product. In some cases, the heterologous gene product is an intracellular gene product. In some embodiments, the released transcriptional effector simultaneously modulates expression of two or more heterologous gene products in the cell.

In some embodiments, the gene product in the cell is selected from the group consisting of a chemokine, a chemokine receptor, a chimeric antigen receptor, a cytokine, a cytokine receptor, a differentiation factor, a growth factor, a growth factor receptor, a hormone, a metabolic enzyme, a pathogen-derived protein, a proliferation inducer, a receptor, an RNA guided nuclease, a site-specific nuclease, a T cell receptor (TCR) or a component thereof, a chimeric antigen receptor (CAR), a toxin, a toxin-derived protein, a transcriptional effector, a transcriptional activator, a transcriptional repressor, a translation regulator, a translational activator, a translational repressor, an activating immuno-receptor, an antibody, an apoptosis inhibitor, an apoptosis inducer, an engineered T cell receptor, an immuno-activator, an immuno-inhibitor, and an inhibiting immuno-receptor.

In some embodiments, the released transcriptional effector modulates (e.g., activates) expression of a protein which can then enhance cytotoxicity or cell proliferation, or to avoid exhaustion, such as IFN$\gamma$, IL-2, etc.

In some embodiments, the released transcriptional effector modulates differentiation of the cell, and the cell is an immune cell, a stem cell, a progenitor cell, or a precursor cell.

The chimeric polypeptides of the present disclosure provide a higher degree of expression than existing first-generation SynNotch receptors, when using identical binding domains and ICDs. Depending on the ligand/binding domain pair and their affinity, the chimeric polypeptides of the disclosure can provide expression enhancement of at least about 10%, about 15%, about 20%, about 25%, about 30%, about 35%, about 40%, about 45%, about 50% higher than a corresponding SynNotch receptor. In some embodiments, the chimeric polypeptides of the disclosure can provide expression enhancement of at least about 50%, about 100%, about 150%, about 200%, about 250%, about 300%, about 400%, about 500%, about 600% higher than a corresponding SynNotch receptor.

Additionally, the chimeric polypeptides of the disclosure can provide transcriptional regulation that responds to the degree of T cell activation, independent of ligand binding. For example, when expressed in a T cell, some receptors of the disclosure provide a stronger ligand-induced signal when the T cell is activated as compared to the ligand-induced signal when the T cell is not activated. This permits additional flexibility in use, for example in cases where it is desired to enhance or suppress a T cell response when activated despite the absence of the chimeric receptor ligand.

Systems and Kits

Also provided herein are kits including the chimeric polypeptides, humanized HingeNotch receptors, recombinant nucleic acids, recombinant cells, or pharmaceutical compositions provided and described herein as well as written instructions for making and using the same. For example, provided herein, in some embodiments, are kits that include one or more of the following: (i) a chimeric polypeptide as described herein, (ii) a recombinant nucleic acids as described herein, (iii) a recombinant cell as described herein, and (iv) a pharmaceutical composition as described herein. In some embodiments, the systems and/or kits of the disclosure further include one or more syringes (including pre-filled syringes) and/or catheters (including pre-filled syringes) used to administer one any of the provided recombinant nucleic acids, recombinant cells, or pharmaceutical compositions to a subject. In some embodiments, a kit can have one or more additional therapeutic agents that can be administered simultaneously or sequentially with the other kit components for a desired purpose, e.g., for modulating an activity of a cell, inhibiting a target cancer cell, or treating a disease in a subject in need thereof.

Any of the above-described systems and kits can further include one or more additional reagents, where such additional reagents can be selected from: dilution buffers; reconstitution solutions, wash buffers, control reagents, control expression vectors, negative control polypeptides, positive control polypeptides, reagents for in vitro production of the chimeric receptor polypeptides.

In some embodiments, a system or kit can further include instructions for using the components of the kit to practice the methods. The instructions for practicing the methods are generally recorded on a suitable recording medium. For example, the instructions can be printed on a substrate, such as paper or plastic, etc. The instructions can be present in the kits as a package insert, in the labeling of the container of the kit or components thereof (i.e., associated with the packaging or sub-packaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g., via the internet), are provided. An example of this embodiment is a kit that includes a web address where the instructions can be viewed and/or from which the instructions can be downloaded. As with the instructions, this means for obtaining the instructions can be recorded on a suitable substrate.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

Throughout this specification, various patents, patent applications and other types of publications (e.g., journal articles, electronic database entries, etc.) are referenced. The disclosure of all patents, patent applications, and other publications cited herein are hereby incorporated by reference in their entirety to the same extent as if each individual publication or patent application was specifically and individually indicated to be incorporated by reference.

EXAMPLES

The practice of the present disclosure will employ, unless otherwise indicated, conventional techniques of molecular biology, microbiology, cell biology, biochemistry, nucleic acid chemistry, and immunology, which are well known to those skilled in the art. Such techniques are explained fully in the literature cited above.

Additional embodiments are disclosed in further detail in the following examples, which are provided by way of illustration and are not in any way intended to limit the scope of this disclosure or the claims.

Example 1

Design and Construction of Chimeric Receptor and Response Element Constructs

This Example describes the design and construction of a family of humanized Notch receptors in accordance with some embodiments of the disclosure. Detailed information for various exemplary receptors of the disclosure can be found in Tables 1 and 2 below.

In these Notch receptors, the DBD sequence was fused N-terminally to the TAD sequence, with the exception of receptor pRay242 where the DBD sequence was fused C-terminally to the TAD sequence. The TAD sequence was preceded by a 3-amino acid linker sequence (TCR) in the following receptors pRay239 (SEQ ID NO: 1), pRay240 (SEQ ID NO: 2), pRay241 (SEQ ID NO: 3), pRay243 (SEQ ID NO: 5), pRay244 (SEQ ID NO: 6), pRay250 (SEQ ID NO: 7), pRay251 (SEQ ID NO: 8), pRay252 (SEQ ID NO: 9).

A compact 4× Pax6 response element (SEQ ID NO: 67) was developed for the construction of single vector designs such as, pRay445B and pRay451C. This compact 4× Pax6 response element consists of the consensus Pax6 recognition motif ATTTTCACGCATGAGTGCACAG (SEQ ID NO: 59) repeated 4 times and with spacer sequences removed. This sequence (SEQ ID NO: 67) was placed upstream of a minimal TATA promoter, and together this was cloned into the EcoRI/BamHI sites of the general lentiviral vector (called "EcoRI (GAATCC)-BamHI (GGATCC)-linearized Response Element Plasmid vector sequence", and described in SEQ ID NO: 64).

Into this vector, the following FLAG-tagged BCMA-CAR construct was inserted between the BamHI (GGATCC) and NotI (GCGGCCGC) sites of the response vector using standard cloning techniques. The sequence of the resulting plasmid is provided in SEQ ID NO: 68. This is a second generation CAR that included the following elements: Kozak sequence (gccgccacc), CD8α signal peptide sequence (SEQ ID NO: 689), FLAG-tag (SEQ ID NO: 70), Anti-BCMA scFv (SEQ ID NO: 71), CD8 TMD (SEQ ID NO: 72), 41BB (SEQ ID NO: 73), and CD3z (SEQ ID NO: 74).

The humanized hingeNotch receptor was placed downstream of a mouse PGK promoter, and together inserted into the SbfI site (CCTGCAGG) of the general response vector. The receptor sequences are provided in the updated excel file, and the PGK promoter sequence is provided in SEQ ID NO: 75.

Together, the general architecture of the single vector design of pRay445B and pRay451C is as follows:

[Compact 4×PAX6 Response Element]–[minimal
TATA promoter]–[FLAG-TAGGED anti-BCMA
CAR]–[mouse PGK promoter]–[pRay445B or
pRay451C sequence]

TABLE 1

This table provides a brief description for each of the chimeric Notch receptors, their corresponding
components, as well as corresponding sequence identifiers as set forth in the Sequence Listing.
ECD: extracellular domain; N-JMD: N-terminal juxtamembrane domain; TMD: transmembrane domain;
STS: stop-transfer-sequence; DBD: DNA-binding domain; TAD: transactivation domain.

| Construct ID | Receptor Description | ECD | N-JMD | TMD | STS | DBD | TAD | Full sequence |
|---|---|---|---|---|---|---|---|---|
| pRay239 | antiCD19scFv-Notch1deltaNRR-Notch2STS-HNF1aDBD-p65(361-551) | SEQ ID NO: 13 | SEQ ID NO: 14 | SEQ ID NO: 21 | SEQ ID NO: 31 | SEQ ID NO: 52 | SEQ ID NO: 54 | SEQ ID NO: 1 |
| pRay240 | antiCD19scFv-CD8Hinge2-Notch1TMD-Notch2STS-HNF1aDBD-p65(361-551) | SEQ ID NO: 13 | SEQ ID NO: 15 | SEQ ID NO: 21 | SEQ ID NO: 31 | SEQ ID NO: 52 | SEQ ID NO: 54 | SEQ ID NO: 2 |
| pRay241 | antiCD19scFv-RoboFn-Notch1TMD-HNF1aDBD-p65(361-551) | SEQ ID NO: 13 | SEQ ID NO: 20 | SEQ ID NO: 21 | SEQ ID NO: 31 | SEQ ID NO: 52 | SEQ ID NO: 54 | SEQ ID NO: 3 |
| pRay242 | antiCD19scFv-CD8Hinge2-Notch1TMD-Notch2STS-p65(361-551)-HNF1aDBD | SEQ ID NO: 13 | SEQ ID NO: 15 | SEQ ID NO: 21 | SEQ ID NO: 31 | SEQ ID NO: 52 | SEQ ID NO: 54 | SEQ ID NO: 4 |
| pRay243 | antiCD19scFv-CD8Hinge2-Notch1(1758-1878)-HNF1aDBD-p65(361-551) | SEQ ID NO: 13 | SEQ ID NO: 15 | SEQ ID NO: 21 | SEQ ID NO: 32 | SEQ ID NO: 52 | SEQ ID NO: 54 | SEQ ID NO: 5 |
| pRay244 | antiCD19scFv-CD8Hinge2-Notch1(1758-1788)-HNF1aDBD-p65(361-551) | SEQ ID NO: 13 | SEQ ID NO: 15 | SEQ ID NO: 21 | SEQ ID NO: 33 | SEQ ID NO: 52 | SEQ ID NO: 54 | SEQ ID NO: 6 |
| pRay250 | antiCD19scFv-CD8Hinge2-Notch1(1758-1800)-HNF1aDBD-p65(361-551) | SEQ ID NO: 13 | SEQ ID NO: 15 | SEQ ID NO: 21 | SEQ ID NO: 34 | SEQ ID NO: 52 | SEQ ID NO: 54 | SEQ ID NO: 7 |
| pRay251 | antiCD19scFv-CD8Hinge2-Notch1(1758-1825)-HNF1aDBD-p65(361-551) | SEQ ID NO: 13 | SEQ ID NO: 15 | SEQ ID NO: 21 | SEQ ID NO: 35 | SEQ ID NO: 52 | SEQ ID NO: 54 | SEQ ID NO: 8 |
| pRay252 | antiCD19scFv-CD8Hinge2-Notch1(1758-1850)-HNF1aDBD-p65(361-551) | SEQ ID NO: 13 | SEQ ID NO: 15 | SEQ ID NO: 21 | SEQ ID NO: 36 | SEQ ID NO: 52 | SEQ ID NO: 54 | SEQ ID NO: 9 |
| pRay253 | antiCD19scFv-CD8Hinge2-Notch1(1758-1878)-Pax6DBD-p65(428-551) | SEQ ID NO: 13 | SEQ ID NO: 15 | SEQ ID NO: 21 | SEQ ID NO: 32 | SEQ ID NO: 53 | SEQ ID NO: 55 | SEQ ID NO: 10 |

TABLE 1-continued

This table provides a brief description for each of the chimeric Notch receptors, their corresponding
components, as well as corresponding sequence identifiers as set forth in the Sequence Listing.
ECD: extracellular domain; N-JMD: N-terminal juxtamembrane domain; TMD: transmembrane domain;
STS: stop-transfer-sequence; DBD: DNA-binding domain; TAD: transactivation domain.

| Construct ID | Receptor Description | ECD | N-JMD | TMD | STS | DBD | TAD | Full sequence |
|---|---|---|---|---|---|---|---|---|
| pRay254 | antiCD19scFv-CD8Hinge2-Notch1(1758-1788)-Pax6DBD-p65(428-551) | SEQ ID NO: 13 | SEQ ID NO: 15 | SEQ ID NO: 21 | SEQ ID NO: 33 | SEQ ID NO: 53 | SEQ ID NO: 55 | SEQ ID NO: 11 |
| pRay255 | antiCD19scFv-CD8Hinge2-Notch1TMD-Notch2STS-Pax6DBD-p65(428-551) | SEQ ID NO: 13 | SEQ ID NO: 15 | SEQ ID NO: 21 | SEQ ID NO: 31 | SEQ ID NO: 53 | SEQ ID NO: 55 | SEQ ID NO: 12 |
| pRay445B | antiCD19scFv-CD8Hinge2-Notch1TMD-Notch2STS-Pax6DBD-p65(428-551) | SEQ ID NO: 13 | SEQ ID NO: 15 | SEQ ID NO: 21 | SEQ ID NO: 31 | SEQ ID NO: 53 | SEQ ID NO: 55 | SEQ ID NO: 65 |
| pRay151C | antiCD19scFv-CD8Hinge2-Notch1TMD-Notch2STS-Pax6DBD-p65(361-551) | SEQ ID NO: 13 | SEQ ID NO: 15 | SEQ ID NO: 21 | SEQ ID NO: 31 | SEQ ID NO: 53 | SEQ ID NO: 54 | SEQ ID NO: 66 |

TABLE 2

This table provides a brief description for each of the chimeric Notch receptors and
the respective components (with components separated by commas). Unless otherwise
noted, the entry refers to a protein of human origin. For example, "Notch1, Notch1"
indicates that two sequences from Notch1 were fused to generate this protein module.

| Construct ID | Receptor Description | ECD | N-JMD | TMD | STS | DBD | TAD |
|---|---|---|---|---|---|---|---|
| pRay239 | anti-CD19 scFv "miniNotch1" receptor with Notch2STS, HNF1a DNA-binding domain and p65(361-551) transactivation domain | CD8a signal peptide, myc-tag, anti-CD19 scFv | Notch1, Notch1 | Notch1 | Notch2 | HNF1a | p65 |
| pRay240 | anti-CD19 scFv "HingeNotch1" receptor with Notch2STS, HNF1a DNA-binding domain and p65(361-551) transactivation domain | CD8a signal peptide, myc-tag, anti-CD19 scFv | truncated CD8 hinge | Notch1 | Notch2 | HNF1a | p65 |
| pRay241 | anti-CD19 scFv "Robo1-Notch1" receptor with Notch2STS, HNF1a DNA-binding domain and p65(361-551) transactivation domain | CD8a signal peptide, myc-tag, anti-CD19 scFv | Robo1 | Notch1 | Notch2 | HNF1a | p65 |
| pRay242 | anti-CD19 scFv "HingeNotch1" receptor with Notch2STS; fused to a p65(361-551) transactivation domain and HNF1a DNA-binding domain (fusion order TAD-DBD) | CD8a signal peptide, myc-tag, anti-CD19 scFv | truncated CD8 hinge | Notch1 | Notch2 | HNF1a | p65 |
| pRay243 | anti-CD19 scFv "HingeNotch1" receptor with Notch1 ICD extension to aa1878, and HNF1a DNA-binding domain and p65(361-551) transactivation domain | CD8a signal peptide, myc-tag, anti-CD19 scFv | truncated CD8 hinge | Notch1 | Notch1 | HNF1a | p65 |
| pRay244 | anti-CD19 scFv "HingeNotch1" receptor with Notch1 ICD extension to aa1788, and HNF1a DNA-binding domain and p65(361-551) transactivation domain | CD8a signal peptide, myc-tag, anti-CD19 scFv | truncated CD8 hinge | Notch1 | Notch1 | HNF1a | p65 |
| pRay250 | anti-CD19 scFv "HingeNotch1" receptor with Notch1 ICD extension to aa1800, and HNF1a DNA-binding domain and p65(361-551) transactivation domain | CD8a signal peptide, myc-tag, anti-CD19 scFv | truncated CD8 hinge | Notch1 | Notch1 | HNF1a | p65 |
| pRay251 | anti-CD19 scFv "HingeNotch1" receptor with Notch1 ICD extension to aa1825, and HNF1a DNA-binding domain and p65(361-551) transactivation domain | CD8a signal peptide, myc-tag, anti-CD19 scFv | truncated CD8 hinge | Notch1 | Notch1 | HNF1a | p65 |

TABLE 2-continued

This table provides a brief description for each of the chimeric Notch receptors and the respective components (with components separated by commas). Unless otherwise noted, the entry refers to a protein of human origin. For example, "Notch1, Notch1" indicates that two sequences from Notch1 were fused to generate this protein module.

| Construct ID | Receptor Description | ECD | N-JMD | TMD | STS | DBD | TAD |
|---|---|---|---|---|---|---|---|
| pRay252 | anti-CD19 scFv "HingeNotch1" receptor with Notch1 ICD extension to aa1850, and HNF1a DNA-binding domain and p65(361-551) transactivation domain | CD8a signal peptide, myc-tag, anti-CD19 scFv | truncated CD8 hinge | Notch1 | Notch1 | HNF1a | p65 |
| pRay253 | anti-CD19 scFv "HingeNotch1" receptor with Notch1 ICD extension to aa1878, and Pax6 DNA-binding domain and p65(428-551) transactivation domain | CD8a signal peptide, myc-tag, anti-CD19 scFv | truncated CD8 hinge | Notch1 | Notch1 | Pax6 | p65 |
| pRay254 | anti-CD19 scFv "HingeNotch1" receptor with Notch1 ICD extension to aa1788, and Pax6 DNA-binding domain and p65(428-551) transactivation domain | CD8a signal peptide, myc-tag, anti-CD19 scFv | truncated CD8 hinge | Notch1 | Notch1 | Pax6 | p65 |
| pRay255 | anti-CD19 scFv "HingeNotch1" receptor with Notch2STS; Pax6 DNA-binding domain and p65(428-551) transactivation domain | CD8a signal peptide, myc-tag, anti-CD19 scFv | truncated CD8 hinge | Notch1 | Notch2 | Pax6 | p65 |
| pRay445B | anti-CD19 scFv "HingeNotch1" receptor with Notch2STS; Pax6 DNA-binding domain and p65(428-551) transactivation domain with response element driving an anti-BCMA CAR on the same vector | CD8a signal peptide, myc-tag, anti-CD19 scFv | truncated CD8 hinge | Notch1 | Notch2 | Pax6 | p65 |
| pRay151C | anti-CD19 scFv "HingeNotch1" receptor with Notch2STS; Pax6 DNA-binding domain and p65(361-551) transactivation domain with response element driving an anti-BCMA CAR on the same vector | CD8a signal peptide, myc-tag, anti-CD19 scFv | truncated CD8 hinge | Notch1 | Notch2 | Pax6 | p65 |

The chimeric receptors described in Tables 1-2 above were built by fusing a single-chain antigen-binding fragment CD19 scFv (Porter D L et al., 2011) to the corresponding receptor scaffold, a human or humanized transcriptional effector, and a transactivation domain derived from human nuclear factor NFκB p65 subunit (p65). For the construction of these receptors, DNA fragments coding for the amino acid sequences provided in Table 1 and Sequence Listing were PCR amplified from synthesized gene fragments or plasmids containing DNA sequence for the indicated protein, and assembled using standard cloning techniques (e.g., overhang PCR, fusion PCR, and In-fusion cloning) with flanking translation start and stop sequences, into a modified lentiviral pHR' SIN:CSW vector (KT Roybal et al., *Cell* 2016 Oct. 6; 167(2):419-32) containing a phosphoglycerate kinase (PGK) promoter for all primary T cell experiments described in Examples 5-7 below. All receptor constructs also contained an N-terminal CD8α signal peptide (MALPVTALLLPLALLLHAARP; SEQ ID NO: 56) for membrane targeting and a myc-tag (EQKLISEEDL; SEQ ID NO: 57) for convenient determination of surface expression with an antibody conjugated to a fluorescent dye (α-myc A647®, Cell Signaling Technology, Cat #2233).

The pHR' SIN:CSW vector was also modified to produce the response element plasmids. For HNF1α-based receptors, a response element plasmid was constructed using a synthetic binding site including four copies of the inverted repeats 5'-GTTAAT-3' and 5'-ATTAAC-3' were cloned 5' to a minimal TATA promoter. This cassette was inserted into the EcoRI and BamHI restriction sites of pHR' SIN:CSW. For Pax6-based receptors, four copies of a consensus Pax6 binding site, ATTTTCACGCATGAGTGCACAG (SEQ ID NO: 59), were cloned 5' to a minimal TATA promoter and inserted via the EcoRI and BamHI restriction sites. Also included in the response element plasmids was a PGK promoter that constitutively drives expression of a yellow fluorescent reporter protein (mCitrine) for convenient identification of successfully transduced T cells.

For the construction of all inducible BFP vectors, the coding sequence for a blue fluorescent reporter protein (BFP) was cloned via a BamHI site in the multiple cloning site located 3' to the response elements. For the construction of all inducible CAR vectors, the CARs were tagged C-terminally with a green fluorescent reporter protein (GFP) and were cloned via a BamHI site in the multiple cloning site located 3' to the response elements. All constructs were cloned via standard cloning techniques and In-Fusion® cloning kit (Clontech #ST0345) according to the manufacturer's instructions.

Example 2

Primary Human T Cell Isolation and Culture

This Example describes the isolation and culture of primary human T cells that were subsequently used in various cell transduction experiments described in Example 3 below.

In these experiments, primary CD4$^+$ and CD8$^+$ T cells were isolated from blood after apheresis and enriched by negative selection using human T cell isolation kits (human CD4$^+$ or CD8$^+$ enrichment cocktail; STEMCELL Technologies Cat #15062 and 15063). Blood was obtained from Blood Centers of the Pacific (San Francisco, CA) as approved by the University Institutional Review Board. T cells were cryopreserved in growth medium (RPMI-1640, UCSF cell culture core) with 20% human AB serum (Valley Biomedical Inc., #HP1022) and 10% DMSO. After thawing, T cells were cultured in human T cell medium containing X-VIVO™ 15 (Lonza #04-418Q), 5% Human AB serum and 10 mM neutralized N-acetyl L-Cysteine (Sigma-Aldrich #A9165) supplemented with 30 units/mL IL-2 (NCI BRB Preclinical Repository) for all experiments.

Example 3

Human T Cells were Stably Transduced with Lentiviral Vectors

This Example describes a general protocol used for lentiviral transduction of human T cells.

Generally, lentiviral vectors pseudo-typed with vesicular stomatitis virus envelope G protein (VSV-G) (pantropic vectors) were produced via transfection of Lenti-X™ 293T cells (Clontech #11131D) with a pHR' SIN:CSW transgene expression vector and the viral packaging plasmids pCMVdR8.91 and pMD2.G using Minis TransIT®-Lenti (Mirus, #MIR 6606). Generally, primary T cells were thawed the same day and, after 24 hours in culture, were stimulated with beads having anti-CD3 and anti-CD28 antibodies bound to the surface (Human T-Activator CD3/CD28 Dynabeads®, Life Technologies #11131D) at a 1:3 cell:bead ratio. At 48 hours, viral supernatant was harvested and the primary T cells were exposed to the virus for 24 hours. At Day 5 post T cell stimulation, the beads were removed, and the T cells expanded until Day 14 when they were rested and could be used in assays. T cells were sorted for assays with a Beckton Dickinson (BD) FACSAria™ II flow cytometer.

Example 4

Cancer Cell Lines

The cancer cell lines used were K562 myelogenous leukemia cells (ATCC #CCL-243). K562 cells were lentivirally transduced to stably express human CD19 at equivalent levels as Daudi tumors. CD19 levels were determined by staining the cells with α-CD19 APC (Biolegend #302212). All cell lines were sorted for expression of the transgene.

Example 5

Stimulation of Primary T Cells In Vitro

This Example describes experiments performed to demonstrate the stimulation of primary T cells in vitro by the chimeric humanized HingeNotch polypeptides described herein.

For all in vitro T cell stimulations, $1\times10^5$ T cells were co-cultured with sender cells at a 1:1 ratio in flat bottom 96-well tissue culture plates. The cultures were analyzed at 24, 48, or 72 hours for reporter activation with a BD Fortessa™ X-50. All flow cytometry analysis was performed in FlowJo™ software (TreeStar, Inc.).

Example 6

Activation Profile of Primary Human CD4+ T Cells in the Absence of a Receptor Gene This Example describes experiments performed to evaluate the activation profile of primary human CD4+ T cells containing a (4×)HNF1α-response element reporter or a (4×)Pax6-response element reporter in the absence of a receptor to activate it.

Figure 12:
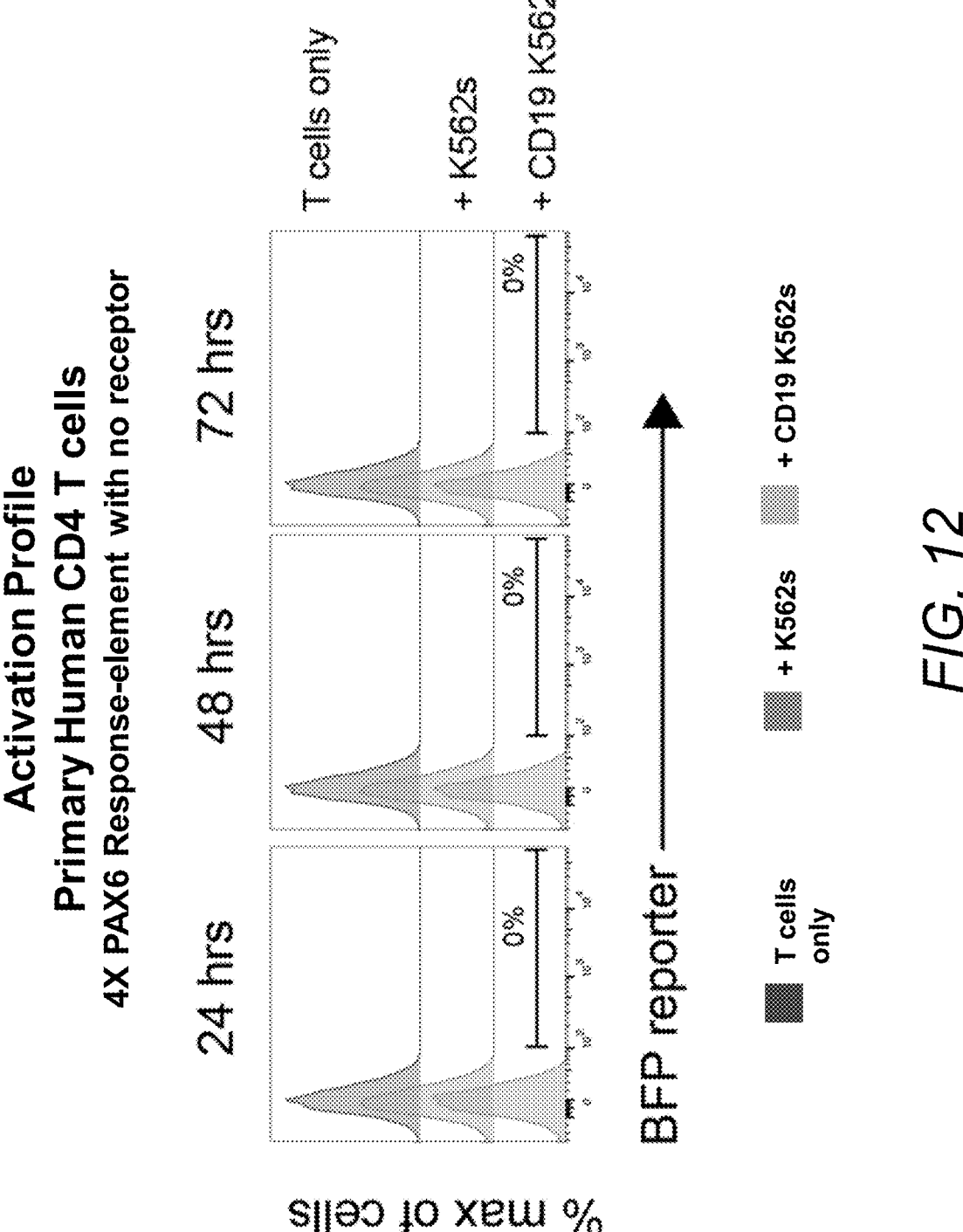
FIG. 12 schematically summarizes the results of experiments performed to evaluate the activation profile of primary human CD4+ T cells containing (4×)Pax6-response element reporter in the absence of an activating receptor. In these experiments, activation over a 72-hr period of primary human CD4+ T cells containing the (4×)Pax6-response element reporter. Approximately $1 \times 10^5$ T cells were cultured alone (upper trace), with $1 \times 10^5$ K562 cells (middle trace), or with $1 \times 10^5$ CD19$^+$ K562 cells (lower trace) for 24, 48 or 72 hours, and transcriptional activation of an inducible BFP reporter was measured using a Fortessa X-50 (BD). Percent cells activated by CD19$^+$ K562s (lower trace % s) is indicated.

In these experiments, activation over a 72-hr period of primary human CD4+ T cells containing a (4×)HNF1α-response element reporter (FIG. 2) or the (4×)Pax6-response element reporter (FIG. 12). Approximately $1\times10^5$ T cells were cultured alone (upper trace), with $1\times10^5$ K562 cells (middle trace), or with $1\times10^5$ CD19$^+$ K562 cells (lower trace) for 24, 48 or 72 hours, and transcriptional activation of an inducible BFP reporter was measured using a Fortessa X-50 (BD). Percent cells activated by CD19$^+$ K562s (lower trace % s) is indicated. This experiment demonstrates that the reporter construct is not activated by CD19 or K562 cells in the absence of the humanized HingeNotch receptor.

Example 7

Humanized HingeNotch Receptor Activation in Primary CD4+ T Cells

This Example describes the results of experiments performed to demonstrate gene activation mediated by certain novel humanized HingeNotch receptors described herein in primary CD4$^+$ cells. These experiments were conducted using ten (10) exemplary humanized HingeNotch receptors: pRay240, pRay242, pRay243, pRay244, pRay250, pRay251, pRay252, pRay253, pRay254, pRay255. As controls, a humanized MiniNotch (pRay239) and a humanized RoboNotch were tested in the same conditions. A brief description for each of the chimeric Notch receptors, their corresponding components, as well as corresponding sequence identifiers as set forth in the Sequence Listing are provided in Table 1. In these experiments, approximately $1\times10^5$ double positive T cells expressing anti-CD19 receptors and response vectors were cultured alone (upper trace), with $1\times10^5$ K562 cells (middle trace), or with $1\times10^5$ CD19+ K562 cells (lower trace) for 24, 48 or 72 hours. Transcriptional activation of an inducible BFP reporter was measured using a Fortessa X-50 (BD). Percent cells activated by CD19+K562s (lower % s) was indicated. As shown in FIGS. 3-11, the expression of the reporter gene BFP was found activated by six humanized HingeNotch receptors containing a DNA-binding domain derived from human HNF1α (pRay240, pRay243, pRay244, pRay250, pRay251, and pRay252), but only when contacted with CD19+ target cells. In contrast, MiniNotch (pRay239) and RoboNotch (pRay241) receptors exhibited high degrees of constitutive activation (not "switch-like") when used with the ICD of the present disclosure. The humanized HingeNotch receptors, pRay240, pRay243, pRay244, pRay250, pRay251, and pRay252, differ primarily in the length of the intracellular sequence between the STS and the HNF1A-based transcriptional regulatory region, and show a trend toward increased expression with reduced length.

Figures 13A, 13B:
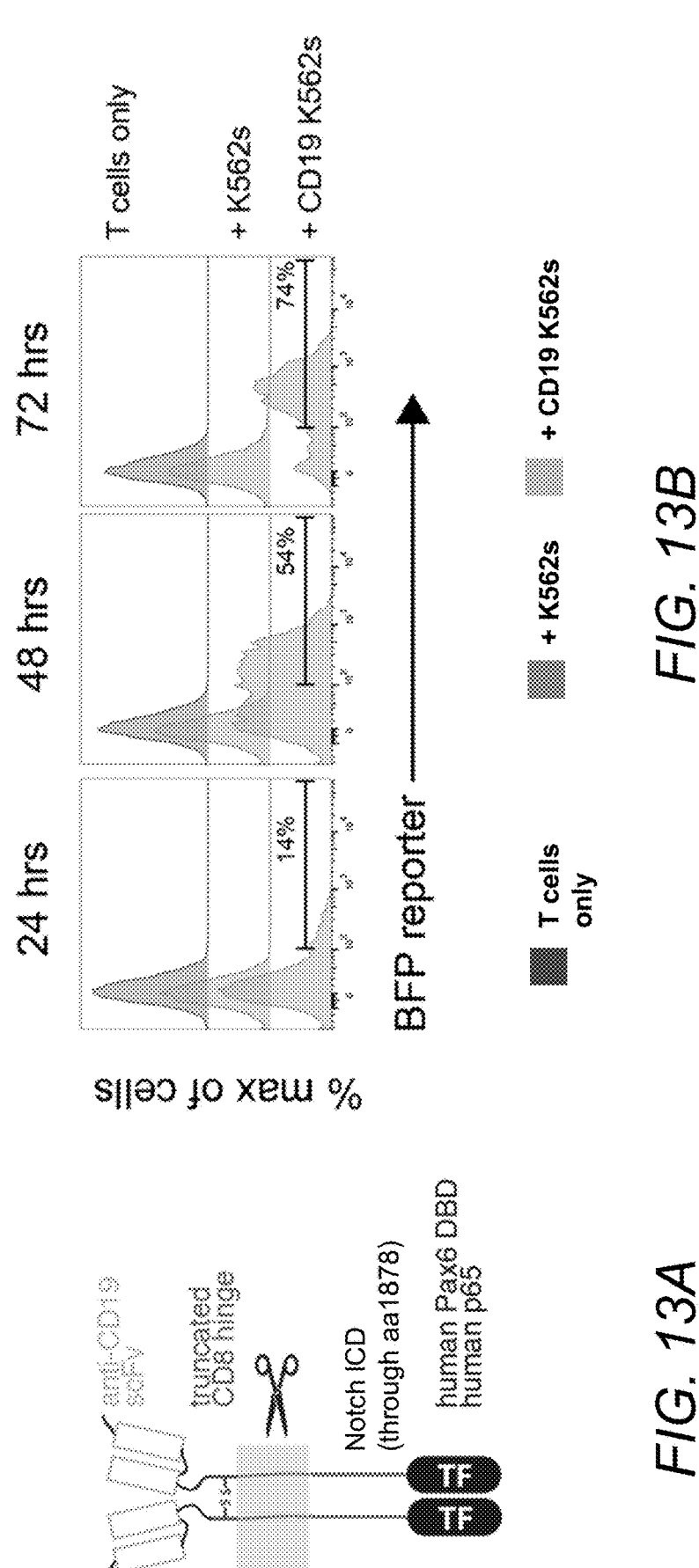
FIGS. 13A-13B schematically summarize the results from experiments performed to assess functionality of pRay253, another exemplary humanized "HingeNotch" receptor according to some embodiments of the disclosure.
Figures 14A, 14B:
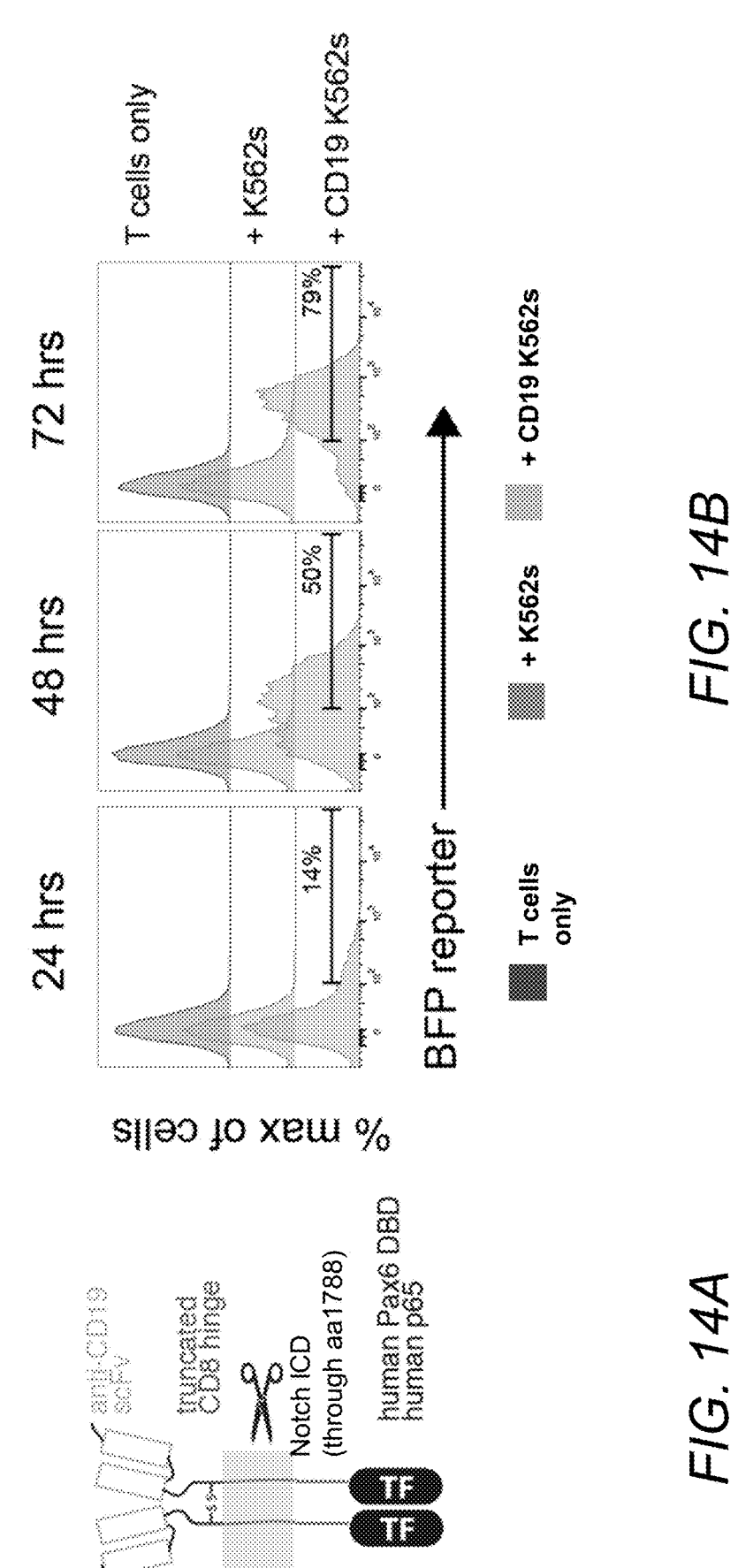
FIGS. 14A-14B schematically summarize the results from experiments performed to assess functionality of pRay254, another exemplary humanized "HingeNotch" receptor according to some embodiments of the disclosure.
Figures 15A, 15B:
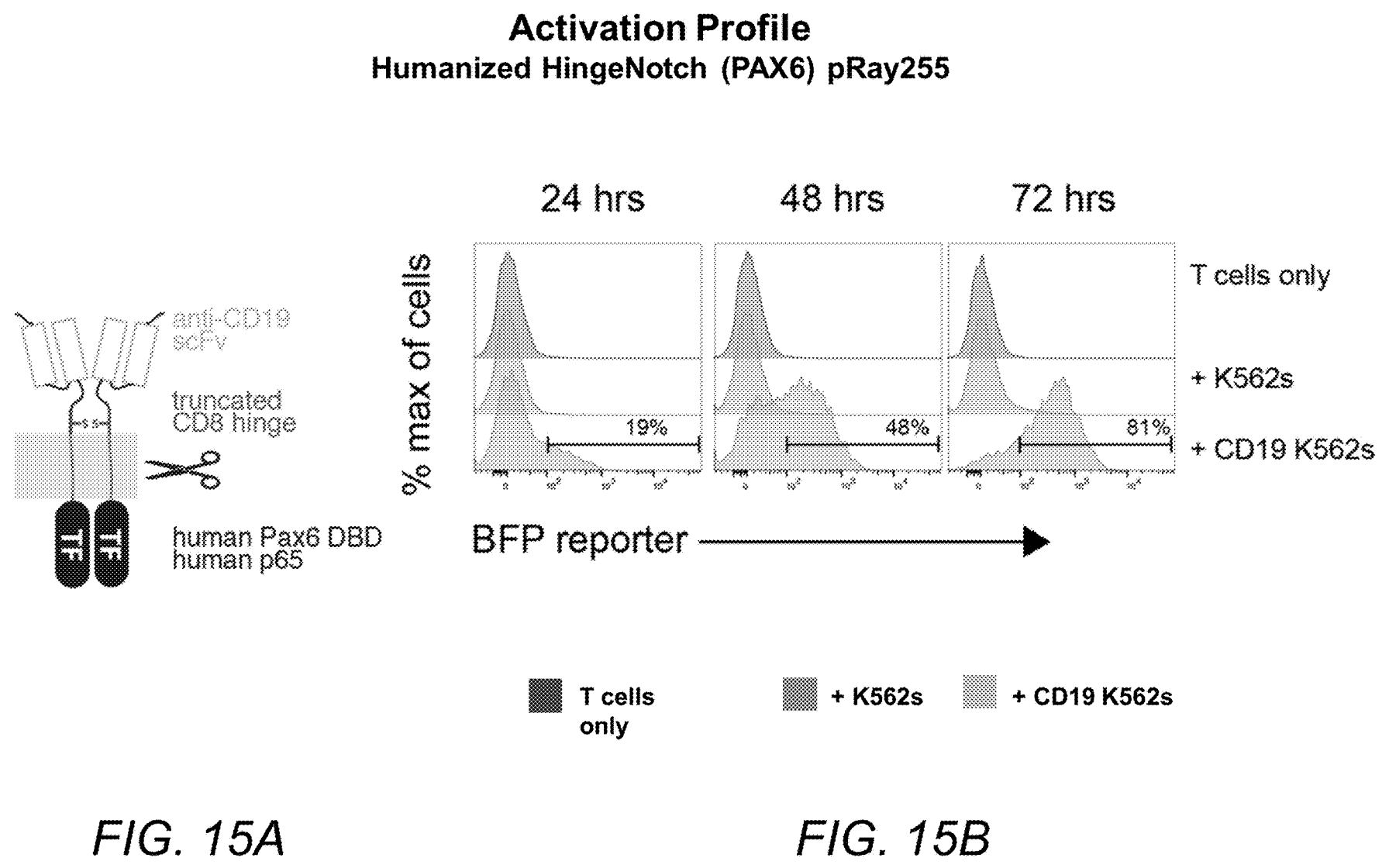

Similarly, as shown in FIGS. 13-15, the expression of the reporter gene BFP was found activated by all three humanized HingeNotch receptors containing a DNA-binding domain derived from human Pax6, but only when contacted with CD19+ target cells. These constructs, pRay253, pRay254, and pRay255, also differ primarily in the length of the intracellular sequence between the STS and the Pax6-based transcriptional regulatory region, but do not demonstrate a sensitivity to changes in length.

Example 8

Generation of Reporter Jurkat T Cells

This Example describes the generation of reporter Jurkat T cells that were subsequently used for the testing of humanized HingeNotch receptors described herein.

In these experiments, E6-1 Jurkat T cells (ATCC # TIB-152) were lentivirally transduced with a reporter plasmid carrying an inducible BFP reporter gene and/or a constitutive mCitrine reporter gene, as described previously (K. T. Roybal et al., *Cell,* 164:1-10, 2016), with the exception that the reporter plasmid used in these experiments also contained response elements corresponding to the receptors being tested here. Lentiviral particles were produced with the receptor transgene expression vector as described previously (L. Morsut et al., *Cell* (2016) 164:780-91). Reporter-positive Jurkat cells were transduced with individual receptors and expanded for experimentation in 96 well plates. Reporter-positive Jurkat cells were sorted for mCitrine expression using a Beckton Dickinson (BD) FACSAria™ II flow cytometer and expanded.

Example 9

Stimulation of Jurkat T Cells In Vitro

This Example describes experiments performed to demonstrate the stimulation of Jurkat T cells in vitro by the humanized HingeNotch polypeptides described herein.

For all in vitro Jurkat T stimulations, $1 \times 10^5$ Jurkat T cells were co-cultured with sender cells at a 1:1 ratio in flat bottom 96-well tissue culture plates. The cultures were analyzed at 24, 24, or 72 hours for reporter activation with a BD Fortessa™ X-50. All flow cytometry analysis was performed in FlowJo™ software (TreeStar, Inc.).

Example 10

Xenograft Tumor Models

NOD.Cg-Prkdc$^{scid}$Il2rg$^{tm1\,Wjl}$/SzJ (NSG) mice were implanted with $1 \times 10^6$ K562-BCMA/CD19 tumor cells subcutaneously on the left flank and with $1 \times 10^6$ K562-BCMA tumor cells on the right flank. Four days after tumor implantation, $3 \times 10^6$ engineered primary human CD4$^+$ and CD8$^+$ T cells (total of $6 \times 10^6$ T cells) were infused i.v. through tail vein injection. Tumor size was monitored via caliper 2-3 per week and mice were determined to have reached endpoint when tumors measured ≥20 mm.

Example 11

Target Cell Killing by Lentiviral Vector Constructs Containing Humanized HingeNotch Receptors and Induced BCMA-CAR Circuits This Example describes experiments performed to demonstrate that humanized HingeNotch receptors of the disclosure can target cell killing and induce BCMA-CAR circuits.

Figures 16A, 16B:
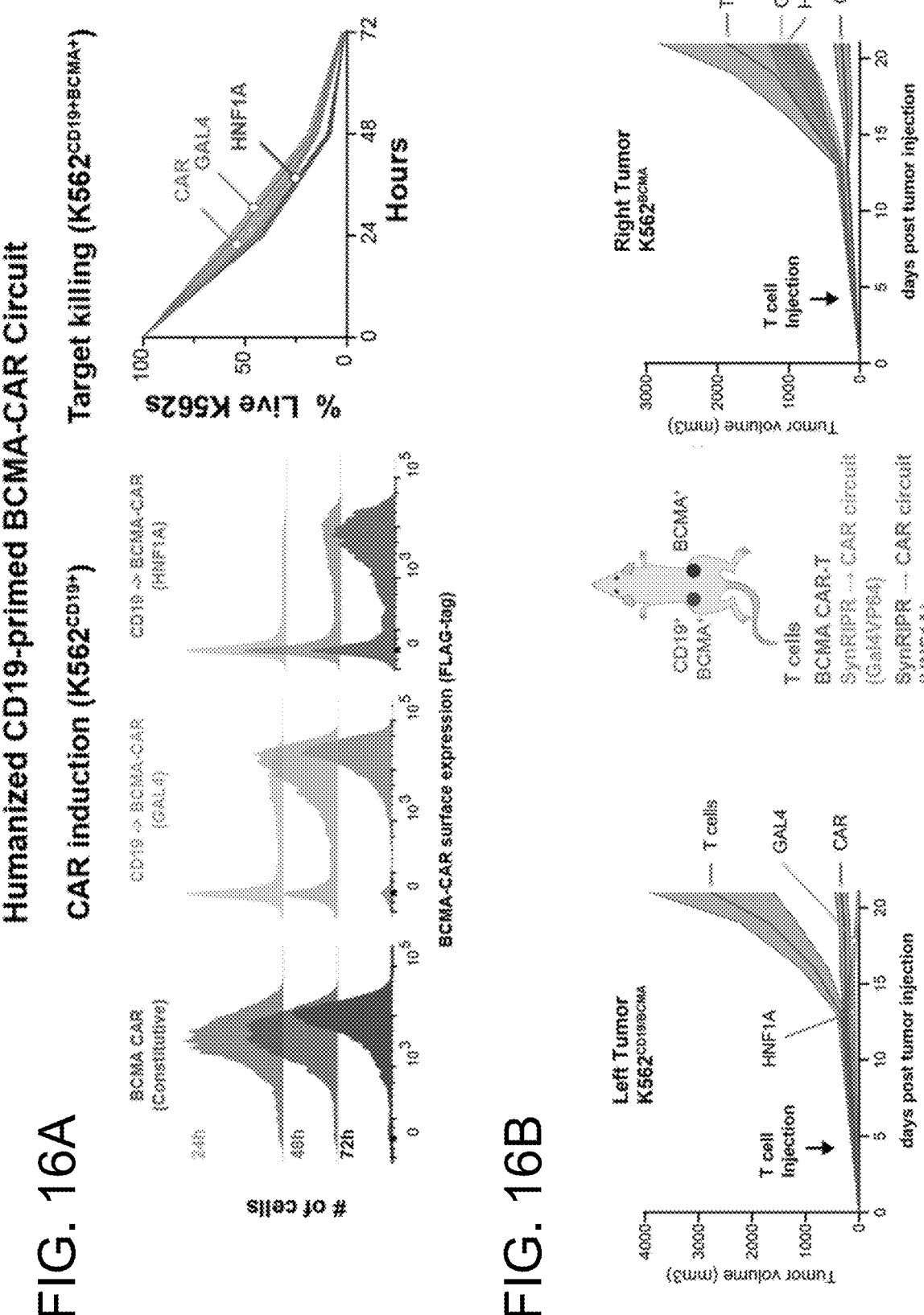
FIG. 16A schematically summarize the results from experiments performed to illustrate that a dual vector circuit made up of a humanized HingeNotch receptor using the HNF1A transcription factor (pRay240) and a response element driving a BCMA-CAR payload can induce the expression of the CAR (in the presence of CD19 only) to levels matching that of a constitutively expressed CAR driven from an silencing-prone spleen focus forming virus (SFFV) promoter. These experiments show target cell killing by lentiviral vector constructs containing humanized HingeNotch receptors and induced BCMA-CAR circuits. Primary human T-cells were activated with anti-CD3/anti-CD28 Dynabeads (Gibco) and transduced with lentiviral constructs expressing a full-humanized HingeNotch receptor (HNF1A) and a lentiviral vector with an inducible anti-BCMA-CAR cassette downstream HNF1A response elements and a minimal promoter. Cells were sorted for humanized HingeNotch receptor expression via myc-tag on Day 5 post initial T-cell stimulation and expanded further for activation testing, alongside a constitutively-expressed anti-BCMA CAR and non-humanized Gal4-based HingeNotch receptor circuit as controls. For testing, $1\times10^5$ T-cells were co-cultured with $1\times10^5$ CD19+K562 cells (left panels) or $1\times10^5$ BCMA+CD19+K562 cells (right panels). CAR induction was assessed by staining of the FLAG-tagged anti-BCMA CAR (left panels). Target cell killing was assessed over 72 hours by DRAQ7 staining and flow cytometry with a Fortessa X-50 (BD) (right panel). Fully humanized HingeNotch circuits effectively cleared target cells about as efficiently as CAR or Gal4VP64-based circuits.
FIG. 16B describes an in vivo experiment that the fully humanized receptor circuit can effectively and specifically clear tumors in a dual-antigen model, thus offering a non-immunogenic solution for specific targeting of tumors. In these experiments, NOD.Cg-Prkdc$^{scid}$Il2rg$^{tm1\,Wjl}$/SzJ (NSG) mice were implanted with $1\times10^6$ K562-BCMA/CD19 tumor cells subcutaneously on the left flank and with $1\times10^6$ K562-BCMA tumor cells on the right flank. Four days after tumor implantation, $3\times10^6$ engineered primary human CD4$^+$ and CD8$^+$ T cells (total of $6\times10^6$ T cells) were infused i.v. through tail vein injection. Tumor size was monitored via caliper 2-3 per week and mice were determined to have reached endpoint when tumors measured ≥20 mm. Fully humanized HingeNotch circuits (CD19 trigger to anti-BCMA CAR payload circuit) effectively cleared double-positive tumors and not single-positive tumors.

In these experiments, primary human T-cells were activated with anti-CD3/anti-CD28 Dynabeads (Gibco) and transduced with lentiviral constructs expressing a full-humanized HingeNotch receptor (HNF1A) and a lentiviral vector with an inducible anti-BCMA-CAR cassette downstream HNF1A response elements and a minimal promoter. Cells were sorted for humanized HingeNotch receptor expression via myc-tag on Day 5 post initial T-cell stimulation and expanded further for activation testing, alongside a constitutively-expressed anti-BCMA CAR and non-humanized Gal4-based HingeNotch receptor circuit as controls. For testing, $1 \times 10^5$ T-cells were co-cultured with $1 \times 10^5$ CD19+K562 cells (left panels) or $1 \times 10^5$ BCMA+CD19+ K562 cells (right panels). CAR induction was assessed by staining of the FLAG-tagged anti-BCMA CAR (left panels). Target cell killing was assessed over 72 hours by DRAQ7 staining and flow cytometry with a Fortessa X-50 (BD) (right panel). As shown in FIG. 16A, fully humanized HingeNotch circuits effectively cleared target cells as efficiently as CAR or Gal4VP64-based circuits In these experiments, a dual-vector circuit made up of a humanized hingeNotch receptor using the HNF1A transcription factor (pRay240) and a response element driving a BCMA-CAR payload was found to induce the expression of the CAR (in the presence of CD19 only) to levels matching that of a constitutively expressed CAR driven from an SFFV promoter. For comparison, a dual vector circuit utilizing a hingeNotch with a Gal4 instead was included, and together this shows that CAR induction by CD19+K562s by the humanized receptor seems to be slower over the time course of 3 days. This does not seem to impede the ability of the humanized receptor circuit clear target cells, however, as shown in the right panel of FIG. 16A, in which CD19/ BCMA K562s expressing both the trigger antigen (CD19) and CAR target antigen (BCMA) are cleared by the three sets of engineered CD8+ T cells (constitutive CAR-, HNF1A circuit-, and Gal4VP64 circuit) at similar rates.

FIG. 16B describes an in vivo experiment performed to demonstrate that the fully humanized receptor circuit could effectively and specifically clear tumors in a dual-antigen model, thus offering a non-immunogenic solution for specific targeting of tumors. Briefly, K562 tumors expressing both the priming and CAR target antigen (CD19, BCMA) were cleared by both the Gal4VP64 (nonhuman) and HNF1A (human) receptor circuits. To demonstrate specificity, in the same mouse, K562 tumors with just the CAR antigen (BCMA) were implanted and shown to continue growing at rates similar to control mice treated with untransduced T cells. As a control, T cells with constitutively expressed anti-BCMA CARs were shown to reduce tumor burden in both tumors. It was found that fully humanized HingeNotch circuits (CD19 trigger to anti-BCMA CAR payload circuit) effectively cleared double-positive tumors and not single-positive tumors.

Example 12

Activation Profile of Single-Vector Receptors

Figure 17:
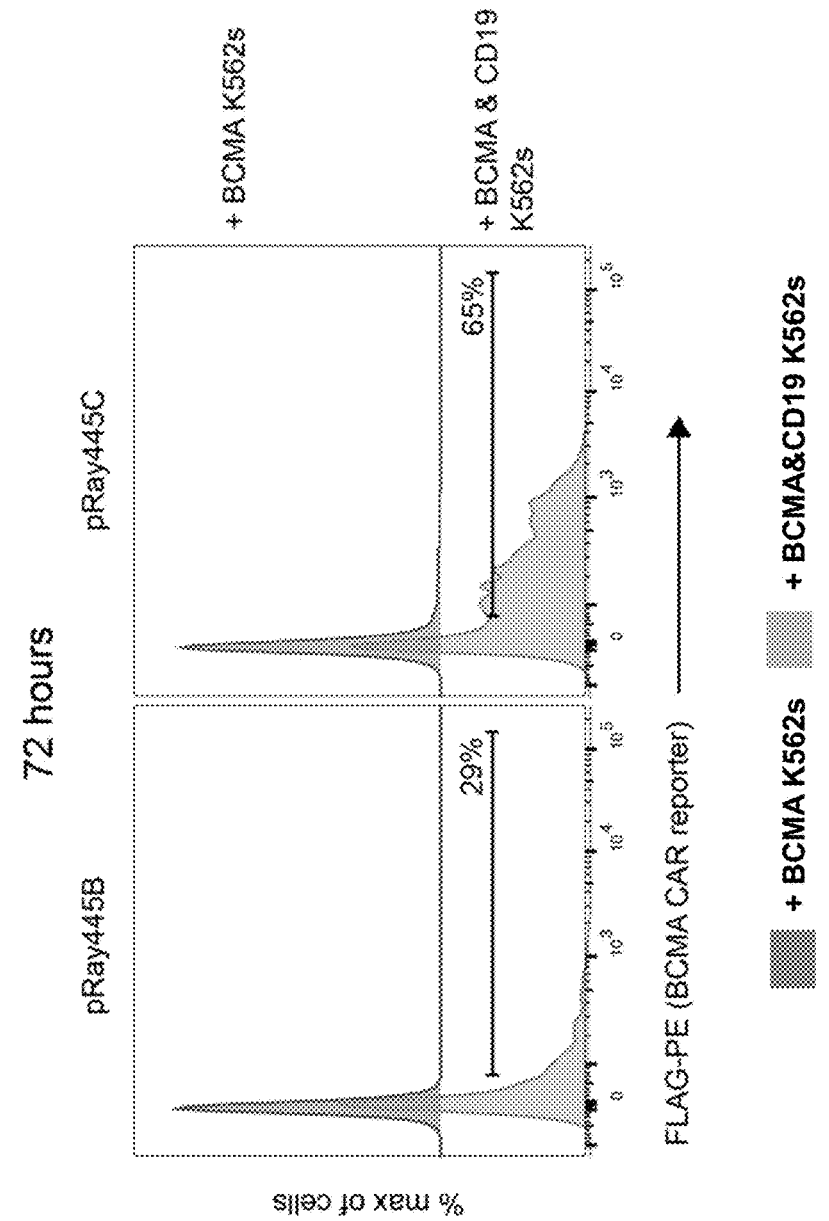
FIG. 17 schematically summarizes the results of experiments performed to illustrate receptor activation profile of single-vector receptors. $1\times10^5$ double positive T-cells expressing anti-CD19 receptors and anti-BCMA CAR response vectors were cultured with $1\times10^5$ BCMA+K562 cells (upper trace), or with $1\times10^5$ BCMA+CD19+K562 cells (lower trace) for 72 hours. Transcriptional activation of the inducible FLAG-tagged anti-BCMA CAR was measured by FLAG-PE staining on a Fortessa X-50 (BD). Percent cells activated by BCMA+CD19+K562s (lower trace % s) is displayed.

This Example describes experiments performed to demonstrate that the Pax6 based receptors of the disclosure are small enough to fit into a single lentiviral vector configuration. two fully-humanized receptor constructs are shown in FIG. 17, one with a smaller p65 TAD (pRay445B), and one with the longer p65 TAD domain (pRay451C) which showed stronger induction of a CAR payload. Without being bound to any particular theory, this single-vector design/formulation would allow such a circuit to enter current approved production pipelines for clinical applications, and also opens up the ability to utilize various delivery options such as targeted integration via CRISPR/Cas9 methods.

In these experiments, $1 \times 10^5$ double positive T-cells expressing anti-CD19 receptors and anti-BCMA CAR response vectors were cultured with $1 \times 10^5$ BCMA+K562 cells (upper trace), or with $1 \times 10^5$ BCMA+CD19+K562 cells (lower trace) for 72 hours. Transcriptional activation of the inducible FLAG-tagged anti-BCMA CAR was measured by FLAG-PE staining on a Fortessa X-50 (BD). Percent cells activated by BCMA+CD19+K562s (lower trace % s) is displayed (see, e.g., FIG. 17).

Example 13

Production of Ribonucleoprotein Complexes

This Example describes the production of ribonucleoprotein (RNP) complexes for CRISPR-mediated integration of nucleic acids encoding one or more humanized HingeNotch receptors of the disclosure.

RNPs are produced by complexing a two-component gRNA to Cas9. In these experiments, the two-component gRNA includes a crRNA and a tracrRNA, both chemically synthesized (by Dharmacon or IDT) and lyophilized. Upon arrival, lyophilized RNA is resuspended in 10 mM Tris-HCL (7.4 pH) with 150 mM KCl at a concentration of 160 µM and stored in aliquots at −80° C. Poly(L-glutamic acid) (PGA) with molecular weight (MW) of about 15-50 kDa (Sigma) is resuspended to 100 mg/mL in water, sterile filtered, and then stored in aliquots at −80° C. Cas9-NLS (QB3 Macrolab) is recombinantly produced, purified, and stored at 40 µM in 20 mM HEPES-KOH, pH 7.5, 150 mM KCl, 10% glycerol, 1 mM DTT.

To produce RNPs, the crRNA and tracrRNA aliquots are thawed, mixed 1:1 by volume, and annealed by incubation at 37° C. for 30 min to form an 80 µM gRNA solution. Subsequently, PGA is mixed with freshly-prepared gRNA at 0.8:1 volume ratio prior to complexing with Cas9 protein for final volume ratio gRNA:PGA:Cas9 of 1:0.8:1 (2:1 gRNA to Cas9 molar ratio) and incubated at 37° C. for 15 min to form a 14.3 µM RNP solution. RNPs are electroporated immediately after complexing.

Example 14

Production of Double-Strand DNA Template for Homology-Directed Repair (HDR)

This Example describes the production of donor double-strand DNA templates for CRISPR-mediated integration of the disclosed nucleic acids via homology-directed repair (HDR) pathway. In these experiments, each double-stranded homology-directed repair DNA template (HDRT) contains a novel/synthetic DNA insert flanked by homology arms. Gibson Assembly® procedures are used to construct plasmids containing the HDRT sequences and the resulting plasmids are used as templates for high-output PCR amplification (Kapa Hot Start polymerase). The resulting PCR amplicons/HDRTs are then purified using (1.0×) Beckman Coulter's solid-phase reversible immobilization (SPRI) paramagnetic bead technology and eluted into $H_2O$. The concentrations of eluted HDRTs are determined, using a 1:20 dilution, by NanoDrop and then normalized to 1 µg/µL. The size of the amplified HDRT is confirmed by gel electrophoresis in a 1.0% agarose gel.

Example 15

Electroporation of Primary T Cells

This Example describes a general protocol used for electroporation experiments of primary T cells. Generally, primary T cells are prepared and cultured as described above. After stimulation for 48-56 hours, T cells are collected from their culture vessels, and the anti-human CD3/anti-CD28 Dynabeads are magnetically separated from the T cells. Immediately before electroporation, de-beaded cells are centrifuged for 10 min at 90×g, aspirated, and resuspended in the Lonza electroporation buffer P3. Each experimental condition receives a range of 750,000-1 million activated T cells resuspended in 20 µL of P3 buffer. All electroporation experiments are carried out in 96 well format.

HDRTs are aliquoted into individual wells of a 96-well polypropylene V-bottom plate. Poly Glutamic Acid is added between the gRNA and Cas9 complexing step during RNP assembly. Complexed RNPs are then added to the HDRTs and allowed to incubate together at room temperature for at least 30s. T cells resuspended in the electroporation buffer are added to the RNP and HDRT mixture, briefly mixed, and then are transferred into a 96-well electroporation cuvette plate.

All electroporations are performed using a Lonza 4D 96-well electroporation system with pulse code EH115. Unless otherwise indicated, 3.5 µl RNPs (including 50 pmol of total RNP) are electroporated, along with 1-3 µl HDR Template at 1 µg µl-1 (1-3 µg HDR template total). Immediately after all electroporations, 80 µl of pre-warmed media (without cytokines) is added to each well, and cells are allowed to rest for 15 min at 37° C. in a cell culture incubator while remaining in the electroporation cuvettes. After 15 min, cells are moved to final culture vessels, and media supplemented with 500 U/ml IL-2 is added.

Example 16

Guide RNA Design

This Example describes the design of guide RNA (gRNA) to target the first exon of the constant chain of the TCRα gene (TRAC). The sequence targeted is located upstream of the transmembrane domain of the TCRα. This domain is required for the TCRα and β assembly and addressing to the cell-surface. Both non-homologous end joining (NHEJ) and integration of the CAR by HDR at this locus would then efficiently disrupt the TCR complex.

For the B2M, a gRNA targeting the first exon of B2M gene is designed.

```
TRAC gRNA sequence:
                                    (SEQ ID NO: 60)
5'-C*A*G*GGUUCUGGAUAUCUGUGUUUUAGAGC

UAGAAAUAGCAAGUUAAAAUAAGGCUAGUCCGUUAUCAACUUGAAAA

AGUGGCACCGAGUCGGUGCU*U*U*U-3'

B2M gRNA sequence:
                                    (SEQ ID NO: 61)
5'-G*G*C*CACGGAGCGAGACAUCUUUUUAGAGC

UAGAAAUAGCAAGUUAAAAUAAGGCUAGUCCGUUAUCAACUUGAAAA

AGUGGCACCGAGUCGGUGCU*U*U*U-3'. In this sequence, asterisk (*) represents 2'-O-methyl 3' phosphorothioate.
```

Messenger RNA

Modified guide RNAs (gRNAs) and Cas9 mRNA are synthesized by TriLink Biotechnologies. Guide RNAs were reconstituted at 1 µg/µl in cytoporation T Buffer (Harvard Apparatus).

AAV

Nucleic acids encoding a number of humanized HingeNotch receptors in accordance with some embodiments disclosed herein are cloned into a pAAV-GFP backbone (Cell Biolabs). The resulting constructs also contain a genomic sequence of the TCRα gene (TRAC) (amplified by PCR) flanking the gRNA targeting sequences.

A similar strategy is used when targeting the B2M locus, where nucleic acids encoding a number of humanized HingeNotch receptors in accordance with some embodiments disclosed herein are cloned into a pAAV-GFP backbone (Cell Biolabs). The resulting constructs also contain a genomic sequence of the B2M locus (amplified by PCR) flanking the gRNA targeting sequences.

Example 17

Gene Targeting

Forty-eight hours after initiating T cell activation, the CD3/CD28 beads are magnetically removed, and the T cells are transfected by electrotransfer of Cas9 mRNA and gRNA using an AgilePulse MAX system (Harvard Apparatus). Approximately $3\times10^6$ cells are mixed with 5 µg of Cas9 and 5 µg of gRNA into a 0.2 cm cuvette. Following electroporation, cells are diluted into culture medium and incubated at 37° C., 5% $CO_2$. Recombinant AAV6 donor vector (manufactured by SignaGen) is added to the culture 2 to 4 h after electroporation, at the indicated multiplicity of infection ($1\times10^5$ to $1\times10^6$ range). Subsequently, edited cells are cultured using standard conditions (37° C. and expanded in T cell growth medium, replenished as needed to maintain a density of ~$1\times10^6$ cells per ml every 2 to 3 days).

To obtain TCR-negative T cells, TCR-positive T cells are removed from the culture using magnetic biotin-anti-TCRαβ and anti-biotin microbeads and LS columns (Miltenyi Biotech). For whole-genome mapping of TRAC-1928z integration, the TCR-negative cell fraction was analyzed using the TLA technology (Cergentis B.V.)

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

REFERENCES

Dudani J. S., Warren A. D., and Bhatia S. N., Harnessing Protease Activity to Improve Cancer Care. Annu. Rev. Cancer Biol. 2018. 2:353-76.

David L. Porter, M. D., Bruce L. Levine, Ph.D., Michael Kalos, Ph.D., Adam Bagg, M. D., and Carl H. June, M. D. Chimeric Antigen Receptor—Modified T Cells in Chronic Lymphoid Leukemia. N. Engl J Med. 2011 Aug. 25; 365(8):725-33.

Gordon W R et al., The molecular logic of Notch signaling—a structural and biochemical perspective. J. Cell Sci. (2008) 121:3109-19.

Gordon W R et al., Mechanical Allostery: Evidence for a Force Requirement in the Proteolytic Activation of Notch. Dev Cell (2015) 33:729-36.

Morsut L, Roybal K T, Xiong X, Gordley R M, Coyle S M, Thomson M, and Lim W A. Engineering Customized Cell Sensing and Response Behaviors Using Synthetic Notch Receptors. Cell. 2016 Feb. 11; 164(4):780-91.

Naso M F, Tomkowicz B, Perry W L 3rd, Strohl W R. Adeno-Associated Virus (AAV) as a Vector for Gene Therapy. BioDrugs. 2017; 31(4):317-34.

Nasri M, Karimi A, Allahbakhshian Farsani M. Production, purification and titration of a lentivirus-based vector for gene delivery purposes. Cytotechnology. 2014; 66(6): 1031-38.

Roybal K T, Jasper Z. Williams, Leonardo Morsut, Levi J. Rupp, Isabel Kolinko, Joseph H. Choe, Whitney J. Walker, Krista A. McNally, and Wendell A. Lim. Engineering T cells with Customized Therapeutic Response Programs Using Synthetic Notch Receptors. Cell. 2016 Oct. 6; 167(2):419-32.

Samulski and Muzyczka (2014). AAV-Mediated Gene Therapy for Research and Therapeutic Purposes. Annu. Rev. Virol. 1:427.

Sakuma, et al. (2012). Lentiviral vectors: basic to translational. Biochem. J. 443:603. Watson D. J., Wolfe J. H. Viral vectors for gene therapy: methods and protocols. Totowa, NJ, USA: Humana Press; 2003. pp. 383-404.

Vidarsson G. et al., IgG subclasses and allotypes: from structure to effector functions. Frontiers Immunol. (2014) Oct. 20; 5:520.

What is claimed is:

1. A chimeric polypeptide comprising, from N-terminus to C-terminus:

a) an extracellular ligand-binding domain having a binding affinity for a ligand;

b) a hinge domain capable of promoting oligomer formation of the chimeric polypeptide via intermolecular disulfide bonding;

c) a transmembrane domain comprising one or more ligand-inducible proteolytic cleavage sites; and

d) an intracellular domain comprising a human or humanized transcriptional effector, wherein the transcriptional effector comprises: (i) a DNA-binding domain and (ii) an effector domain through which the transcriptional effector exerts its effect, wherein (i) the DNA-binding domain comprises the amino acid sequence of SEQ ID NO: 52; and (ii) the effector domain comprises the amino acid sequence of SEQ ID NO: 54;

wherein binding of the ligand to the extracellular ligand-binding domain results in cleavage at the one or more ligand-inducible proteolytic cleavage sites between the transcriptional effector and the hinge domain, and wherein the chimeric polypeptide does not comprise a LIN-12-Notch repeat (LNR) and/or a heterodimerization domain (HD) of a Notch receptor.

2. The chimeric polypeptide of claim 1, wherein the transmembrane domain further comprises a stop-transfer-sequence.

3. The chimeric polypeptide of claim 1, wherein the extracellular ligand-binding domain comprises an antigen-binding moiety capable of binding to a ligand on the surface of a cell, wherein the cell is a pathogen, a human cell, or a human tumor cell.

4. The chimeric polypeptide of claim 1, wherein the ligand:

(i) comprises a protein or a carbohydrate;

(ii) is selected from cell surface receptors, adhesion proteins, integrins, mucins, lectins, tumor associated antigens, and tumor-specific antigens; and/or (iii) is a tumor-associated antigen or a tumor-specific antigen.

5. The chimeric polypeptide of claim 1, wherein the extracellular ligand-binding domain comprises the ligand-binding portion of a receptor.

6. The chimeric polypeptide of claim 3, wherein the antigen-binding moiety:

(i) is selected from the group consisting of an antibody, a nanobody, a diabody, a triabody, a minibody, an F(ab')2 fragment, an F(ab) v fragment, a single chain variable fragment (scFv), a single domain antibody (sdAb), and a functional fragment thereof; and/or (ii) specifically binds to a tumor-associated antigen selected from the group consisting of CD19, B7H3 (CD276), BCMA (CD269), ALPPL2, CD123, CD171, CD179a, CD20, CD213A2, CD22, CD24, CD246, CD272, CD30, CD33, CD38, CD44v6, CD46, CD71, CD97, CEA, CLDN6, CLECL1, CS-1, EGFR, EGFRVIII, ELF2M, EpCAM, EphA2, Ephrin B2, FAP, FLT3, GD2, GD3, GM3, GPRC5D, HER2 (ERBB2/neu), IGLL1, IL-11Rα, KIT (CD117), MUC1, NCAM, PAP, PDGFR-β, PRSS21, PSCA, PSMA, ROR1, SIRPα, SSEA-4, TAG72, TEM1/CD248, TEM7R, TSHR, VEGFR2, ALPI, citrullinated vimentin, cMet, and Axl.

7. The chimeric polypeptide of claim 1, wherein the one or more ligand-inducible proteolytic cleavage sites comprises a γ-secretase cleavage site.

8. The chimeric polypeptide of claim 1, wherein the hinge domain is derived from a CD8α hinge domain or a functional variant of any thereof comprising an amino acid sequence having at least 80% sequence identity to SEQ ID NO: 15.

9. The chimeric polypeptide of claim 2, wherein the stop-transfer-sequence comprises an amino acid sequence having at least 80% sequence identity to any one of SEQ ID NOS: 31-51.

10. The chimeric polypeptide of claim 1, wherein the transmembrane domain comprises an amino acid sequence having at least 80% sequence identity to any one of SEQ ID NOS: 21-30.

11. The chimeric polypeptide of claim 1, wherein the domains recited in (a) through (d) are derived from human polypeptides and are substantially non-immunogenic in a human subject.

12. A recombinant nucleic acid comprising a nucleotide sequence encoding a chimeric polypeptide according claim 1.

13. A recombinant cell comprising:

a) a chimeric polypeptide according to claim 1; and/or b) a recombinant nucleic acid comprising a nucleotide sequence encoding the chimeric polypeptide of (a).

14. A pharmaceutical composition comprising a pharmaceutically acceptable carrier and one or more of the following:

a) a chimeric polypeptide according to claim 1;

b) a recombinant nucleic acid comprising a nucleotide sequence encoding the chimeric polypeptide of (a); and c) a recombinant cell comprising the chimeric polypeptide of (a) and/or the recombinant nucleic acid of (b).

15. A method for making a recombinant cell, the method comprising:

a) providing a cell capable of protein expression; and b) contacting the provided cell with a recombinant nucleic acid of claim 12.

16. A method of modulating an activity of a cell, inhibiting a target cancer cell, or treating a health condition in a subject in need thereof, the method comprising administering:

a) a chimeric polypeptide according to claim 1;

b) a recombinant nucleic acid comprising a nucleotide sequence encoding the chimeric polypeptide of (a);

c) a recombinant cell comprising the chimeric polypeptide of (a) and/or the recombinant nucleic acid of (b); or d) a pharmaceutical composition comprising a pharmaceutically acceptable carrier and one or more of the following:

(i) the chimeric polypeptide of (a), (ii) the recombinant nucleic acid of (b), and (iii) the recombinant cell of (c).

17. The chimeric polypeptide of claim 8, wherein the hinge domain comprises the amino acid sequence of SEQ ID NO: 15.

18. The chimeric polypeptide of claim 9, wherein the stop-transfer-sequence comprises the amino acid sequence of SEQ ID NO: 34.

19. The chimeric polypeptide of claim 10, wherein the transmembrane domain comprises the amino acid sequence of SEQ ID NO: 21.

20. A chimeric polypeptide comprising, from N-terminus to C-terminus:

a) an extracellular ligand-binding domain having a binding affinity for a ligand;

b) a hinge domain comprising the amino acid sequence of SEQ ID NO: 15;

c) a transmembrane domain comprising the amino acid sequence of SEQ ID NO: 21 and a stop-transfer-sequence comprising the amino acid sequence of any one of SEQ ID NO: 34; and d) an intracellular domain comprising a human or humanized transcriptional effector comprising (i) a DNA-binding domain comprising the amino acid sequence of SEQ ID NO: 52, N-terminally linked to (ii) an effector domain comprising the amino acid sequence of SEQ ID NO: 54, wherein binding of the ligand to the extracellular ligand-binding domain results in cleavage at the one or more ligand-inducible proteolytic cleavage sites between the transcriptional effector and the hinge domain, wherein the chimeric polypeptide does not comprise a LIN-12-Notch repeat (LNR) and/or a heterodimerization domain (HD) of a Notch receptor.

21. The chimeric polypeptide of claim 1, wherein the chimeric polypeptide does not comprise a LIN-12-Notch repeat (LNR) nor a heterodimerization domain (HD) of a Notch receptor.

* * * * *

SEQUENCE LISTING

```
<160> NUMBER OF SEQ ID NOS: 80

<210> SEQ ID NO 1
<211> LENGTH: 810
<212> TYPE: PRT
```

```
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: pRay239

<400> SEQUENCE: 1

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Ser Gly
    130                 135                 140

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
            195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser Ile Leu Asp Tyr Ser Phe Gly Gly Gly Ala Gly Arg Asp Ile Pro
        275                 280                 285

Pro Pro Leu Ile Glu Glu Thr Val Glu Pro Pro Pro Ala Gln Leu
    290                 295                 300

His Phe Met Tyr Val Ala Ala Ala Phe Val Leu Leu Phe Phe Val
305                 310                 315                 320

Gly Cys Gly Val Leu Leu Ser Lys Arg Lys Arg Lys His Met Val Ser
            325                 330                 335

Lys Leu Ser Gln Leu Gln Thr Glu Leu Leu Ala Ala Leu Leu Glu Ser
            340                 345                 350

Gly Leu Ser Lys Glu Ala Leu Leu Gln Ala Leu Gly Glu Pro Gly Pro
            355                 360                 365

Tyr Leu Leu Ala Gly Glu Gly Pro Leu Asp Lys Gly Glu Ser Cys Gly
```

-continued

```
          370              375              380

Gly Gly Arg Gly Glu Leu Ala Glu Leu Pro Asn Gly Leu Gly Glu Thr
385              390              395              400

Arg Gly Ser Glu Asp Glu Thr Asp Asp Asp Gly Glu Asp Phe Thr Pro
             405              410              415

Pro Ile Leu Lys Glu Leu Glu Asn Leu Ser Pro Glu Glu Ala Ala His
             420              425              430

Gln Lys Ala Val Val Glu Thr Leu Leu Gln Glu Asp Pro Trp Arg Val
         435              440              445

Ala Lys Met Val Lys Ser Tyr Leu Gln Gln His Asn Ile Pro Gln Arg
         450              455              460

Glu Val Val Asp Thr Thr Gly Leu Asn Gln Ser His Leu Ser Gln His
465              470              475              480

Leu Asn Lys Gly Thr Pro Met Lys Thr Gln Lys Arg Ala Ala Leu Tyr
             485              490              495

Thr Trp Tyr Val Arg Lys Gln Arg Glu Val Ala Gln Gln Phe Thr His
             500              505              510

Ala Gly Gln Gly Gly Leu Ile Glu Glu Pro Thr Gly Asp Glu Leu Pro
         515              520              525

Thr Lys Lys Gly Arg Arg Asn Arg Phe Lys Trp Gly Pro Ala Ser Gln
         530              535              540

Gln Ile Leu Phe Gln Ala Tyr Glu Arg Gln Lys Asn Pro Ser Lys Glu
545              550              555              560

Glu Arg Glu Thr Leu Val Glu Glu Cys Asn Arg Ala Glu Cys Ile Gln
             565              570              575

Arg Gly Val Ser Pro Ser Gln Ala Gln Gly Leu Gly Ser Asn Leu Val
             580              585              590

Thr Glu Val Arg Val Tyr Asn Trp Phe Ala Asn Arg Arg Lys Glu Glu
             595              600              605

Ala Phe Arg His Lys Leu Ala Met Thr Cys Arg Asp Glu Phe Pro Thr
             610              615              620

Met Val Phe Pro Ser Gly Gln Ile Ser Gln Ala Ser Ala Leu Ala Pro
625              630              635              640

Ala Pro Pro Gln Val Leu Pro Gln Ala Pro Ala Pro Ala Pro Ala Pro
             645              650              655

Ala Met Val Ser Ala Leu Ala Gln Ala Pro Ala Pro Val Pro Val Leu
             660              665              670

Ala Pro Gly Pro Pro Gln Ala Val Ala Pro Pro Ala Pro Lys Pro Thr
             675              680              685

Gln Ala Gly Glu Gly Thr Leu Ser Glu Ala Leu Leu Gln Leu Gln Phe
         690              695              700

Asp Asp Glu Asp Leu Gly Ala Leu Leu Gly Asn Ser Thr Asp Pro Ala
705              710              715              720

Val Phe Thr Asp Leu Ala Ser Val Asp Asn Ser Glu Phe Gln Gln Leu
             725              730              735

Leu Asn Gln Gly Ile Pro Val Ala Pro His Thr Thr Glu Pro Met Leu
             740              745              750

Met Glu Tyr Pro Glu Ala Ile Thr Arg Leu Val Thr Gly Ala Gln Arg
             755              760              765

Pro Pro Asp Pro Ala Pro Ala Pro Leu Gly Ala Pro Gly Leu Pro Asn
             770              775              780

Gly Leu Leu Ser Gly Asp Glu Asp Phe Ser Ser Ile Ala Asp Met Asp
785              790              795              800
```

-continued

```
Phe Ser Ala Leu Leu Ser Gln Ile Ser Ser
            805                 810

<210> SEQ ID NO 2
<211> LENGTH: 805
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: pRay240

<400> SEQUENCE: 2

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Phe Met Tyr Val
    290                 295                 300

Ala Ala Ala Ala Phe Val Leu Leu Phe Phe Val Gly Cys Gly Val Leu
305                 310                 315                 320

Leu Ser Lys Arg Lys Arg Lys His Met Val Ser Lys Leu Ser Gln Leu
                325                 330                 335
```

-continued

```
Gln Thr Glu Leu Leu Ala Ala Leu Leu Glu Ser Gly Leu Ser Lys Glu
            340                 345                 350

Ala Leu Leu Gln Ala Leu Gly Glu Pro Gly Pro Tyr Leu Leu Ala Gly
            355                 360                 365

Glu Gly Pro Leu Asp Lys Gly Glu Ser Cys Gly Gly Gly Arg Gly Glu
            370                 375                 380

Leu Ala Glu Leu Pro Asn Gly Leu Gly Glu Thr Arg Gly Ser Glu Asp
385                 390                 395                 400

Glu Thr Asp Asp Asp Gly Glu Asp Phe Thr Pro Pro Ile Leu Lys Glu
                    405                 410                 415

Leu Glu Asn Leu Ser Pro Glu Glu Ala Ala His Gln Lys Ala Val Val
            420                 425                 430

Glu Thr Leu Leu Gln Glu Asp Pro Trp Arg Val Ala Lys Met Val Lys
            435                 440                 445

Ser Tyr Leu Gln Gln His Asn Ile Pro Gln Arg Glu Val Val Asp Thr
            450                 455                 460

Thr Gly Leu Asn Gln Ser His Leu Ser Gln His Leu Asn Lys Gly Thr
465                 470                 475                 480

Pro Met Lys Thr Gln Lys Arg Ala Ala Leu Tyr Thr Trp Tyr Val Arg
                    485                 490                 495

Lys Gln Arg Glu Val Ala Gln Gln Phe Thr His Ala Gly Gln Gly Gly
            500                 505                 510

Leu Ile Glu Glu Pro Thr Gly Asp Glu Leu Pro Thr Lys Lys Gly Arg
            515                 520                 525

Arg Asn Arg Phe Lys Trp Gly Pro Ala Ser Gln Gln Ile Leu Phe Gln
            530                 535                 540

Ala Tyr Glu Arg Gln Lys Asn Pro Ser Lys Glu Glu Arg Glu Thr Leu
545                 550                 555                 560

Val Glu Glu Cys Asn Arg Ala Glu Cys Ile Gln Arg Gly Val Ser Pro
                    565                 570                 575

Ser Gln Ala Gln Gly Leu Gly Ser Asn Leu Val Thr Glu Val Arg Val
            580                 585                 590

Tyr Asn Trp Phe Ala Asn Arg Arg Lys Glu Glu Ala Phe Arg His Lys
            595                 600                 605

Leu Ala Met Thr Cys Arg Asp Glu Phe Pro Thr Met Val Phe Pro Ser
            610                 615                 620

Gly Gln Ile Ser Gln Ala Ser Ala Leu Ala Pro Ala Pro Gln Val
625                 630                 635                 640

Leu Pro Gln Ala Pro Ala Pro Ala Pro Ala Met Val Ser Ala
            645                 650                 655

Leu Ala Gln Ala Pro Ala Pro Val Pro Val Leu Ala Pro Gly Pro Pro
            660                 665                 670

Gln Ala Val Ala Pro Pro Ala Pro Lys Pro Thr Gln Ala Gly Glu Gly
            675                 680                 685

Thr Leu Ser Glu Ala Leu Leu Gln Leu Gln Phe Asp Asp Glu Asp Leu
            690                 695                 700

Gly Ala Leu Leu Gly Asn Ser Thr Asp Pro Ala Val Phe Thr Asp Leu
705                 710                 715                 720

Ala Ser Val Asp Asn Ser Glu Phe Gln Gln Leu Leu Asn Gln Gly Ile
                    725                 730                 735

Pro Val Ala Pro His Thr Thr Glu Pro Met Leu Met Glu Tyr Pro Glu
            740                 745                 750
```

-continued

```
Ala Ile Thr Arg Leu Val Thr Gly Ala Gln Arg Pro Pro Asp Pro Ala
        755                 760                 765

Pro Ala Pro Leu Gly Ala Pro Gly Leu Pro Asn Gly Leu Leu Ser Gly
    770                 775                 780

Asp Glu Asp Phe Ser Ser Ile Ala Asp Met Asp Phe Ser Ala Leu Leu
785                 790                 795                 800

Ser Gln Ile Ser Ser
                805

<210> SEQ ID NO 3
<211> LENGTH: 907
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: pRay241

<400> SEQUENCE: 3

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
        20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
            85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
            165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
        210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
            245                 250                 255

Ser Tyr Ala Met Asp Tyr Trp Gly Gln Gly Thr Ser Val Thr Val Ser
            260                 265                 270

Ser Lys Thr Leu Glu Glu Ala Pro Ser Ala Pro Pro Gln Gly Val Thr
        275                 280                 285
```

-continued

```
Val Ser Lys Asn Asp Gly Asn Gly Thr Ala Ile Leu Val Ser Trp Gln
    290                 295                 300

Pro Pro Pro Glu Asp Thr Gln Asn Gly Met Val Gln Glu Tyr Lys Val
305                 310                 315                 320

Trp Cys Leu Gly Asn Glu Thr Arg Tyr His Ile Asn Lys Thr Val Asp
                325                 330                 335

Gly Ser Thr Phe Ser Val Val Ile Pro Phe Leu Val Pro Gly Ile Arg
                340                 345                 350

Tyr Ser Val Glu Val Ala Ala Ser Thr Gly Ala Gly Ser Gly Val Lys
            355                 360                 365

Ser Glu Pro Gln Phe Ile Gln Leu Asp Ala His Gly Asn Pro Val Ser
    370                 375                 380

Pro Glu Asp Gln Val Ser Leu Ala Gln Gln Ile Ser Asp Val Val Lys
385                 390                 395                 400

Gln Pro Phe Met Tyr Val Ala Ala Ala Phe Val Leu Leu Phe Phe
                405                 410                 415

Val Gly Cys Gly Val Leu Leu Ser Lys Arg Lys Arg Lys His Met Val
            420                 425                 430

Ser Lys Leu Ser Gln Leu Gln Thr Glu Leu Leu Ala Ala Leu Leu Glu
    435                 440                 445

Ser Gly Leu Ser Lys Glu Ala Leu Leu Gln Ala Leu Gly Glu Pro Gly
    450                 455                 460

Pro Tyr Leu Leu Ala Gly Glu Gly Pro Leu Asp Lys Gly Glu Ser Cys
465                 470                 475                 480

Gly Gly Gly Arg Gly Glu Leu Ala Glu Leu Pro Asn Gly Leu Gly Glu
                485                 490                 495

Thr Arg Gly Ser Glu Asp Glu Thr Asp Asp Asp Gly Glu Asp Phe Thr
            500                 505                 510

Pro Pro Ile Leu Lys Glu Leu Glu Asn Leu Ser Pro Glu Glu Ala Ala
            515                 520                 525

His Gln Lys Ala Val Val Glu Thr Leu Leu Gln Glu Asp Pro Trp Arg
    530                 535                 540

Val Ala Lys Met Val Lys Ser Tyr Leu Gln Gln His Asn Ile Pro Gln
545                 550                 555                 560

Arg Glu Val Val Asp Thr Thr Gly Leu Asn Gln Ser His Leu Ser Gln
                565                 570                 575

His Leu Asn Lys Gly Thr Pro Met Lys Thr Gln Lys Arg Ala Ala Leu
            580                 585                 590

Tyr Thr Trp Tyr Val Arg Lys Gln Arg Glu Val Ala Gln Gln Phe Thr
            595                 600                 605

His Ala Gly Gln Gly Gly Leu Ile Glu Glu Pro Thr Gly Asp Glu Leu
    610                 615                 620

Pro Thr Lys Lys Gly Arg Arg Asn Arg Phe Lys Trp Gly Pro Ala Ser
625                 630                 635                 640

Gln Gln Ile Leu Phe Gln Ala Tyr Glu Arg Gln Lys Asn Pro Ser Lys
                645                 650                 655

Glu Glu Arg Glu Thr Leu Val Glu Glu Cys Asn Arg Ala Glu Cys Ile
            660                 665                 670

Gln Arg Gly Val Ser Pro Ser Gln Ala Gln Gly Leu Gly Ser Asn Leu
            675                 680                 685

Val Thr Glu Val Arg Val Tyr Asn Trp Phe Ala Asn Arg Arg Lys Glu
    690                 695                 700

Glu Ala Phe Arg His Lys Leu Ala Met Thr Cys Arg Asp Glu Phe Pro
```

-continued

```
705              710              715              720

Thr Met Val Phe Pro Ser Gly Gln Ile Ser Gln Ala Ser Ala Leu Ala
                725              730              735

Pro Ala Pro Pro Gln Val Leu Pro Gln Ala Pro Ala Pro Ala Pro Ala
            740              745              750

Pro Ala Met Val Ser Ala Leu Ala Gln Ala Pro Ala Pro Val Pro Val
            755              760              765

Leu Ala Pro Gly Pro Pro Gln Ala Val Ala Pro Pro Ala Pro Lys Pro
        770              775              780

Thr Gln Ala Gly Glu Gly Thr Leu Ser Glu Ala Leu Leu Gln Leu Gln
785              790              795              800

Phe Asp Asp Glu Asp Leu Gly Ala Leu Leu Gly Asn Ser Thr Asp Pro
                805              810              815

Ala Val Phe Thr Asp Leu Ala Ser Val Asp Asn Ser Glu Phe Gln Gln
            820              825              830

Leu Leu Asn Gln Gly Ile Pro Val Ala Pro His Thr Thr Glu Pro Met
        835              840              845

Leu Met Glu Tyr Pro Glu Ala Ile Thr Arg Leu Val Thr Gly Ala Gln
    850              855              860

Arg Pro Pro Asp Pro Ala Pro Ala Pro Leu Gly Ala Pro Gly Leu Pro
865              870              875              880

Asn Gly Leu Leu Ser Gly Asp Glu Asp Phe Ser Ser Ile Ala Asp Met
                885              890              895

Asp Phe Ser Ala Leu Leu Ser Gln Ile Ser Ser
                900              905
```

```
<210> SEQ ID NO 4
<211> LENGTH: 802
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: pRay242

<400> SEQUENCE: 4

Met Ala Leu Pro Val Thr Ala Leu Leu Leu Pro Leu Ala Leu Leu Leu
1               5               10              15

His Ala Ala Arg Pro Glu Gln Lys Leu Ile Ser Glu Glu Asp Leu Asp
                20              25              30

Ile Gln Met Thr Gln Thr Thr Ser Ser Leu Ser Ala Ser Leu Gly Asp
            35              40              45

Arg Val Thr Ile Ser Cys Arg Ala Ser Gln Asp Ile Ser Lys Tyr Leu
        50              55              60

Asn Trp Tyr Gln Gln Lys Pro Asp Gly Thr Val Lys Leu Leu Ile Tyr
65              70              75              80

His Thr Ser Arg Leu His Ser Gly Val Pro Ser Arg Phe Ser Gly Ser
                85              90              95

Gly Ser Gly Thr Asp Tyr Ser Leu Thr Ile Ser Asn Leu Glu Gln Glu
            100             105             110

Asp Ile Ala Thr Tyr Phe Cys Gln Gln Gly Asn Thr Leu Pro Tyr Thr
        115             120             125

Phe Gly Gly Gly Thr Lys Leu Glu Ile Thr Gly Gly Gly Gly Ser Gly
    130             135             140

Gly Gly Gly Ser Gly Gly Gly Gly Ser Glu Val Lys Leu Gln Glu Ser
```

-continued

```
145              150              155                160

Gly Pro Gly Leu Val Ala Pro Ser Gln Ser Leu Ser Val Thr Cys Thr
                165                170                175

Val Ser Gly Val Ser Leu Pro Asp Tyr Gly Val Ser Trp Ile Arg Gln
                180                185                190

Pro Pro Arg Lys Gly Leu Glu Trp Leu Gly Val Ile Trp Gly Ser Glu
                195                200                205

Thr Thr Tyr Tyr Asn Ser Ala Leu Lys Ser Arg Leu Thr Ile Ile Lys
        210                215                220

Asp Asn Ser Lys Ser Gln Val Phe Leu Lys Met Asn Ser Leu Gln Thr
225                230                235                240

Asp Asp Thr Ala Ile Tyr Tyr Cys Ala Lys His Tyr Tyr Tyr Gly Gly
                245                250                255

Ser Tyr Ala Met Asp Tyr Trp Gly Gln Gly Thr Ser Val Thr Val Ser
                260                265                270

Ser Thr Thr Thr Pro Ala Pro Arg Pro Pro Thr Pro Ala Pro Thr Ile
        275                280                285

Ala Ser Gln Pro Leu Ser Leu Arg Pro Glu Ala Cys Phe Met Tyr Val
        290                295                300

Ala Ala Ala Ala Phe Val Leu Leu Phe Phe Val Gly Cys Gly Val Leu
305                310                315                320

Leu Ser Lys Arg Lys Arg Lys His Asp Glu Phe Pro Thr Met Val Phe
                325                330                335

Pro Ser Gly Gln Ile Ser Gln Ala Ser Ala Leu Ala Pro Ala Pro Pro
                340                345                350

Gln Val Leu Pro Gln Ala Pro Ala Pro Ala Pro Ala Met Val
                355                360                365

Ser Ala Leu Ala Gln Ala Pro Ala Pro Val Pro Val Leu Ala Pro Gly
        370                375                380

Pro Pro Gln Ala Val Ala Pro Pro Ala Pro Lys Pro Thr Gln Ala Gly
385                390                395                400

Glu Gly Thr Leu Ser Glu Ala Leu Leu Gln Leu Gln Phe Asp Asp Glu
                405                410                415

Asp Leu Gly Ala Leu Leu Gly Asn Ser Thr Asp Pro Ala Val Phe Thr
                420                425                430

Asp Leu Ala Ser Val Asp Asn Ser Glu Phe Gln Gln Leu Leu Asn Gln
        435                440                445

Gly Ile Pro Val Ala Pro His Thr Thr Glu Pro Met Leu Met Glu Tyr
        450                455                460

Pro Glu Ala Ile Thr Arg Leu Val Thr Gly Ala Gln Arg Pro Pro Asp
465                470                475                480

Pro Ala Pro Ala Pro Leu Gly Ala Pro Gly Leu Pro Asn Gly Leu Leu
                485                490                495

Ser Gly Asp Glu Asp Phe Ser Ser Ile Ala Asp Met Asp Phe Ser Ala
                500                505                510

Leu Leu Ser Gln Ile Ser Ser Met Val Ser Lys Leu Ser Gln Leu Gln
        515                520                525

Thr Glu Leu Leu Ala Ala Leu Leu Glu Ser Gly Leu Ser Lys Glu Ala
        530                535                540

Leu Leu Gln Ala Leu Gly Glu Pro Gly Pro Tyr Leu Leu Ala Gly Glu
545                550                555                560

Gly Pro Leu Asp Lys Gly Glu Ser Cys Gly Gly Gly Arg Gly Glu Leu
                565                570                575
```

-continued

```
Ala Glu Leu Pro Asn Gly Leu Gly Glu Thr Arg Gly Ser Glu Asp Glu
            580                 585                 590

Thr Asp Asp Asp Gly Glu Asp Phe Thr Pro Pro Ile Leu Lys Glu Leu
595             600                 605

Glu Asn Leu Ser Pro Glu Glu Ala Ala His Gln Lys Ala Val Val Glu
    610                 615                 620

Thr Leu Leu Gln Glu Asp Pro Trp Arg Val Ala Lys Met Val Lys Ser
625             630                 635                 640

Tyr Leu Gln Gln His Asn Ile Pro Gln Arg Glu Val Val Asp Thr Thr
                645                 650                 655

Gly Leu Asn Gln Ser His Leu Ser Gln His Leu Asn Lys Gly Thr Pro
            660                 665                 670

Met Lys Thr Gln Lys Arg Ala Ala Leu Tyr Thr Trp Tyr Val Arg Lys
            675                 680                 685

Gln Arg Glu Val Ala Gln Gln Phe Thr His Ala Gly Gln Gly Gly Leu
    690                 695                 700

Ile Glu Glu Pro Thr Gly Asp Glu Leu Pro Thr Lys Lys Gly Arg Arg
705             710                 715                 720

Asn Arg Phe Lys Trp Gly Pro Ala Ser Gln Gln Ile Leu Phe Gln Ala
            725                 730                 735

Tyr Glu Arg Gln Lys Asn Pro Ser Lys Glu Glu Arg Glu Thr Leu Val
            740                 745                 750

Glu Glu Cys Asn Arg Ala Glu Cys Ile Gln Arg Gly Val Ser Pro Ser
    755                 760                 765

Gln Ala Gln Gly Leu Gly Ser Asn Leu Val Thr Glu Val Arg Val Tyr
    770                 775                 780

Asn Trp Phe Ala Asn Arg Arg Lys Glu Glu Ala Phe Arg His Lys Leu
785                 790                 795                 800

Ala Met
```

```
<210> SEQ ID NO 5
<211> LENGTH: 920
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: pRay243

<400> SEQUENCE: 5

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110
```

-continued

```
Asp Ile Ala Thr Tyr Phe Cys Gln Gln Gly Asn Thr Leu Pro Tyr Thr
    115                 120                 125

Phe Gly Gly Gly Thr Lys Leu Glu Ile Thr Gly Gly Gly Gly Ser Gly
    130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
                180                 185                 190

Pro Pro Arg Lys Gly Leu Glu Trp Leu Gly Val Ile Trp Gly Ser Glu
                195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
                260                 265                 270

Ser Thr Thr Thr Pro Ala Pro Arg Pro Pro Thr Pro Ala Pro Thr Ile
    275                 280                 285

Ala Ser Gln Pro Leu Ser Leu Arg Pro Glu Ala Cys Phe Met Tyr Val
    290                 295                 300

Ala Ala Ala Ala Phe Val Leu Leu Phe Phe Val Gly Cys Gly Val Leu
305                 310                 315                 320

Leu Ser Arg Lys Arg Arg Gln His Gly Gln Leu Trp Phe Pro Glu
                325                 330                 335

Gly Phe Lys Val Ser Glu Ala Ser Lys Lys Lys Arg Arg Glu Pro Leu
                340                 345                 350

Gly Glu Asp Ser Val Gly Leu Lys Pro Leu Lys Asn Ala Ser Asp Gly
                355                 360                 365

Ala Leu Met Asp Asp Asn Gln Asn Glu Trp Gly Asp Glu Asp Leu Glu
    370                 375                 380

Thr Lys Lys Phe Arg Phe Glu Glu Pro Val Val Leu Pro Asp Leu Asp
385                 390                 395                 400

Asp Gln Thr Asp His Arg Gln Trp Thr Gln Gln His Leu Asp Ala Ala
                405                 410                 415

Asp Leu Arg Met Ser Ala Met Ala Pro Thr Pro Pro Gln Gly Glu Val
                420                 425                 430

Asp Ala Asp Cys Met Asp Val Asn Val Arg Gly Met Val Ser Lys Leu
    435                 440                 445

Ser Gln Leu Gln Thr Glu Leu Leu Ala Ala Leu Leu Glu Ser Gly Leu
    450                 455                 460

Ser Lys Glu Ala Leu Leu Gln Ala Leu Gly Glu Pro Gly Pro Tyr Leu
465                 470                 475                 480

Leu Ala Gly Glu Gly Pro Leu Asp Lys Gly Glu Ser Cys Gly Gly Gly
                485                 490                 495

Arg Gly Glu Leu Ala Glu Leu Pro Asn Gly Leu Gly Glu Thr Arg Gly
                500                 505                 510

Ser Glu Asp Glu Thr Asp Asp Asp Gly Glu Asp Phe Thr Pro Pro Ile
    515                 520                 525

Leu Lys Glu Leu Glu Asn Leu Ser Pro Glu Glu Ala Ala His Gln Lys
```

-continued

```
            530                 535                 540

Ala Val Val Glu Thr Leu Leu Gln Glu Asp Pro Trp Arg Val Ala Lys
545                 550                 555                 560

Met Val Lys Ser Tyr Leu Gln Gln His Asn Ile Pro Gln Arg Glu Val
                565                 570                 575

Val Asp Thr Thr Gly Leu Asn Gln Ser His Leu Ser Gln His Leu Asn
                580                 585                 590

Lys Gly Thr Pro Met Lys Thr Gln Lys Arg Ala Ala Leu Tyr Thr Trp
                595                 600                 605

Tyr Val Arg Lys Gln Arg Glu Val Ala Gln Gln Phe Thr His Ala Gly
            610                 615                 620

Gln Gly Gly Leu Ile Glu Glu Pro Thr Gly Asp Glu Leu Pro Thr Lys
625                 630                 635                 640

Lys Gly Arg Arg Asn Arg Phe Lys Trp Gly Pro Ala Ser Gln Gln Ile
                645                 650                 655

Leu Phe Gln Ala Tyr Glu Arg Gln Lys Asn Pro Ser Lys Glu Glu Arg
                660                 665                 670

Glu Thr Leu Val Glu Glu Cys Asn Arg Ala Glu Cys Ile Gln Arg Gly
                675                 680                 685

Val Ser Pro Ser Gln Ala Gln Gly Leu Gly Ser Asn Leu Val Thr Glu
            690                 695                 700

Val Arg Val Tyr Asn Trp Phe Ala Asn Arg Arg Lys Glu Glu Ala Phe
705                 710                 715                 720

Arg His Lys Leu Ala Met Thr Cys Arg Asp Glu Phe Pro Thr Met Val
                725                 730                 735

Phe Pro Ser Gly Gln Ile Ser Gln Ala Ser Ala Leu Ala Pro Ala Pro
                740                 745                 750

Pro Gln Val Leu Pro Gln Ala Pro Ala Pro Ala Pro Ala Pro Ala Met
                755                 760                 765

Val Ser Ala Leu Ala Gln Ala Pro Ala Pro Val Pro Val Leu Ala Pro
            770                 775                 780

Gly Pro Pro Gln Ala Val Ala Pro Pro Ala Pro Lys Pro Thr Gln Ala
785                 790                 795                 800

Gly Glu Gly Thr Leu Ser Glu Ala Leu Leu Gln Leu Gln Phe Asp Asp
                805                 810                 815

Glu Asp Leu Gly Ala Leu Leu Gly Asn Ser Thr Asp Pro Ala Val Phe
                820                 825                 830

Thr Asp Leu Ala Ser Val Asp Asn Ser Glu Phe Gln Gln Leu Leu Asn
                835                 840                 845

Gln Gly Ile Pro Val Ala Pro His Thr Thr Glu Pro Met Leu Met Glu
            850                 855                 860

Tyr Pro Glu Ala Ile Thr Arg Leu Val Thr Gly Ala Gln Arg Pro Pro
865                 870                 875                 880

Asp Pro Ala Pro Ala Pro Leu Gly Ala Pro Gly Leu Pro Asn Gly Leu
                885                 890                 895

Leu Ser Gly Asp Glu Asp Phe Ser Ser Ile Ala Asp Met Asp Phe Ser
                900                 905                 910

Ala Leu Leu Ser Gln Ile Ser Ser
            915                 920

<210> SEQ ID NO 6
<211> LENGTH: 830
<212> TYPE: PRT
<213> ORGANISM: Artificial sequence
```

-continued

```
<220> FEATURE:
<223> OTHER INFORMATION: Synthetic construct
<220> FEATURE:
<221> NAME/KEY: MISC_FEATURE
<223> OTHER INFORMATION: pRay244

<400> SEQUENCE: 6

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

Ile Gln Met Thr Gln Thr Thr Ser Ser Leu Ser Ala Ser Leu Gly Asp
            35                  40                  45

Arg Val Thr Ile Ser Cys Arg Ala Ser Gln Asp Ile Ser Lys Tyr Leu
        50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
                100                 105                 110

Asp Ile Ala Thr Tyr Phe Cys Gln Gln Gly Asn Thr Leu Pro Tyr Thr
            115                 120                 125

Phe Gly Gly Gly Thr Lys Leu Glu Ile Thr Gly Gly Gly Gly Ser Gly
        130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
                180                 185                 190

Pro Pro Arg Lys Gly Leu Glu Trp Leu Gly Val Ile Trp Gly Ser Glu
            195                 200                 205

Thr Thr Tyr Tyr Asn Ser Ala Leu Lys Ser Arg Leu Thr Ile Ile Lys
        210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
                260                 265                 270

Ser Thr Thr Thr Pro Ala Pro Arg Pro Pro Thr Pro Ala Pro Thr Ile
            275                 280                 285

Ala Ser Gln Pro Leu Ser Leu Arg Pro Glu Ala Cys Phe Met Tyr Val
        290                 295                 300

Ala Ala Ala Ala Phe Val Leu Leu Phe Phe Val Gly Cys Gly Val Leu
305                 310                 315                 320

Leu Ser Arg Lys Arg Arg Arg Gln His Gly Gln Leu Trp Phe Pro Glu
                325                 330                 335

Gly Phe Lys Val Ser Glu Ala Ser Lys Lys Lys Arg Arg Glu Pro Leu
                340                 345                 350

Gly Met Val Ser Lys Leu Ser Gln Leu Gln Thr Glu Leu Leu Ala Ala
            355                 360                 365

Leu Leu Glu Ser Gly Leu Ser Lys Glu Ala Leu Leu Gln Ala Leu Gly
        370                 375                 380
```

-continued

```
Glu Pro Gly Pro Tyr Leu Leu Ala Gly Glu Gly Pro Leu Asp Lys Gly
385             390             395             400

Glu Ser Cys Gly Gly Gly Arg Gly Glu Leu Ala Glu Leu Pro Asn Gly
            405             410             415

Leu Gly Glu Thr Arg Gly Ser Glu Asp Glu Thr Asp Asp Asp Gly Glu
            420             425             430

Asp Phe Thr Pro Pro Ile Leu Lys Glu Leu Glu Asn Leu Ser Pro Glu
            435             440             445

Glu Ala Ala His Gln Lys Ala Val Val Glu Thr Leu Leu Gln Glu Asp
            450             455             460

Pro Trp Arg Val Ala Lys Met Val Lys Ser Tyr Leu Gln Gln His Asn
465             470             475             480

Ile Pro Gln Arg Glu Val Val Asp Thr Thr Gly Leu Asn Gln Ser His
            485             490             495

Leu Ser Gln His Leu Asn Lys Gly Thr Pro Met Lys Thr Gln Lys Arg
            500             505             510

Ala Ala Leu Tyr Thr Trp Tyr Val Arg Lys Gln Arg Glu Val Ala Gln
            515             520             525

Gln Phe Thr His Ala Gly Gln Gly Gly Leu Ile Glu Glu Pro Thr Gly
            530             535             540

Asp Glu Leu Pro Thr Lys Lys Gly Arg Arg Asn Arg Phe Lys Trp Gly
545             550             555             560

Pro Ala Ser Gln Gln Ile Leu Phe Gln Ala Tyr Glu Arg Gln Lys Asn
            565             570             575

Pro Ser Lys Glu Glu Arg Glu Thr Leu Val Glu Glu Cys Asn Arg Ala
            580             585             590

Glu Cys Ile Gln Arg Gly Val Ser Pro Ser Gln Ala Gln Gly Leu Gly
            595             600             605

Ser Asn Leu Val Thr Glu Val Arg Val Tyr Asn Trp Phe Ala Asn Arg
            610             615             620

Arg Lys Glu Glu Ala Phe Arg His Lys Leu Ala Met Thr Cys Arg Asp
625             630             635             640

Glu Phe Pro Thr Met Val Phe Pro Ser Gly Gln Ile Ser Gln Ala Ser
            645             650             655

Ala Leu Ala Pro Ala Pro Pro Gln Val Leu Pro Gln Ala Pro Ala Pro
            660             665             670

Ala Pro Ala Pro Ala Met Val Ser Ala Leu Ala Gln Ala Pro Ala Pro
            675             680             685

Val Pro Val Leu Ala Pro Gly Pro Pro Gln Ala Val Ala Pro Pro Ala
            690             695             700

Pro Lys Pro Thr Gln Ala Gly Glu Gly Thr Leu Ser Glu Ala Leu Leu
705             710             715             720

Gln Leu Gln Phe Asp Asp Glu Asp Leu Gly Ala Leu Leu Gly Asn Ser
            725             730             735

Thr Asp Pro Ala Val Phe Thr Asp Leu Ala Ser Val Asp Asn Ser Glu
            740             745             750

Phe Gln Gln Leu Leu Asn Gln Gly Ile Pro Val Ala Pro His Thr Thr
            755             760             765

Glu Pro Met Leu Met Glu Tyr Pro Glu Ala Ile Thr Arg Leu Val Thr
            770             775             780

Gly Ala Gln Arg Pro Pro Asp Pro Ala Pro Ala Pro Leu Gly Ala Pro
785             790             795             800
```

-continued

```
Gly Leu Pro Asn Gly Leu Leu Ser Gly Asp Glu Asp Phe Ser Ser Ile
            805             810             815

Ala Asp Met Asp Phe Ser Ala Leu Leu Ser Gln Ile Ser Ser
            820             825             830

<210> SEQ ID NO 7
<211> LENGTH: 842
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: pRay250

<400> SEQUENCE: 7

Met Ala Leu Pro Val Thr Ala Leu Leu Leu Pro Leu Ala Leu Leu Leu
1               5               10              15

His Ala Ala Arg Pro Glu Gln Lys Leu Ile Ser Glu Glu Asp Leu Asp
            20              25              30

Ile Gln Met Thr Gln Thr Thr Ser Ser Leu Ser Ala Ser Leu Gly Asp
        35              40              45

Arg Val Thr Ile Ser Cys Arg Ala Ser Gln Asp Ile Ser Lys Tyr Leu
    50              55              60

Asn Trp Tyr Gln Gln Lys Pro Asp Gly Thr Val Lys Leu Leu Ile Tyr
65              70              75              80

His Thr Ser Arg Leu His Ser Gly Val Pro Ser Arg Phe Ser Gly Ser
            85              90              95

Gly Ser Gly Thr Asp Tyr Ser Leu Thr Ile Ser Asn Leu Glu Gln Glu
            100             105             110

Asp Ile Ala Thr Tyr Phe Cys Gln Gln Gly Asn Thr Leu Pro Tyr Thr
            115             120             125

Phe Gly Gly Gly Thr Lys Leu Glu Ile Thr Gly Gly Gly Gly Ser Gly
    130             135             140

Gly Gly Gly Ser Gly Gly Gly Gly Ser Glu Val Lys Leu Gln Glu Ser
145             150             155             160

Gly Pro Gly Leu Val Ala Pro Ser Gln Ser Leu Ser Val Thr Cys Thr
            165             170             175

Val Ser Gly Val Ser Leu Pro Asp Tyr Gly Val Ser Trp Ile Arg Gln
            180             185             190

Pro Pro Arg Lys Gly Leu Glu Trp Leu Gly Val Ile Trp Gly Ser Glu
            195             200             205

Thr Thr Tyr Tyr Asn Ser Ala Leu Lys Ser Arg Leu Thr Ile Ile Lys
    210             215             220

Asp Asn Ser Lys Ser Gln Val Phe Leu Lys Met Asn Ser Leu Gln Thr
225             230             235             240

Asp Asp Thr Ala Ile Tyr Tyr Cys Ala Lys His Tyr Tyr Tyr Gly Gly
            245             250             255

Ser Tyr Ala Met Asp Tyr Trp Gly Gln Gly Thr Ser Val Thr Val Ser
            260             265             270

Ser Thr Thr Thr Pro Ala Pro Arg Pro Pro Thr Pro Ala Pro Thr Ile
            275             280             285

Ala Ser Gln Pro Leu Ser Leu Arg Pro Glu Ala Cys Phe Met Tyr Val
    290             295             300

Ala Ala Ala Ala Phe Val Leu Leu Phe Phe Val Gly Cys Gly Val Leu
305             310             315             320
```

-continued

```
Leu Ser Arg Lys Arg Arg Arg Gln His Gly Gln Leu Trp Phe Pro Glu
            325             330                 335

Gly Phe Lys Val Ser Glu Ala Ser Lys Lys Arg Arg Glu Pro Leu
            340             345             350

Gly Glu Asp Ser Val Gly Leu Lys Pro Leu Lys Asn Ala Met Val Ser
            355             360             365

Lys Leu Ser Gln Leu Gln Thr Glu Leu Leu Ala Ala Leu Leu Glu Ser
    370             375             380

Gly Leu Ser Lys Glu Ala Leu Leu Gln Ala Leu Gly Glu Pro Gly Pro
385             390             395             400

Tyr Leu Leu Ala Gly Glu Gly Pro Leu Asp Lys Gly Glu Ser Cys Gly
            405             410             415

Gly Gly Arg Gly Glu Leu Ala Glu Leu Pro Asn Gly Leu Gly Glu Thr
            420             425             430

Arg Gly Ser Glu Asp Glu Thr Asp Asp Asp Gly Glu Asp Phe Thr Pro
            435             440             445

Pro Ile Leu Lys Glu Leu Glu Asn Leu Ser Pro Glu Glu Ala Ala His
    450             455             460

Gln Lys Ala Val Val Glu Thr Leu Leu Gln Glu Asp Pro Trp Arg Val
465             470             475             480

Ala Lys Met Val Lys Ser Tyr Leu Gln Gln His Asn Ile Pro Gln Arg
            485             490             495

Glu Val Val Asp Thr Thr Gly Leu Asn Gln Ser His Leu Ser Gln His
            500             505             510

Leu Asn Lys Gly Thr Pro Met Lys Thr Gln Lys Arg Ala Ala Leu Tyr
            515             520             525

Thr Trp Tyr Val Arg Lys Gln Arg Glu Val Ala Gln Gln Phe Thr His
            530             535             540

Ala Gly Gln Gly Gly Leu Ile Glu Glu Pro Thr Gly Asp Glu Leu Pro
545             550             555             560

Thr Lys Lys Gly Arg Arg Asn Arg Phe Lys Trp Gly Pro Ala Ser Gln
            565             570             575

Gln Ile Leu Phe Gln Ala Tyr Glu Arg Gln Lys Asn Pro Ser Lys Glu
            580             585             590

Glu Arg Glu Thr Leu Val Glu Glu Cys Asn Arg Ala Glu Cys Ile Gln
            595             600             605

Arg Gly Val Ser Pro Ser Gln Ala Gln Gly Leu Gly Ser Asn Leu Val
            610             615             620

Thr Glu Val Arg Val Tyr Asn Trp Phe Ala Asn Arg Arg Lys Glu Glu
625             630             635             640

Ala Phe Arg His Lys Leu Ala Met Thr Cys Arg Asp Glu Phe Pro Thr
            645             650             655

Met Val Phe Pro Ser Gly Gln Ile Ser Gln Ala Ser Ala Leu Ala Pro
            660             665             670

Ala Pro Pro Gln Val Leu Pro Gln Ala Pro Ala Pro Ala Pro
            675             680             685

Ala Met Val Ser Ala Leu Ala Gln Ala Pro Ala Pro Val Pro Val Leu
            690             695             700

Ala Pro Gly Pro Pro Gln Ala Val Ala Pro Pro Ala Pro Lys Pro Thr
705             710             715             720

Gln Ala Gly Glu Gly Thr Leu Ser Glu Ala Leu Leu Gln Leu Gln Phe
            725             730             735

Asp Asp Glu Asp Leu Gly Ala Leu Leu Gly Asn Ser Thr Asp Pro Ala
```

-continued

```
                    740              745              750

Val Phe Thr Asp Leu Ala Ser Val Asp Asn Ser Glu Phe Gln Gln Leu
            755              760              765

Leu Asn Gln Gly Ile Pro Val Ala Pro His Thr Thr Glu Pro Met Leu
        770              775              780

Met Glu Tyr Pro Glu Ala Ile Thr Arg Leu Val Thr Gly Ala Gln Arg
785              790              795              800

Pro Pro Asp Pro Ala Pro Ala Pro Leu Gly Ala Pro Gly Leu Pro Asn
                805              810              815

Gly Leu Leu Ser Gly Asp Glu Asp Phe Ser Ser Ile Ala Asp Met Asp
            820              825              830

Phe Ser Ala Leu Leu Ser Gln Ile Ser Ser
        835              840
```

```
<210> SEQ ID NO 8
<211> LENGTH: 867
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: pRay251

<400> SEQUENCE: 8
```

```
Met Ala Leu Pro Val Thr Ala Leu Leu Leu Pro Leu Ala Leu Leu Leu
1               5               10              15

His Ala Ala Arg Pro Glu Gln Lys Leu Ile Ser Glu Glu Asp Leu Asp
            20              25              30

Ile Gln Met Thr Gln Thr Thr Ser Ser Leu Ser Ala Ser Leu Gly Asp
        35              40              45

Arg Val Thr Ile Ser Cys Arg Ala Ser Gln Asp Ile Ser Lys Tyr Leu
    50              55              60

Asn Trp Tyr Gln Gln Lys Pro Asp Gly Thr Val Lys Leu Leu Ile Tyr
65              70              75              80

His Thr Ser Arg Leu His Ser Gly Val Pro Ser Arg Phe Ser Gly Ser
            85              90              95

Gly Ser Gly Thr Asp Tyr Ser Leu Thr Ile Ser Asn Leu Glu Gln Glu
            100             105             110

Asp Ile Ala Thr Tyr Phe Cys Gln Gln Gly Asn Thr Leu Pro Tyr Thr
        115             120             125

Phe Gly Gly Gly Thr Lys Leu Glu Ile Thr Gly Gly Gly Gly Ser Gly
    130             135             140

Gly Gly Gly Ser Gly Gly Gly Gly Ser Glu Val Lys Leu Gln Glu Ser
145             150             155             160

Gly Pro Gly Leu Val Ala Pro Ser Gln Ser Leu Ser Val Thr Cys Thr
                165             170             175

Val Ser Gly Val Ser Leu Pro Asp Tyr Gly Val Ser Trp Ile Arg Gln
            180             185             190

Pro Pro Arg Lys Gly Leu Glu Trp Leu Gly Val Ile Trp Gly Ser Glu
        195             200             205

Thr Thr Tyr Tyr Asn Ser Ala Leu Lys Ser Arg Leu Thr Ile Ile Lys
        210             215             220

Asp Asn Ser Lys Ser Gln Val Phe Leu Lys Met Asn Ser Leu Gln Thr
225             230             235             240

Asp Asp Thr Ala Ile Tyr Tyr Cys Ala Lys His Tyr Tyr Tyr Gly Gly
```

-continued

```
                245                 250                 255
Ser Tyr Ala Met Asp Tyr Trp Gly Gln Gly Thr Ser Val Thr Val Ser
            260                 265                 270

Ser Thr Thr Thr Pro Ala Pro Arg Pro Pro Thr Pro Ala Pro Thr Ile
            275                 280                 285

Ala Ser Gln Pro Leu Ser Leu Arg Pro Glu Ala Cys Phe Met Tyr Val
            290                 295                 300

Ala Ala Ala Ala Phe Val Leu Leu Phe Phe Val Gly Cys Gly Val Leu
305                 310                 315                 320

Leu Ser Arg Lys Arg Arg Gln His Gly Gln Leu Trp Phe Pro Glu
                325                 330                 335

Gly Phe Lys Val Ser Glu Ala Ser Lys Lys Arg Arg Glu Pro Leu
            340                 345                 350

Gly Glu Asp Ser Val Gly Leu Lys Pro Leu Lys Asn Ala Ser Asp Gly
            355                 360                 365

Ala Leu Met Asp Asp Asn Gln Asn Glu Trp Gly Asp Glu Asp Leu Glu
            370                 375                 380

Thr Lys Lys Phe Arg Phe Met Val Ser Lys Leu Ser Gln Leu Gln Thr
385                 390                 395                 400

Glu Leu Leu Ala Ala Leu Leu Glu Ser Gly Leu Ser Lys Glu Ala Leu
                405                 410                 415

Leu Gln Ala Leu Gly Glu Pro Gly Pro Tyr Leu Leu Ala Gly Glu Gly
            420                 425                 430

Pro Leu Asp Lys Gly Glu Ser Cys Gly Gly Gly Arg Gly Glu Leu Ala
            435                 440                 445

Glu Leu Pro Asn Gly Leu Gly Glu Thr Arg Gly Ser Glu Asp Glu Thr
            450                 455                 460

Asp Asp Asp Gly Glu Asp Phe Thr Pro Pro Ile Leu Lys Glu Leu Glu
465                 470                 475                 480

Asn Leu Ser Pro Glu Glu Ala Ala His Gln Lys Ala Val Val Glu Thr
                485                 490                 495

Leu Leu Gln Glu Asp Pro Trp Arg Val Ala Lys Met Val Lys Ser Tyr
            500                 505                 510

Leu Gln Gln His Asn Ile Pro Gln Arg Glu Val Val Asp Thr Thr Gly
            515                 520                 525

Leu Asn Gln Ser His Leu Ser Gln His Leu Asn Lys Gly Thr Pro Met
            530                 535                 540

Lys Thr Gln Lys Arg Ala Ala Leu Tyr Thr Trp Tyr Val Arg Lys Gln
545                 550                 555                 560

Arg Glu Val Ala Gln Gln Phe Thr His Ala Gly Gln Gly Gly Leu Ile
                565                 570                 575

Glu Glu Pro Thr Gly Asp Glu Leu Pro Thr Lys Lys Gly Arg Arg Asn
            580                 585                 590

Arg Phe Lys Trp Gly Pro Ala Ser Gln Gln Ile Leu Phe Gln Ala Tyr
            595                 600                 605

Glu Arg Gln Lys Asn Pro Ser Lys Glu Glu Arg Glu Thr Leu Val Glu
            610                 615                 620

Glu Cys Asn Arg Ala Glu Cys Ile Gln Arg Gly Val Ser Pro Ser Gln
625                 630                 635                 640

Ala Gln Gly Leu Gly Ser Asn Leu Val Thr Glu Val Arg Val Tyr Asn
                645                 650                 655

Trp Phe Ala Asn Arg Arg Lys Glu Glu Ala Phe Arg His Lys Leu Ala
            660                 665                 670
```

-continued

```
Met Thr Cys Arg Asp Glu Phe Pro Thr Met Val Phe Pro Ser Gly Gln
        675                 680                 685

Ile Ser Gln Ala Ser Ala Leu Ala Pro Ala Pro Pro Gln Val Leu Pro
        690                 695                 700

Gln Ala Pro Ala Pro Ala Pro Ala Pro Ala Met Val Ser Ala Leu Ala
705                 710                 715                 720

Gln Ala Pro Ala Pro Val Pro Val Leu Ala Pro Gly Pro Pro Gln Ala
                725                 730                 735

Val Ala Pro Pro Ala Pro Lys Pro Thr Gln Ala Gly Glu Gly Thr Leu
                740                 745                 750

Ser Glu Ala Leu Leu Gln Leu Gln Phe Asp Asp Glu Asp Leu Gly Ala
                755                 760                 765

Leu Leu Gly Asn Ser Thr Asp Pro Ala Val Phe Thr Asp Leu Ala Ser
        770                 775                 780

Val Asp Asn Ser Glu Phe Gln Gln Leu Leu Asn Gln Gly Ile Pro Val
785                 790                 795                 800

Ala Pro His Thr Thr Glu Pro Met Leu Met Glu Tyr Pro Glu Ala Ile
                805                 810                 815

Thr Arg Leu Val Thr Gly Ala Gln Arg Pro Pro Asp Pro Ala Pro Ala
                820                 825                 830

Pro Leu Gly Ala Pro Gly Leu Pro Asn Gly Leu Leu Ser Gly Asp Glu
        835                 840                 845

Asp Phe Ser Ser Ile Ala Asp Met Asp Phe Ser Ala Leu Leu Ser Gln
        850                 855                 860

Ile Ser Ser
865

<210> SEQ ID NO 9
<211> LENGTH: 892
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: pRay252

<400> SEQUENCE: 9

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
        50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
                100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
        130                 135                 140
```

-continued

```
Gly Gly Gly Ser Gly Gly Gly Ser Glu Val Lys Leu Gln Glu Ser
145             150             155             160

Gly Pro Gly Leu Val Ala Pro Ser Gln Ser Leu Ser Val Thr Cys Thr
            165             170             175

Val Ser Gly Val Ser Leu Pro Asp Tyr Gly Val Ser Trp Ile Arg Gln
            180             185             190

Pro Pro Arg Lys Gly Leu Glu Trp Leu Gly Val Ile Trp Gly Ser Glu
            195             200             205

Thr Thr Tyr Tyr Asn Ser Ala Leu Lys Ser Arg Leu Thr Ile Ile Lys
    210             215             220

Asp Asn Ser Lys Ser Gln Val Phe Leu Lys Met Asn Ser Leu Gln Thr
225             230             235             240

Asp Asp Thr Ala Ile Tyr Tyr Cys Ala Lys His Tyr Tyr Tyr Gly Gly
            245             250             255

Ser Tyr Ala Met Asp Tyr Trp Gly Gln Gly Thr Ser Val Thr Val Ser
            260             265             270

Ser Thr Thr Thr Pro Ala Pro Arg Pro Pro Thr Pro Ala Pro Thr Ile
    275             280             285

Ala Ser Gln Pro Leu Ser Leu Arg Pro Glu Ala Cys Phe Met Tyr Val
    290             295             300

Ala Ala Ala Ala Phe Val Leu Leu Phe Phe Val Gly Cys Gly Val Leu
305             310             315             320

Leu Ser Arg Lys Arg Arg Arg Gln His Gly Gln Leu Trp Phe Pro Glu
            325             330             335

Gly Phe Lys Val Ser Glu Ala Ser Lys Lys Lys Arg Arg Glu Pro Leu
            340             345             350

Gly Glu Asp Ser Val Gly Leu Lys Pro Leu Lys Asn Ala Ser Asp Gly
            355             360             365

Ala Leu Met Asp Asp Asn Gln Asn Glu Trp Gly Asp Glu Asp Leu Glu
    370             375             380

Thr Lys Lys Phe Arg Phe Glu Glu Pro Val Val Leu Pro Asp Leu Asp
385             390             395             400

Asp Gln Thr Asp His Arg Gln Trp Thr Gln Gln His Leu Asp Ala Met
            405             410             415

Val Ser Lys Leu Ser Gln Leu Gln Thr Glu Leu Leu Ala Ala Leu Leu
            420             425             430

Glu Ser Gly Leu Ser Lys Glu Ala Leu Leu Gln Ala Leu Gly Glu Pro
            435             440             445

Gly Pro Tyr Leu Leu Ala Gly Glu Gly Pro Leu Asp Lys Gly Glu Ser
    450             455             460

Cys Gly Gly Gly Arg Gly Glu Leu Ala Glu Leu Pro Asn Gly Leu Gly
465             470             475             480

Glu Thr Arg Gly Ser Glu Asp Glu Thr Asp Asp Asp Gly Glu Asp Phe
            485             490             495

Thr Pro Pro Ile Leu Lys Glu Leu Glu Asn Leu Ser Pro Glu Glu Ala
            500             505             510

Ala His Gln Lys Ala Val Val Glu Thr Leu Leu Gln Glu Asp Pro Trp
            515             520             525

Arg Val Ala Lys Met Val Lys Ser Tyr Leu Gln Gln His Asn Ile Pro
    530             535             540

Gln Arg Glu Val Val Asp Thr Thr Gly Leu Asn Gln Ser His Leu Ser
545             550             555             560
```

-continued

```
Gln His Leu Asn Lys Gly Thr Pro Met Lys Thr Gln Lys Arg Ala Ala
                565                 570                 575

Leu Tyr Thr Trp Tyr Val Arg Lys Gln Arg Glu Val Ala Gln Gln Phe
                580                 585                 590

Thr His Ala Gly Gln Gly Gly Leu Ile Glu Glu Pro Thr Gly Asp Glu
                595                 600                 605

Leu Pro Thr Lys Lys Gly Arg Arg Asn Arg Phe Lys Trp Gly Pro Ala
            610                 615                 620

Ser Gln Gln Ile Leu Phe Gln Ala Tyr Glu Arg Gln Lys Asn Pro Ser
625                 630                 635                 640

Lys Glu Glu Arg Glu Thr Leu Val Glu Glu Cys Asn Arg Ala Glu Cys
                645                 650                 655

Ile Gln Arg Gly Val Ser Pro Ser Gln Ala Gln Gly Leu Gly Ser Asn
                660                 665                 670

Leu Val Thr Glu Val Arg Val Tyr Asn Trp Phe Ala Asn Arg Arg Lys
                675                 680                 685

Glu Glu Ala Phe Arg His Lys Leu Ala Met Thr Cys Arg Asp Glu Phe
                690                 695                 700

Pro Thr Met Val Phe Pro Ser Gly Gln Ile Ser Gln Ala Ser Ala Leu
705                 710                 715                 720

Ala Pro Ala Pro Pro Gln Val Leu Pro Gln Ala Pro Ala Pro Ala Pro
                725                 730                 735

Ala Pro Ala Met Val Ser Ala Leu Ala Gln Ala Pro Ala Pro Val Pro
                740                 745                 750

Val Leu Ala Pro Gly Pro Pro Gln Ala Val Ala Pro Pro Ala Pro Lys
                755                 760                 765

Pro Thr Gln Ala Gly Glu Gly Thr Leu Ser Glu Ala Leu Leu Gln Leu
            770                 775                 780

Gln Phe Asp Asp Glu Asp Leu Gly Ala Leu Leu Gly Asn Ser Thr Asp
785                 790                 795                 800

Pro Ala Val Phe Thr Asp Leu Ala Ser Val Asp Asn Ser Glu Phe Gln
                805                 810                 815

Gln Leu Leu Asn Gln Gly Ile Pro Val Ala Pro His Thr Thr Glu Pro
                820                 825                 830

Met Leu Met Glu Tyr Pro Glu Ala Ile Thr Arg Leu Val Thr Gly Ala
                835                 840                 845

Gln Arg Pro Pro Asp Pro Ala Pro Ala Pro Leu Gly Ala Pro Gly Leu
            850                 855                 860

Pro Asn Gly Leu Leu Ser Gly Asp Glu Asp Phe Ser Ser Ile Ala Asp
865                 870                 875                 880

Met Asp Phe Ser Ala Leu Leu Ser Gln Ile Ser Ser
                885                 890
```

<210> SEQ ID NO 10
<211> LENGTH: 706
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: pRay253

<400> SEQUENCE: 10

```
Met Ala Leu Pro Val Thr Ala Leu Leu Leu Pro Leu Ala Leu Leu Leu
1                   5                   10                  15
```

```
His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
            35                  40                  45

Arg Val Thr Ile Ser Cys Arg Ala Ser Gln Asp Ile Ser Lys Tyr Leu
        50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
            115                 120                 125

Phe Gly Gly Gly Thr Lys Leu Glu Ile Thr Gly Gly Gly Ser Gly
    130                 135                 140

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
            195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser Thr Thr Thr Pro Ala Pro Arg Pro Pro Thr Pro Ala Pro Thr Ile
            275                 280                 285

Ala Ser Gln Pro Leu Ser Leu Arg Pro Glu Ala Cys Phe Met Tyr Val
    290                 295                 300

Ala Ala Ala Ala Phe Val Leu Leu Phe Phe Val Gly Cys Gly Val Leu
305                 310                 315                 320

Leu Ser Arg Lys Arg Arg Gln His Gly Gln Leu Trp Phe Pro Glu
            325                 330                 335

Gly Phe Lys Val Ser Glu Ala Ser Lys Lys Lys Arg Arg Glu Pro Leu
            340                 345                 350

Gly Glu Asp Ser Val Gly Leu Lys Pro Leu Lys Asn Ala Ser Asp Gly
            355                 360                 365

Ala Leu Met Asp Asp Asn Gln Asn Glu Trp Gly Asp Glu Asp Leu Glu
    370                 375                 380

Thr Lys Lys Phe Arg Phe Glu Glu Pro Val Val Leu Pro Asp Leu Asp
385                 390                 395                 400

Asp Gln Thr Asp His Arg Gln Trp Thr Gln Gln His Leu Asp Ala Ala
                405                 410                 415

Asp Leu Arg Met Ser Ala Met Ala Pro Thr Pro Pro Gln Gly Glu Val
            420                 425                 430

Asp Ala Asp Cys Met Asp Val Asn Val Arg Gly Met Gln Asn Ser His
```

-continued

```
              435                 440                 445
Ser Gly Val Asn Gln Leu Gly Gly Val Phe Val Asn Gly Arg Pro Leu
    450                 455                 460

Pro Asp Ser Thr Arg Gln Lys Ile Val Glu Leu Ala His Ser Gly Ala
465                 470                 475                 480

Arg Pro Cys Asp Ile Ser Arg Ile Leu Gln Val Ser Asn Gly Cys Val
                485                 490                 495

Ser Lys Ile Leu Gly Arg Tyr Tyr Glu Thr Gly Ser Ile Arg Pro Arg
                500                 505                 510

Ala Ile Gly Gly Ser Lys Pro Arg Val Ala Thr Pro Glu Val Val Ser
                515                 520                 525

Lys Ile Ala Gln Tyr Lys Arg Glu Cys Pro Ser Ile Phe Ala Trp Glu
    530                 535                 540

Ile Arg Asp Arg Leu Leu Ser Glu Gly Val Cys Thr Asn Asp Asn Ile
545                 550                 555                 560

Pro Ser Val Ser Ser Ile Asn Arg Val Leu Arg Asn Leu Ala Ser Glu
                565                 570                 575

Lys Gln Gln Met Gly Ala Pro Thr Gln Ala Gly Glu Gly Thr Leu Ser
                580                 585                 590

Glu Ala Leu Leu Gln Leu Gln Phe Asp Asp Glu Asp Leu Gly Ala Leu
                595                 600                 605

Leu Gly Asn Ser Thr Asp Pro Ala Val Phe Thr Asp Leu Ala Ser Val
    610                 615                 620

Asp Asn Ser Glu Phe Gln Gln Leu Leu Asn Gln Gly Ile Pro Val Ala
625                 630                 635                 640

Pro His Thr Thr Glu Pro Met Leu Met Glu Tyr Pro Glu Ala Ile Thr
                645                 650                 655

Arg Leu Val Thr Gly Ala Gln Arg Pro Pro Asp Pro Ala Pro Ala Pro
                660                 665                 670

Leu Gly Ala Pro Gly Leu Pro Asn Gly Leu Leu Ser Gly Asp Glu Asp
                675                 680                 685

Phe Ser Ser Ile Ala Asp Met Asp Phe Ser Ala Leu Leu Ser Gln Ile
    690                 695                 700

Ser Ser
705
```

```
<210> SEQ ID NO 11
<211> LENGTH: 616
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: pRay254

<400> SEQUENCE: 11
```

```
Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

Ile Gln Met Thr Gln Thr Thr Ser Ser Leu Ser Ala Ser Leu Gly Asp
            35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
```

-continued

```
65                70                75                80

His Thr Ser Arg Leu His Ser Gly Val Pro Ser Arg Phe Ser Gly Ser
             85                90                95

Gly Ser Gly Thr Asp Tyr Ser Leu Thr Ile Ser Asn Leu Glu Gln Glu
             100               105               110

Asp Ile Ala Thr Tyr Phe Cys Gln Gln Gly Asn Thr Leu Pro Tyr Thr
             115               120               125

Phe Gly Gly Gly Thr Lys Leu Glu Ile Thr Gly Gly Gly Gly Ser Gly
    130               135               140

Gly Gly Gly Ser Gly Gly Gly Ser Glu Val Lys Leu Gln Glu Ser
145               150               155               160

Gly Pro Gly Leu Val Ala Pro Ser Gln Ser Leu Ser Val Thr Cys Thr
             165               170               175

Val Ser Gly Val Ser Leu Pro Asp Tyr Gly Val Ser Trp Ile Arg Gln
             180               185               190

Pro Pro Arg Lys Gly Leu Glu Trp Leu Gly Val Ile Trp Gly Ser Glu
             195               200               205

Thr Thr Tyr Tyr Asn Ser Ala Leu Lys Ser Arg Leu Thr Ile Ile Lys
    210               215               220

Asp Asn Ser Lys Ser Gln Val Phe Leu Lys Met Asn Ser Leu Gln Thr
225               230               235               240

Asp Asp Thr Ala Ile Tyr Tyr Cys Ala Lys His Tyr Tyr Tyr Gly Gly
             245               250               255

Ser Tyr Ala Met Asp Tyr Trp Gly Gln Gly Thr Ser Val Thr Val Ser
             260               265               270

Ser Thr Thr Thr Pro Ala Pro Arg Pro Pro Thr Pro Ala Pro Thr Ile
             275               280               285

Ala Ser Gln Pro Leu Ser Leu Arg Pro Glu Ala Cys Phe Met Tyr Val
    290               295               300

Ala Ala Ala Ala Phe Val Leu Leu Phe Phe Val Gly Cys Gly Val Leu
305               310               315               320

Leu Ser Arg Lys Arg Arg Arg Gln His Gly Gln Leu Trp Phe Pro Glu
             325               330               335

Gly Phe Lys Val Ser Glu Ala Ser Lys Lys Arg Arg Glu Pro Leu
             340               345               350

Gly Met Gln Asn Ser His Ser Gly Val Asn Gln Leu Gly Gly Val Phe
    355               360               365

Val Asn Gly Arg Pro Leu Pro Asp Ser Thr Arg Gln Lys Ile Val Glu
    370               375               380

Leu Ala His Ser Gly Ala Arg Pro Cys Asp Ile Ser Arg Ile Leu Gln
385               390               395               400

Val Ser Asn Gly Cys Val Ser Lys Ile Leu Gly Arg Tyr Tyr Glu Thr
             405               410               415

Gly Ser Ile Arg Pro Arg Ala Ile Gly Gly Ser Lys Pro Arg Val Ala
             420               425               430

Thr Pro Glu Val Val Ser Lys Ile Ala Gln Tyr Lys Arg Glu Cys Pro
             435               440               445

Ser Ile Phe Ala Trp Glu Ile Arg Asp Arg Leu Leu Ser Glu Gly Val
    450               455               460

Cys Thr Asn Asp Asn Ile Pro Ser Val Ser Ser Ile Asn Arg Val Leu
465               470               475               480

Arg Asn Leu Ala Ser Glu Lys Gln Gln Met Gly Ala Pro Thr Gln Ala
             485               490               495
```

```
Gly Glu Gly Thr Leu Ser Glu Ala Leu Leu Gln Leu Gln Phe Asp Asp
        500                 505                 510

Glu Asp Leu Gly Ala Leu Leu Gly Asn Ser Thr Asp Pro Ala Val Phe
        515                 520                 525

Thr Asp Leu Ala Ser Val Asp Asn Ser Glu Phe Gln Gln Leu Leu Asn
        530                 535                 540

Gln Gly Ile Pro Val Ala Pro His Thr Thr Glu Pro Met Leu Met Glu
545                 550                 555                 560

Tyr Pro Glu Ala Ile Thr Arg Leu Val Thr Gly Ala Gln Arg Pro Pro
                565                 570                 575

Asp Pro Ala Pro Ala Pro Leu Gly Ala Pro Gly Leu Pro Asn Gly Leu
                580                 585                 590

Leu Ser Gly Asp Glu Asp Phe Ser Ser Ile Ala Asp Met Asp Phe Ser
        595                 600                 605

Ala Leu Leu Ser Gln Ile Ser Ser
        610                 615

<210> SEQ ID NO 12
<211> LENGTH: 591
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: pRay255

<400> SEQUENCE: 12

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
        130                 135                 140

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
            195                 200                 205

Thr Thr Tyr Tyr Asn Ser Ala Leu Lys Ser Arg Leu Thr Ile Ile Lys
        210                 215                 220
```

-continued

```
Asp Asn Ser Lys Ser Gln Val Phe Leu Lys Met Asn Ser Leu Gln Thr
225             230                 235                 240

Asp Asp Thr Ala Ile Tyr Tyr Cys Ala Lys His Tyr Tyr Tyr Gly Gly
            245                 250                 255

Ser Tyr Ala Met Asp Tyr Trp Gly Gln Gly Thr Ser Val Thr Val Ser
            260                 265                 270

Ser Thr Thr Thr Pro Ala Pro Arg Pro Pro Thr Pro Ala Pro Thr Ile
            275                 280                 285

Ala Ser Gln Pro Leu Ser Leu Arg Pro Glu Ala Cys Phe Met Tyr Val
            290                 295                 300

Ala Ala Ala Ala Phe Val Leu Leu Phe Phe Val Gly Cys Gly Val Leu
305                 310                 315                 320

Leu Ser Lys Arg Lys Arg Lys His Met Gln Asn Ser His Ser Gly Val
                325                 330                 335

Asn Gln Leu Gly Gly Val Phe Val Asn Gly Arg Pro Leu Pro Asp Ser
            340                 345                 350

Thr Arg Gln Lys Ile Val Glu Leu Ala His Ser Gly Ala Arg Pro Cys
            355                 360                 365

Asp Ile Ser Arg Ile Leu Gln Val Ser Asn Gly Cys Val Ser Lys Ile
            370                 375                 380

Leu Gly Arg Tyr Tyr Glu Thr Gly Ser Ile Arg Pro Arg Ala Ile Gly
385                 390                 395                 400

Gly Ser Lys Pro Arg Val Ala Thr Pro Glu Val Val Ser Lys Ile Ala
                405                 410                 415

Gln Tyr Lys Arg Glu Cys Pro Ser Ile Phe Ala Trp Glu Ile Arg Asp
                420                 425                 430

Arg Leu Leu Ser Glu Gly Val Cys Thr Asn Asp Asn Ile Pro Ser Val
                435                 440                 445

Ser Ser Ile Asn Arg Val Leu Arg Asn Leu Ala Ser Glu Lys Gln Gln
            450                 455                 460

Met Gly Ala Pro Thr Gln Ala Gly Glu Gly Thr Leu Ser Glu Ala Leu
465                 470                 475                 480

Leu Gln Leu Gln Phe Asp Asp Glu Asp Leu Gly Ala Leu Leu Gly Asn
                485                 490                 495

Ser Thr Asp Pro Ala Val Phe Thr Asp Leu Ala Ser Val Asp Asn Ser
            500                 505                 510

Glu Phe Gln Gln Leu Leu Asn Gln Gly Ile Pro Val Ala Pro His Thr
            515                 520                 525

Thr Glu Pro Met Leu Met Glu Tyr Pro Glu Ala Ile Thr Arg Leu Val
            530                 535                 540

Thr Gly Ala Gln Arg Pro Pro Asp Pro Ala Pro Ala Pro Leu Gly Ala
545                 550                 555                 560

Pro Gly Leu Pro Asn Gly Leu Leu Ser Gly Asp Glu Asp Phe Ser Ser
                565                 570                 575

Ile Ala Asp Met Asp Phe Ser Ala Leu Leu Ser Gln Ile Ser Ser
                580                 585                 590
```

```
<210> SEQ ID NO 13
<211> LENGTH: 273
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
```

-continued

<223> OTHER INFORMATION: ECD Domain of SEQ ID NO: 1-12 and 65-66

<400> SEQUENCE: 13

```
Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
                100                 105                 110

Asp Ile Ala Thr Tyr Phe Cys Gln Gln Gly Asn Thr Leu Pro Tyr Thr
            115                 120                 125

Phe Gly Gly Gly Thr Lys Leu Glu Ile Thr Gly Gly Gly Gly Ser Gly
    130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
                180                 185                 190

Pro Pro Arg Lys Gly Leu Glu Trp Leu Gly Val Ile Trp Gly Ser Glu
            195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
            245                 250                 255

Ser Tyr Ala Met Asp Tyr Trp Gly Gln Gly Thr Ser Val Thr Val Ser
            260                 265                 270

Ser
```

<210> SEQ ID NO 14
<211> LENGTH: 32
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N-JMD Domain of SEQ ID NO: 1 (Notch1, Notch1)

<400> SEQUENCE: 14

```
Ile Leu Asp Tyr Ser Phe Gly Gly Gly Ala Gly Arg Asp Ile Pro Pro
1               5                   10                  15

Pro Leu Ile Glu Glu Thr Val Glu Pro Pro Pro Pro Ala Gln Leu His
            20                  25                  30
```

<210> SEQ ID NO 15
<211> LENGTH: 27

-continued

```
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N-JMD Domain of SEQ ID NOS: 2, 4-12, and 65-66
      (truncated CD8 hinge)

<400> SEQUENCE: 15

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys
            20                  25

<210> SEQ ID NO 16
<211> LENGTH: 45
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N-JMD domain (CD8 hinge)

<400> SEQUENCE: 16

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 17
<211> LENGTH: 39
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N-JMD domain (CD28 hinge)

<400> SEQUENCE: 17

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 18
<211> LENGTH: 27
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N-JMD domain (GGGGS)3, IgG4 hinge

<400> SEQUENCE: 18

Gly Gly Gly Gly Ser Gly Gly Gly Gly Ser Gly Gly Gly Gly Ser Glu
1               5                   10                  15

Ser Lys Tyr Gly Pro Pro Cys Pro Pro Cys Pro
            20                  25
```

```
<210> SEQ ID NO 19
<211> LENGTH: 186
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N-JMD domain (OX40 hinge)

<400> SEQUENCE: 19

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
                20                  25                  30

Asn Thr Val Cys Arg Pro Cys Gly Pro Gly Phe Tyr Asn Asp Val Val
                35                  40                  45

Ser Ser Lys Pro Cys Lys Pro Cys Thr Trp Cys Asn Leu Arg Ser Gly
        50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
                100                 105                 110

Cys Lys Pro Trp Thr Asn Cys Thr Leu Ala Gly Lys His Thr Leu Gln
            115                 120                 125

Pro Ala Ser Asn Ser Ser Asp Ala Ile Cys Glu Asp Arg Asp Pro Pro
        130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala
                180                 185

<210> SEQ ID NO 20
<211> LENGTH: 129
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: N-JMD Domain of SEQ ID NO: 3 (Robo1)

<400> SEQUENCE: 20

Lys Thr Leu Glu Glu Ala Pro Ser Ala Pro Pro Gln Gly Val Thr Val
1               5                   10                  15

Ser Lys Asn Asp Gly Asn Gly Thr Ala Ile Leu Val Ser Trp Gln Pro
                20                  25                  30

Pro Pro Glu Asp Thr Gln Asn Gly Met Val Gln Glu Tyr Lys Val Trp
        35                  40                  45

Cys Leu Gly Asn Glu Thr Arg Tyr His Ile Asn Lys Thr Val Asp Gly
        50                  55                  60

Ser Thr Phe Ser Val Val Ile Pro Phe Leu Val Pro Gly Ile Arg Tyr
65                  70                  75                  80

Ser Val Glu Val Ala Ala Ser Thr Gly Ala Gly Ser Gly Val Lys Ser
```

-continued

```
                        85                  90                  95
Glu Pro Gln Phe Ile Gln Leu Asp Ala His Gly Asn Pro Val Ser Pro
            100                 105                 110

Glu Asp Gln Val Ser Leu Ala Gln Gln Ile Ser Asp Val Val Lys Gln
        115                 120                 125

Pro

<210> SEQ ID NO 21
<211> LENGTH: 22
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: TMD Domain of SEQ ID NOS: 1-12 and 65-66
      (Notch1)

<400> SEQUENCE: 21

Phe Met Tyr Val Ala Ala Ala Ala Phe Val Leu Leu Phe Phe Val Gly
1               5                   10                  15

Cys Gly Val Leu Leu Ser
            20

<210> SEQ ID NO 22
<211> LENGTH: 21
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: TMD domain from CLSTN1

<400> SEQUENCE: 22

Ala Thr Val Val Ile Val Val Cys Val Ser Phe Leu Val Phe Met Ile
1               5                   10                  15

Ile Leu Gly Val Phe
            20

<210> SEQ ID NO 23
<211> LENGTH: 22
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: TMD domain from CLSTN2

<400> SEQUENCE: 23

Ile Ala Thr Val Val Ile Ile Ile Ser Val Cys Met Leu Val Phe Val
1               5                   10                  15

Val Ala Met Gly Val Tyr
            20

<210> SEQ ID NO 24
<211> LENGTH: 23
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: TMD domain from hNotch2
```

-continued

```
<400> SEQUENCE: 24

Leu Leu Tyr Leu Leu Ala Val Ala Val Val Ile Ile Leu Phe Ile Ile
1               5                   10                  15

Leu Leu Gly Val Ile Met Ala
            20

<210> SEQ ID NO 25
<211> LENGTH: 22
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: TMD domain from hNotch3

<400> SEQUENCE: 25

Leu Pro Leu Leu Val Ala Gly Ala Val Leu Leu Leu Val Ile Leu Val
1               5                   10                  15

Leu Gly Val Met Val Ala
            20

<210> SEQ ID NO 26
<211> LENGTH: 24
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: TMD domain from hNotch4

<400> SEQUENCE: 26

Pro Val Leu Cys Ser Pro Val Ala Gly Val Ile Leu Leu Ala Leu Gly
1               5                   10                  15

Ala Leu Leu Val Leu Gln Leu Ile
            20

<210> SEQ ID NO 27
<211> LENGTH: 24
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: TMD domain from Notch1 Danio rerio

<400> SEQUENCE: 27

Met Tyr Pro Met Phe Leu Val Leu Leu Ala Leu Ala Val Leu Ala Leu
1               5                   10                  15

Ala Ala Val Gly Val Val Val Ser
            20

<210> SEQ ID NO 28
<211> LENGTH: 22
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: TMD domain from Notch1_D. melanogaster

<400> SEQUENCE: 28

Val Ile Thr Gly Ile Ile Leu Val Ile Ile Ala Leu Ala Phe Phe Gly
```

-continued

```
1               5               10              15

Met Val Leu Ser Thr Gln
            20

<210> SEQ ID NO 29
<211> LENGTH: 22
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: TMD domain from Notch1_Xenopus laevis

<400> SEQUENCE: 29

Pro Met Leu Ser Met Leu Val Ile Pro Leu Leu Ile Ile Phe Val Phe
1               5               10              15

Met Met Val Ile Val Asn
            20

<210> SEQ ID NO 30
<211> LENGTH: 22
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: TMD domain from Notch1_Gallus gallus

<400> SEQUENCE: 30

Pro Met Tyr Val Val Val Ala Ala Leu Val Leu Leu Ala Phe Ile Gly
1               5               10              15

Val Gly Val Leu Val Ser
            20

<210> SEQ ID NO 31
<211> LENGTH: 6
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: ICD (STS) Domain of SEQ ID NOS: 1-4, 12, and
      65-66 (Notch2)

<400> SEQUENCE: 31

Lys Arg Lys Arg Lys His
1               5

<210> SEQ ID NO 32
<211> LENGTH: 121
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: ICD (STS) Domain of SEQ ID NOS: 5 and 10
      (Notch1; 1758-1878)

<400> SEQUENCE: 32

Arg Lys Arg Arg Arg Gln His Gly Gln Leu Trp Phe Pro Glu Gly Phe
1               5               10              15

Lys Val Ser Glu Ala Ser Lys Lys Lys Arg Arg Glu Pro Leu Gly Glu
            20              25              30
```

-continued

```
Asp Ser Val Gly Leu Lys Pro Leu Lys Asn Ala Ser Asp Gly Ala Leu
        35                  40                  45

Met Asp Asp Asn Gln Asn Glu Trp Gly Asp Glu Asp Leu Glu Thr Lys
    50                  55                  60

Lys Phe Arg Phe Glu Glu Pro Val Val Leu Pro Asp Leu Asp Asp Gln
65                  70                  75                  80

Thr Asp His Arg Gln Trp Thr Gln Gln His Leu Asp Ala Ala Asp Leu
                85                  90                  95

Arg Met Ser Ala Met Ala Pro Thr Pro Pro Gln Gly Glu Val Asp Ala
            100                 105                 110

Asp Cys Met Asp Val Asn Val Arg Gly
        115                 120

<210> SEQ ID NO 33
<211> LENGTH: 31
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: ICD (STS) Domain of SEQ ID NO: 6 and 11
      (Notch1; 1758-1788)

<400> SEQUENCE: 33

Arg Lys Arg Arg Arg Gln His Gly Gln Leu Trp Phe Pro Glu Gly Phe
1               5                   10                  15

Lys Val Ser Glu Ala Ser Lys Lys Lys Arg Arg Glu Pro Leu Gly
            20                  25                  30

<210> SEQ ID NO 34
<211> LENGTH: 43
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: ICD (STS) Domain of SEQ ID NO: 7 (Notch1;
      1758-1800)

<400> SEQUENCE: 34

Arg Lys Arg Arg Arg Gln His Gly Gln Leu Trp Phe Pro Glu Gly Phe
1               5                   10                  15

Lys Val Ser Glu Ala Ser Lys Lys Lys Arg Arg Glu Pro Leu Gly Glu
            20                  25                  30

Asp Ser Val Gly Leu Lys Pro Leu Lys Asn Ala
        35                  40

<210> SEQ ID NO 35
<211> LENGTH: 68
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: ICD (STS) Domain of SEQ ID NO: 8 (Notch1;
      1758-1825)

<400> SEQUENCE: 35

Arg Lys Arg Arg Arg Gln His Gly Gln Leu Trp Phe Pro Glu Gly Phe
1               5                   10                  15
```

-continued

```
Lys Val Ser Glu Ala Ser Lys Lys Arg Arg Glu Pro Leu Gly Glu
            20                  25                  30

Asp Ser Val Gly Leu Lys Pro Leu Lys Asn Ala Ser Asp Gly Ala Leu
            35                  40                  45

Met Asp Asp Asn Gln Asn Glu Trp Gly Asp Glu Asp Leu Glu Thr Lys
        50                  55                  60

Lys Phe Arg Phe
65

<210> SEQ ID NO 36
<211> LENGTH: 93
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: ICD (STS) Domain of SEQ ID NO: 9 (Notch1;
      1758-1850)

<400> SEQUENCE: 36

Arg Lys Arg Arg Arg Gln His Gly Gln Leu Trp Phe Pro Glu Gly Phe
1               5                   10                  15

Lys Val Ser Glu Ala Ser Lys Lys Lys Arg Arg Glu Pro Leu Gly Glu
            20                  25                  30

Asp Ser Val Gly Leu Lys Pro Leu Lys Asn Ala Ser Asp Gly Ala Leu
            35                  40                  45

Met Asp Asp Asn Gln Asn Glu Trp Gly Asp Glu Asp Leu Glu Thr Lys
        50                  55                  60

Lys Phe Arg Phe Glu Glu Pro Val Val Leu Pro Asp Leu Asp Asp Gln
65                  70                  75                  80

Thr Asp His Arg Gln Trp Thr Gln Gln His Leu Asp Ala
                85                  90

<210> SEQ ID NO 37
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Notch1 STS domain

<400> SEQUENCE: 37

Arg Lys Arg Arg Arg
1               5

<210> SEQ ID NO 38
<211> LENGTH: 4
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: CXCL16 STS domain

<400> SEQUENCE: 38

Lys Arg Arg Arg
1

<210> SEQ ID NO 39
<211> LENGTH: 7
```

-continued

```
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: DAG1 STS domain

<400> SEQUENCE: 39

Arg Lys Lys Arg Lys Gly Lys
1               5

<210> SEQ ID NO 40
<211> LENGTH: 6
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: PTPRF STS domain

<400> SEQUENCE: 40

Lys Arg Lys Arg Thr His
1               5

<210> SEQ ID NO 41
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: CDH5 STS domain

<400> SEQUENCE: 41

Arg Arg Arg Leu Arg Lys Gln Ala Arg Ala His Gly Lys
1               5                   10

<210> SEQ ID NO 42
<211> LENGTH: 8
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: KL STS domain

<400> SEQUENCE: 42

Lys Lys Gly Arg Arg Ser Tyr Lys
1               5

<210> SEQ ID NO 43
<211> LENGTH: 14
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: NRG1 STS domain

<400> SEQUENCE: 43

Lys Thr Lys Lys Gln Arg Lys Lys Leu His Asp Arg Leu Arg
1               5                   10

<210> SEQ ID NO 44
```

```
<211> LENGTH: 11
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: LRP1B STS domain

<400> SEQUENCE: 44

Lys Arg Lys Arg Arg Thr Lys Thr Ile Arg Arg
1               5                   10

<210> SEQ ID NO 45
<211> LENGTH: 14
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: JAG2 STS domain

<400> SEQUENCE: 45

Arg Lys Arg Arg Lys Glu Arg Glu Arg Ser Arg Leu Pro Arg
1               5                   10

<210> SEQ ID NO 46
<211> LENGTH: 8
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: KCNE3 STS domain

<400> SEQUENCE: 46

Arg Ser Arg Lys Val Asp Lys Arg
1               5

<210> SEQ ID NO 47
<211> LENGTH: 14
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: NRG2 STS domain

<400> SEQUENCE: 47

Lys Thr Lys Lys Gln Arg Lys Gln Met His Asn His Leu Arg
1               5                   10

<210> SEQ ID NO 48
<211> LENGTH: 10
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: PTPRK STS domain

<400> SEQUENCE: 48

Lys Lys Ser Lys Leu Ala Lys Lys Arg Lys
1               5                   10
```

-continued

```
<210> SEQ ID NO 49
<211> LENGTH: 10
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: EPHA4 STS domain

<400> SEQUENCE: 49

Arg Arg Arg Ser Lys Tyr Ser Lys Ala Lys
1               5                   10

<210> SEQ ID NO 50
<211> LENGTH: 10
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: PTPRM STS domain

<400> SEQUENCE: 50

Lys Lys Arg Lys Leu Ala Lys Lys Arg Lys
1               5                   10

<210> SEQ ID NO 51
<211> LENGTH: 7
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Notch4 STS domain

<400> SEQUENCE: 51

Arg Arg Arg Arg Arg Glu His
1               5

<210> SEQ ID NO 52
<211> LENGTH: 283
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: DBD Domain of SEQ ID NOS: 1-9 (HNF1a)

<400> SEQUENCE: 52

Met Val Ser Lys Leu Ser Gln Leu Gln Thr Glu Leu Leu Ala Ala Leu
1               5                   10                  15

Leu Glu Ser Gly Leu Ser Lys Glu Ala Leu Leu Gln Ala Leu Gly Glu
                20                  25                  30

Pro Gly Pro Tyr Leu Leu Ala Gly Glu Gly Pro Leu Asp Lys Gly Glu
            35                  40                  45

Ser Cys Gly Gly Gly Arg Gly Glu Leu Ala Glu Leu Pro Asn Gly Leu
        50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
```

-continued

```
               100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
                180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
        210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
                260                 265                 270

Lys Glu Glu Ala Phe Arg His Lys Leu Ala Met
        275                 280

<210> SEQ ID NO 53
<211> LENGTH: 139
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: DBD Domain of SEQ ID NOS: 10-12 and 65-66
      (Pax6)

<400> SEQUENCE: 53

Met Gln Asn Ser His Ser Gly Val Asn Gln Leu Gly Gly Val Phe Val
1               5                   10                  15

Asn Gly Arg Pro Leu Pro Asp Ser Thr Arg Gln Lys Ile Val Glu Leu
                20                  25                  30

Ala His Ser Gly Ala Arg Pro Cys Asp Ile Ser Arg Ile Leu Gln Val
        35                  40                  45

Ser Asn Gly Cys Val Ser Lys Ile Leu Gly Arg Tyr Tyr Glu Thr Gly
    50                  55                  60

Ser Ile Arg Pro Arg Ala Ile Gly Gly Ser Lys Pro Arg Val Ala Thr
65                  70                  75                  80

Pro Glu Val Val Ser Lys Ile Ala Gln Tyr Lys Arg Glu Cys Pro Ser
                85                  90                  95

Ile Phe Ala Trp Glu Ile Arg Asp Arg Leu Leu Ser Glu Gly Val Cys
                100                 105                 110

Thr Asn Asp Asn Ile Pro Ser Val Ser Ser Ile Asn Arg Val Leu Arg
        115                 120                 125

Asn Leu Ala Ser Glu Lys Gln Gln Met Gly Ala
        130                 135

<210> SEQ ID NO 54
<211> LENGTH: 191
```

-continued

```
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Transactivation domain of SEQ ID NOS: 1-9 and
      66

<400> SEQUENCE: 54

Asp Glu Phe Pro Thr Met Val Phe Pro Ser Gly Gln Ile Ser Gln Ala
1               5                   10                  15

Ser Ala Leu Ala Pro Ala Pro Pro Gln Val Leu Pro Gln Ala Pro Ala
                20                  25                  30

Pro Ala Pro Ala Pro Ala Met Val Ser Ala Leu Ala Gln Ala Pro Ala
            35                  40                  45

Pro Val Pro Val Leu Ala Pro Gly Pro Pro Gln Ala Val Ala Pro Pro
        50                  55                  60

Ala Pro Lys Pro Thr Gln Ala Gly Glu Gly Thr Leu Ser Glu Ala Leu
65                  70                  75                  80

Leu Gln Leu Gln Phe Asp Asp Glu Asp Leu Gly Ala Leu Leu Gly Asn
                85                  90                  95

Ser Thr Asp Pro Ala Val Phe Thr Asp Leu Ala Ser Val Asp Asn Ser
            100                 105                 110

Glu Phe Gln Gln Leu Leu Asn Gln Gly Ile Pro Val Ala Pro His Thr
        115                 120                 125

Thr Glu Pro Met Leu Met Glu Tyr Pro Glu Ala Ile Thr Arg Leu Val
        130                 135                 140

Thr Gly Ala Gln Arg Pro Pro Asp Pro Ala Pro Ala Pro Leu Gly Ala
145                 150                 155                 160

Pro Gly Leu Pro Asn Gly Leu Leu Ser Gly Asp Glu Asp Phe Ser Ser
                165                 170                 175

Ile Ala Asp Met Asp Phe Ser Ala Leu Leu Ser Gln Ile Ser Ser
            180                 185                 190

<210> SEQ ID NO 55
<211> LENGTH: 124
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Transactivation domain of SEQ ID NOS: 10-12 and
      65

<400> SEQUENCE: 55

Pro Thr Gln Ala Gly Glu Gly Thr Leu Ser Glu Ala Leu Leu Gln Leu
1               5                   10                  15

Gln Phe Asp Asp Glu Asp Leu Gly Ala Leu Leu Gly Asn Ser Thr Asp
                20                  25                  30

Pro Ala Val Phe Thr Asp Leu Ala Ser Val Asp Asn Ser Glu Phe Gln
            35                  40                  45

Gln Leu Leu Asn Gln Gly Ile Pro Val Ala Pro His Thr Thr Glu Pro
        50                  55                  60

Met Leu Met Glu Tyr Pro Glu Ala Ile Thr Arg Leu Val Thr Gly Ala
65                  70                  75                  80

Gln Arg Pro Pro Asp Pro Ala Pro Ala Pro Leu Gly Ala Pro Gly Leu
                85                  90                  95
```

```
Pro Asn Gly Leu Leu Ser Gly Asp Glu Asp Phe Ser Ser Ile Ala Asp
            100                 105                 110

Met Asp Phe Ser Ala Leu Leu Ser Gln Ile Ser Ser
        115                 120

<210> SEQ ID NO 56
<211> LENGTH: 21
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: CD8a signal sequence

<400> SEQUENCE: 56

Met Ala Leu Pro Val Thr Ala Leu Leu Leu Pro Leu Ala Leu Leu Leu
1               5                   10                  15

His Ala Ala Arg Pro
            20

<210> SEQ ID NO 57
<211> LENGTH: 10
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Myc tag

<400> SEQUENCE: 57

Glu Gln Lys Leu Ile Ser Glu Glu Asp Leu
1               5                   10

<210> SEQ ID NO 58
<211> LENGTH: 242
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: anti-CD19 scFv

<400> SEQUENCE: 58

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
```

-continued

```
        130              135              140
Thr Val Ser Gly Val Ser Leu Pro Asp Tyr Gly Val Ser Trp Ile Arg
145              150              155              160

Gln Pro Pro Arg Lys Gly Leu Glu Trp Leu Gly Val Ile Trp Gly Ser
                165              170              175

Glu Thr Thr Tyr Tyr Asn Ser Ala Leu Lys Ser Arg Leu Thr Ile Ile
            180              185              190

Lys Asp Asn Ser Lys Ser Gln Val Phe Leu Lys Met Asn Ser Leu Gln
        195              200              205

Thr Asp Asp Thr Ala Ile Tyr Tyr Cys Ala Lys His Tyr Tyr Tyr Gly
    210              215              220

Gly Ser Tyr Ala Met Asp Tyr Trp Gly Gln Gly Thr Ser Val Thr Val
225              230              235              240

Ser Ser
```

```
<210> SEQ ID NO 59
<211> LENGTH: 22
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: consensus Pax6 binding site

<400> SEQUENCE: 59

Ala Thr Thr Thr Thr Cys Ala Cys Gly Cys Ala Thr Gly Ala Gly Thr
1               5              10              15

Gly Cys Ala Cys Ala Gly
            20
```

```
<210> SEQ ID NO 60
<211> LENGTH: 249
<212> TYPE: DNA
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: 4X Pax6 Response Element

<400> SEQUENCE: 60
gggtttcgta acaatcgcat gaggattcgc aacgccttat tttcacgcat gagtgcacag      60
tcccgtctca gtaaaggtat tttcacgcat gagtgcacag aatcggactg ccttcgtaat     120
tttcacgcat gagtgcacag gtatcagtcg cctcggaaat tttcacgcat gagtgcacag     180
aacgactagt ctagagggta tataatgggg gccactagtc tactaccaga gctcatcgct     240
agcgctacc                                                             249
```

```
<210> SEQ ID NO 61
<211> LENGTH: 144
<212> TYPE: DNA
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: 4X HNF1a Response Element

<400> SEQUENCE: 61
atcgatgtta ataattaaca tatatgttaa tcattaacat atagttaatt attaaccgct      60
```

```
atgttaatga ttaacaacga ctagtctaga gggtatataa tgggggccac tagtctacta     120
ccagagctca tcgctagcgc tacc                                           144

<210> SEQ ID NO 62
<211> LENGTH: 69
<212> TYPE: RNA
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: TRAC gRNA sequence

<400> SEQUENCE: 62
cagggcggaa cggagagcag aaaagcaaga aaaaaggcag ccgacaacga aaaagggcac      60
cgagcgggc                                                            69

<210> SEQ ID NO 63
<211> LENGTH: 74
<212> TYPE: RNA
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: B2M gRNA sequence

<400> SEQUENCE: 63
ggccacggag cgagacacag agcagaaaag caagaaaaaa ggcagccgac aacgaaaaag      60
ggcaccgagc gggc                                                      74

<210> SEQ ID NO 64
<211> LENGTH: 8471
<212> TYPE: DNA
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: EcoRI (GAATCC)-BamHI (GGATCC)-linearized
      Response Element Plasmid vector

<400> SEQUENCE: 64
ggatccttga cttgcggccg caactcccac ctgcaacatg cgtgactgac tgaggccgcg      60
actctagagt cgacctgcag gcatgcaagc ttgatatcaa gcttatcgat aatcaacctc     120
tggattacaa aatttgtgaa agattgactg gtattcttaa ctatgttgct ccttttacgc     180
tatgtggata cgctgcttta atgcctttgt atcatgctat tgcttcccgt atggctttca     240
ttttctcctc cttgtataaa tcctggttgc tgtctcttta tgaggagttg tggcccgttg     300
tcaggcaacg tggcgtggtg tgcactgtgt ttgctgacgc aacccccact ggttggggca     360
ttgccaccac ctgtcagctc ctttccggga ctttcgcttt ccccctccct attgccacgg     420
cggaactcat cgccgcctgc cttgcccgct gctggacagg ggctcggctg ttgggcactg     480
acaattccgt ggtgttgtcg gggaaatcat cgtcctttcc ttggctgctc gcctgtgttg     540
ccacctggat tctgcgcggg acgtccttct gctacgtccc ttcggccctc aatccagcgg     600
accttccttc ccgcggcctg ctgccggctc tgcggcctct tccgcgtctt cgccttcgcc     660
ctcagacgag tcggatctcc ctttgggccg cctccccgca tcgataccgt cgacctcgag     720
ggaattaatt cgagctcggt acctttaaga ccaatgactt acaaggcagc tgtagatctt     780
agccactttt taaaagaaaa ggggggactg gaagggctaa ttcactccca acgaagacaa     840
```

-continued

```
gatctgcttt ttgcttgtac tgggtctctc tggttagacc agatctgagc ctgggagctc      900
tctggctaac tagggaaccc actgcttaag cctcaataaa gcttgccttg agtgcttcaa      960
gtagtgtgtg cccgtctgtt gtgtgactct ggtaactaga gatccctcag acccttttag     1020
tcagtgtgga aaatctctag cagcatctag aattaattcc gtgtattcta tagtgtcacc     1080
taaatcgtat gtgtatgata cataaggtta tgtattaatt gtagccgcgt tctaacgaca     1140
atatgtacaa gcctaattgt gtagcatctg gcttactgaa gcagacccta tcatctctct     1200
cgtaaactgc cgtcagagtc ggtttggttg gacgaacctt ctgagtttct ggtaacgccg     1260
tcccgcaccc ggaaatggtc agcgaaccaa tcagcagggt catcgctagc cagatcctct     1320
acgccggacg catcgtggcc ggcatcaccg gcgccacagg tgcggttgct ggcgcctata     1380
tcgccgacat caccgatggg gaagatcggg ctcgccactt cgggctcatg agcgcttgtt     1440
tcggcgtggg tatggtggca ggccccgtgg ccggggggact gttgggcgcc atctccttgc     1500
atgcaccatt ccttgcggcg gcggtgctca acggcctcaa cctactactg ggctgcttcc     1560
taatgcagga gtcgcataag ggagagcgtc gaatggtgca ctctcagtac aatctagctc     1620
tgatgccgca tagttaagcc agccccgaca cccgccaaca cccgctgacg cgccctgacg     1680
ggcttgtctg ctcccggcat ccgcttacag acaagctgtg accgtctccg ggagctgcat     1740
gtgtcagagg ttttcaccgt catcaccgaa acgcgcgaga cgaaagggcc tcgtgatacg     1800
cctattttta taggttaatg tcatgataat aatggtttct tagacgtcag gtggcacttt     1860
tcggggaaat gtgcgcggaa cccctatttg tttatttttc taaatacatt caaatatgta     1920
tccgctcatg agacaataac cctgataaat gcttcaataa tattgaaaaa ggaagagtat     1980
gagtattcaa catttccgtg tcgcccttat tccctttttt gcggcatttt gccttcctgt     2040
ttttgctcac ccagaaacgc tggtgaaagt aaaagatgct gaagatcagt tgggtgcacg     2100
agtgggttac atcgaactgg atctcaacag cggtaagatc cttgagagtt ttcgccccga     2160
agaacgtttt ccaatgatga gcactttttaa agttctgcta tgtggcgcgg tattatcccg     2220
tattgacgcc gggcaagagc aactcggtcg ccgcatacac tattctcaga atgacttggt     2280
tgagtactca ccagtcacag aaaagcatct tacggatggc atgacagtaa gagaattatg     2340
cagtgctgcc ataaccatga gtgataacac tgcggccaac ttacttctga caacgatcgg     2400
aggaccgaag gagctaaccg cttttttgca caacatgggg gatcatgtaa ctcgccttga     2460
tcgttgggaa ccggagctga atgaagccat accaaacgac gagcgtgaca ccacgatgcc     2520
tgtagcaatg gcaacaacgt tgcgcaaact attaactggc gaactactta ctctagcttc     2580
ccggcaacaa ttaatagact ggatggaggc ggataaagtt gcaggaccac ttctgcgctc     2640
ggcccttccg gctggctggt ttattgctga taaatctgga gccggtgagc gtgggtctcg     2700
cggtatcatt gcagcactgg ggccagatgg taagccctcc cgtatcgtag ttatctacac     2760
gacggggagt caggcaacta tggatgaacg aaatagacag atcgctgaga taggtgcctc     2820
actgattaag cattggtaac tgtcagacca agtttactca tatatacttt agattgattt     2880
aaaacttcat ttttaattta aaaggatcta ggtgaagatc ctttttgata atctcatgac     2940
caaaatccct taacgtgagt tttcgttcca ctgagcgtca gaccccgtag aaaagatcaa     3000
aggatcttct tgagatcctt ttttctgcg cgtaatctgc tgcttgcaaa caaaaaaacc     3060
accgctacca gcggtggttt gtttgccgga tcaagagcta ccaactcttt ttccgaaggt     3120
aactggcttc agcagagcgc agataccaaa tactgtcctt ctagtgtagc cgtagttagg     3180
```

-continued

```
ccaccacttc aagaactctg tagcaccgcc tacatacctc gctctgctaa tcctgttacc   3240
agtggctgct gccagtggcg ataagtcgtg tcttaccggg ttggactcaa gacgatagtt   3300
accggataag gcgcagcggt cgggctgaac gggggggttcg tgcacacagc ccagcttgga   3360
gcgaacgacc tacaccgaac tgagatacct acagcgtgag ctatgagaaa gcgccacgct   3420
tcccgaaggg agaaaggcgg acaggtatcc ggtaagcggc agggtcggaa caggagagcg   3480
cacgagggag cttccagggg gaaacgcctg gtatctttat agtcctgtcg ggtttcgcca   3540
cctctgactt gagcgtcgat ttttgtgatg ctcgtcaggg gggcggagcc tatggaaaaa   3600
cgccagcaac gcggcctttt tacggttcct ggccttttgc tggccttttg ctcacatgtt   3660
ctttcctgcg ttatcccctg attctgtgga taaccgtatt accgcctttg agtgagctga   3720
taccgctcgc cgcagccgaa cgaccgagcg cagcgagtca gtgagcgagg aagcggaaga   3780
gcgcccaata cgcaaaccgc ctctccccgc gcgttggccg attcattaat gcagctgtgg   3840
aatgtgtgtc agttagggtg tggaaagtcc ccaggctccc cagcaggcag aagtatgcaa   3900
agcatgcatc tcaattagtc agcaaccagg tgtggaaagt ccccaggctc cccagcaggc   3960
agaagtatgc aaagcatgca tctcaattag tcagcaacca tagtcccgcc cctaactccg   4020
cccatcccgc ccctaactcc gcccagttcc gcccattctc cgccccatgg ctgactaatt   4080
tttttatttt atgcagaggc cgaggccgcc tcggcctctg agctattcca gaagtagtga   4140
ggaggctttt ttggaggcct aggcttttgc aaaaagcttg gacacaagac aggcttgcga   4200
gatatgtttg agaataccac tttatcccgc gtcagggaga ggcagtgcgt aaaaagacgc   4260
ggactcatgt gaaatactgg tttttagtgc gccagatctc tataatctcg cgcaacctat   4320
tttcccctcg aacacttttt aagccgtaga taaacaggct gggacacttc acatgagcga   4380
aaaatacatc gtcacctggg acatgttgca gatccatgca cgtaaactcg caagccgact   4440
gatgccttct gaacaatgga aaggcattat tgccgtaagc cgtggcggtc tgtaccgggt   4500
gcgttactgg cgcgtgaact gggtattcgt catgtcgata ccgtttgtat ttccagctac   4560
gatcacgaca accagcgcga gcttaaagtg ctgaaacgcg cagaaggcga tggcgaaggc   4620
ttcatcgtta ttgatgacct ggtggatacc ggtggtactg cggttgcgat cgtgaaatg   4680 tatccaaaag cgcactttgt caccatcttc gcaaaaccgg ctggtcgtcc gctggttgat   4740
gactatgttg ttgatatccc gcaagatacc tggattgaac agccgtggga tatgggcgtc   4800
gtattcgtcc cgccaatctc cggtcgctaa tcttttcaac gcctggcact gccgggcgtt   4860
gttcttttta acttcaggcg ggttacaata gtttccagta agtattctgg aggctgcatc   4920
catgacacag gcaaacctga gcgaaaccct gttcaaaccc cgctttaaac atcctgaaac   4980
ctcgacgcta gtccgccgct ttaatcacgg cgcacaaccg cctgtgcagt cggcccttga   5040
tggtaaaacc atccctcact ggtatcgcat gattaaccgt ctgatgtgga tctggcgcgg   5100
cattgaccca cgcgaaatcc tcgacgtcca ggcacgtatt gtgatgagcg atgccgaacg   5160
taccgacgat gatttatacg atacggtgat tggctaccgt ggcggcaact ggatttatga   5220
gtgggccccg gatctttgtg aaggaacctt acttctgtgg tgtgacataa ttggacaaac   5280
tacctacaga gatttaaagc tctaaggtaa atataaaatt tttaagtgta taatgtgtta   5340
aactactgat tctaattgtt tgtgtatttt agattccaac ctatggaact gatgaatggg   5400
agcagtggtg gaatgccttt aatgaggaaa acctgttttg ctcagaagaa atgccatcta   5460
gtgatgatga ggctactgct gactctcaac attctactcc tccaaaaaag aagagaaagg   5520
tagaagaccc caaggacttt ccttcagaat tgctaagttt tttgagtcat gctgtgttta   5580
```

-continued

```
gtaatagaac tcttgcttgc tttgctattt acaccacaaa ggaaaaagct gcactgctat    5640
acaagaaaat tatggaaaaa tattctgtaa cctttataag taggcataac agttataatc    5700
ataacatact gttttttctt actccacaca ggcatagagt gtctgctatt aataactatg    5760
ctcaaaaatt gtgtaccttt agcttttttaa tttgtaaagg ggttaataag gaatatttga    5820
tgtatagtgc cttgactaga gatcataatc agccatacca catttgtaga ggttttactt    5880
gctttaaaaa acctcccaca cctccccctg aacctgaaac ataaaatgaa tgcaattgtt    5940
gttgttaact tgtttattgc agcttataat ggttacaaat aaagcaatag catcacaaat    6000
ttcacaaata aagcattttt ttcactgcat tctagttgtg gtttgtccaa actcatcaat    6060
gtatcttatc atgtctggat caactggata actcaagcta accaaaatca tcccaaactt    6120 cccacccccat accctattac cactgccaat tacctagtgg tttcatttac tctaaacctg    6180
tgattcctct gaattatttt cattttaaag aaattgtatt tgttaaatat gtactacaaa    6240
cttagtagtt ggaagggcta attcactccc aaagaagaca agatatcctt gatctgtgga    6300
tctaccacac acaaggctac ttccctgatt agcagaacta cacaccaggg ccaggggtca    6360
gatatccact gacctttgga tggtgctaca agctagtacc agttgagcca gataaggtag    6420
aagaggccaa taaaggagag aacaccagct tgttacaccc tgtgagcctg catgggatgg    6480
atgacccgga gagagaagtg ttagagtgga ggtttgacag ccgcctagca tttcatcacg    6540
tggcccgaga gctgcatccg gagtacttca agaactgctg atatcgagct tgctacaagg    6600
gactttccgc tggggacttt ccaggggaggc gtggcctggg cgggactggg gagtggcgag    6660
ccctcagatc ctgcatataa gcagctgctt tttgcctgta ctgggtctct ctggttagac    6720
cagatctgag cctgggagct ctctggctaa ctagggaacc cactgcttaa gcctcaataa    6780
agcttgcctt gagtgcttca agtagtgtgt gcccgtctgt tgtgtgactc tggtaactag    6840
agatccctca dacccttttta gtcagtgtgg aaaatctcta gcagtggcgc ccgaacaggg    6900
acttgaaagc gaaagggaaa ccagaggagc tctctcgacg caggactcgg cttgctgaag    6960
cgcgcacggc aagaggcgag gggcggcgac tggtgagtac gccaaaaatt ttgactagcg    7020
gaggctagaa ggagagagat gggtgcgaga gcgtcagtat taagcggggg agaattagat    7080
cgcgatggga aaaaattcgg ttaaggccag ggggaaagaa aaaatataaa ttaaaacata    7140
tagtatgggc aagcagggag ctagaacgat tcgcagttaa tcctggcctg ttagaaacat    7200
cagaaggctg tagacaaata ctgggacagc tacaaccatc ccttcagaca ggatcagaag    7260
aacttagatc attatataat acagtagcaa ccctctattg tgtgcatcaa aggatagaga    7320
taaaagacac caaggaagct ttagacaaga tagaggaaga gcaaacaaa agtaagacca    7380 ccgcacagca agcggccggt gatcttcaga cctggacgat atatgagg gacaattgga    7440 gaagtgaatt atataaatat aaagtagtaa aaattgaacc attaggagta gcacccacca    7500
aggcaaagag aagagtggtg cagagagaaa aaagagcagt gggaatagga gctttgttcc    7560
ttgggttctt gggagcagca ggaagcacta tgggcgcagc gtcaatgacg ctgacggtac    7620
aggccagaca attattgtct ggtatagtgc agcagcagaa caatttgctg agggctattg    7680
aggcgcaaca gcatctgttg caactcacag tctggggcat caagcagctc caggcaagaa    7740
tcctggctgt ggaaagatac ctaaaggatc aacagctcct ggggatttgg ggttgctctg    7800
gaaaactcat ttgcaccact gctgtgcctt ggaatgctag ttggagtaat aaatctctgg    7860
aacagatttg gaatcacacg acctggatgg agtgggacag agaaattaac aattacacaa    7920
```

-continued

```
gcttaataca ctcccttaatt gaagaatcgc aaaaccagca agaaaagaat gaacaagaat    7980
tattggaatt agataaatgg gcaagtttgt ggaattggtt taacataaca aattggctgt    8040
ggtatataaa attattcata atgatagtag gaggcttggt aggtttaaga atagtttttg    8100
ctgtactttc tatagtgaat agagttaggc agggatattc accattatcg tttcagaccc    8160
acctcccaac cccgagggga cccgacaggc ccgaaggaat agaagaagaa ggtggagaga    8220
gagacagaga cagatccatt cgattagtga acggatctcg acggtatcgc caaatggcag    8280
tattcatcca caattttaaa agaaaagggg ggattggggg gtacagtgca ggggaaagaa    8340
tagtagacat aatagcaaca gacatacaaa ctaaagaatt acaaaaacaa attacaaaaa    8400
ttcaaaattt tcgggtttat tacagggaca gcagagatcc agtttggatc gataagcttg    8460
atatcgaatt c                                                        8471
```

<210> SEQ ID NO 65
<211> LENGTH: 591
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: pRay445B

<400> SEQUENCE: 65

```
Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
```

-continued

```
                  245              250              255
Ser Tyr Ala Met Asp Tyr Trp Gly Gln Gly Thr Ser Val Thr Val Ser
            260              265              270

Ser Thr Thr Thr Pro Ala Pro Arg Pro Pro Thr Pro Ala Pro Thr Ile
        275              280              285

Ala Ser Gln Pro Leu Ser Leu Arg Pro Glu Ala Cys Phe Met Tyr Val
    290              295              300

Ala Ala Ala Ala Phe Val Leu Leu Phe Phe Val Gly Cys Gly Val Leu
305              310              315              320

Leu Ser Lys Arg Lys Arg Lys His Met Gln Asn Ser His Ser Gly Val
            325              330              335

Asn Gln Leu Gly Gly Val Phe Val Asn Gly Arg Pro Leu Pro Asp Ser
            340              345              350

Thr Arg Gln Lys Ile Val Glu Leu Ala His Ser Gly Ala Arg Pro Cys
            355              360              365

Asp Ile Ser Arg Ile Leu Gln Val Ser Asn Gly Cys Val Ser Lys Ile
    370              375              380

Leu Gly Arg Tyr Tyr Glu Thr Gly Ser Ile Arg Pro Arg Ala Ile Gly
385              390              395              400

Gly Ser Lys Pro Arg Val Ala Thr Pro Glu Val Val Ser Lys Ile Ala
            405              410              415

Gln Tyr Lys Arg Glu Cys Pro Ser Ile Phe Ala Trp Glu Ile Arg Asp
            420              425              430

Arg Leu Leu Ser Glu Gly Val Cys Thr Asn Asp Asn Ile Pro Ser Val
            435              440              445

Ser Ser Ile Asn Arg Val Leu Arg Asn Leu Ala Ser Glu Lys Gln Gln
    450              455              460

Met Gly Ala Pro Thr Gln Ala Gly Glu Gly Thr Leu Ser Glu Ala Leu
465              470              475              480

Leu Gln Leu Gln Phe Asp Asp Glu Asp Leu Gly Ala Leu Leu Gly Asn
            485              490              495

Ser Thr Asp Pro Ala Val Phe Thr Asp Leu Ala Ser Val Asp Asn Ser
            500              505              510

Glu Phe Gln Gln Leu Leu Asn Gln Gly Ile Pro Val Ala Pro His Thr
            515              520              525

Thr Glu Pro Met Leu Met Glu Tyr Pro Glu Ala Ile Thr Arg Leu Val
    530              535              540

Thr Gly Ala Gln Arg Pro Pro Asp Pro Ala Pro Ala Pro Leu Gly Ala
545              550              555              560

Pro Gly Leu Pro Asn Gly Leu Leu Ser Gly Asp Glu Asp Phe Ser Ser
            565              570              575

Ile Ala Asp Met Asp Phe Ser Ala Leu Leu Ser Gln Ile Ser Ser
            580              585              590
```

```
<210> SEQ ID NO 66
<211> LENGTH: 658
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: pRay451C

<400> SEQUENCE: 66

Met Ala Leu Pro Val Thr Ala Leu Leu Leu Pro Leu Ala Leu Leu Leu
```

-continued

```
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
            35                  40                  45

Arg Val Thr Ile Ser Cys Arg Ala Ser Gln Asp Ile Ser Lys Tyr Leu
        50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
            115                 120                 125

Phe Gly Gly Gly Thr Lys Leu Glu Ile Thr Gly Gly Gly Gly Ser Gly
    130                 135                 140

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
            195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser Thr Thr Thr Pro Ala Pro Arg Pro Pro Thr Pro Ala Pro Thr Ile
            275                 280                 285

Ala Ser Gln Pro Leu Ser Leu Arg Pro Glu Ala Cys Phe Met Tyr Val
    290                 295                 300

Ala Ala Ala Ala Phe Val Leu Leu Phe Phe Val Gly Cys Gly Val Leu
305                 310                 315                 320

Leu Ser Lys Arg Lys Arg Lys His Met Gln Asn Ser His Ser Gly Val
                325                 330                 335

Asn Gln Leu Gly Gly Val Phe Val Asn Gly Arg Pro Leu Pro Asp Ser
            340                 345                 350

Thr Arg Gln Lys Ile Val Glu Leu Ala His Ser Gly Ala Arg Pro Cys
            355                 360                 365

Asp Ile Ser Arg Ile Leu Gln Val Ser Asn Gly Cys Val Ser Lys Ile
        370                 375                 380

Leu Gly Arg Tyr Tyr Glu Thr Gly Ser Ile Arg Pro Arg Ala Ile Gly
385                 390                 395                 400

Gly Ser Lys Pro Arg Val Ala Thr Pro Glu Val Val Ser Lys Ile Ala
                405                 410                 415

Gln Tyr Lys Arg Glu Cys Pro Ser Ile Phe Ala Trp Glu Ile Arg Asp
            420                 425                 430
```

-continued

```
Arg Leu Leu Ser Glu Gly Val Cys Thr Asn Asp Asn Ile Pro Ser Val
        435                 440                 445

Ser Ser Ile Asn Arg Val Leu Arg Asn Leu Ala Ser Glu Lys Gln Gln
    450                 455                 460

Met Gly Ala Asp Glu Phe Pro Thr Met Val Phe Pro Ser Gly Gln Ile
465                 470                 475                 480

Ser Gln Ala Ser Ala Leu Ala Pro Ala Pro Pro Gln Val Leu Pro Gln
                485                 490                 495

Ala Pro Ala Pro Ala Pro Ala Pro Ala Met Val Ser Ala Leu Ala Gln
                500                 505                 510

Ala Pro Ala Pro Val Pro Val Leu Ala Pro Gly Pro Pro Gln Ala Val
        515                 520                 525

Ala Pro Pro Ala Pro Lys Pro Thr Gln Ala Gly Glu Gly Thr Leu Ser
    530                 535                 540

Glu Ala Leu Leu Gln Leu Gln Phe Asp Asp Glu Asp Leu Gly Ala Leu
545                 550                 555                 560

Leu Gly Asn Ser Thr Asp Pro Ala Val Phe Thr Asp Leu Ala Ser Val
                565                 570                 575

Asp Asn Ser Glu Phe Gln Gln Leu Leu Asn Gln Gly Ile Pro Val Ala
                580                 585                 590

Pro His Thr Thr Glu Pro Met Leu Met Glu Tyr Pro Glu Ala Ile Thr
        595                 600                 605

Arg Leu Val Thr Gly Ala Gln Arg Pro Pro Asp Pro Ala Pro Ala Pro
    610                 615                 620

Leu Gly Ala Pro Gly Leu Pro Asn Gly Leu Leu Ser Gly Asp Glu Asp
625                 630                 635                 640

Phe Ser Ser Ile Ala Asp Met Asp Phe Ser Ala Leu Leu Ser Gln Ile
                645                 650                 655

Ser Ser
```

```
<210> SEQ ID NO 67
<211> LENGTH: 88
<212> TYPE: DNA
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: Compact 4X Pax6 Response Element

<400> SEQUENCE: 67
attttcacgc atgagtgcac agattttcac gcatgagtgc acagattttc acgcatgagt      60
gcacagattt tcacgcatga gtgcacag                                         88
```

```
<210> SEQ ID NO 68
<211> LENGTH: 1538
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(1538)
<223> OTHER INFORMATION: Single-vector design sequence
<220> FEATURE:
<221> NAME/KEY: MISC_FEATURE
<223> OTHER INFORMATION: Single-vector design

<400> SEQUENCE: 68
```

-continued

```
ggatccgccg ccaccatggc cttaccagtg accgccttgc tcctgccgct ggccttgctg        60
ctccacgccg ccaggccgga ttacaaagac gatgacgaca aacaggtcca actcgttcag       120
tccggcgcgg aagtaaaaaa acctggagcg tcagttaaag tatcctgtaa ggcgagtgga       180
tattcatttc ccgattatta cattaattgg gtgcgacaag cgcctggtca gggtcttgaa       240
tggatgggat ggatatactt cgcgtctggg aatagtgaat acaatcagaa atttaccggc       300
agggtgacga tgacgcgaga cacctccatt aatactgcct atatggaact cagctctctc       360
acttcagagg acacagccgt ctacttctgt gcctcccttt atgattacga ttggtatttt       420
gacgtgtggg gtcaaggaac tatggttact gtgtctagcg ggggaggtgg ctcaggtggg       480
ggaggttcag gaggaggcgg gtccgacatc gtgatgacac aaacccctct gagcctgagc       540
gttacgccag gcaaccagc ctccatttca tgcaagtcca gccagtcact cgtgcattca        600
aatggaaaca cctatctgca ctggtatctt caaaaaccag gtcagtcacc ccagttgttg       660
atatacaaag ttagtaatcg cttctccgga gtacccgatc ggttcagcgg gtctggttca       720
gggacggatt tcaccttgaa aattagccga gttgaggctg aagatgtggg aatttactat       780
tgcagtcaga gcagcattta cccctggacg ttcgggcagg gcaccaagtt ggaaattaag       840
accacgacgc cagcgccgcg accaccaaca ccggcgccca ccatcgcgtc gcagcccctg       900
tccctgcgcc cagaggcgtg ccggccagcg gcggggggcg cagtgcacac gaggggggctg      960 gacttcgcct gtgatatcta catctgggcg cccttggccg ggacttgtgg ggtccttctc     1020
ctgtcactgg ttatcaccct ttactgctcc ctaaaacggg gcagaaagaa actcctgtat      1080
atattcaaac aaccatttat gagaccagta caaactactc aagaggaaga tggctgtagc      1140
tgccgatttc agaagaaga agaaggagga tgtgaactga gagtgaagtt cagcaggagc       1200
gcagacgccc ccgcgtacaa gcagggccag aaccagctct ataacgagct caatctagga      1260
cgaagagagg agtacgatgt tttggacaag agacgtggcc gggaccctga gatggggg      1320 aagccgagaa ggaagaaccc tcaggaaggc ctgtacaatg aactgcagaa agataagatg      1380
gcggaggcct acagtgagat tgggatgaaa ggcgagcgcc ggaggggcaa ggggcacgat      1440
ggcctttacc agggtctcag tacagccacc aaggacacct acgacgccct tcacatgcag      1500
gccctgcctc ctcgctgaga tccttgactt gcggccgc                               1538
```

<210> SEQ ID NO 69
<211> LENGTH: 63
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Coding sequence for CD8a signal peptide
      sequence of SEQ ID NO: 68

<400> SEQUENCE: 69

```
atggccttac cagtgaccgc cttgctcctg ccgctggcct tgctgctcca cgccgccagg        60
ccg                                                                      63
```

<210> SEQ ID NO 70
<211> LENGTH: 24
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Coding sequence for FLAG tag of SEQ ID NO: 68

<400> SEQUENCE: 70
gattacaaag acgatgacga caaa                                                             24

<210> SEQ ID NO 71
<211> LENGTH: 738
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Coding sequence for anti-BCMA scFv of SEQ ID
      NO: 68

<400> SEQUENCE: 71
caggtccaac tcgttcagtc cggcgcggaa gtaaaaaaac ctggagcgtc agttaaagta        60
tcctgtaagg cgagtggata ttcatttccc gattattaca ttaattgggt gcgacaagcg       120
cctggtcagg gtcttgaatg gatgggatgg atatacttcg cgtctgggaa tagtgaatac       180
aatcagaaat ttaccggcag ggtgacgatg acgcgagaca cctccattaa tactgcctat       240
atggaactca gctctctcac ttcagaggac acagccgtct acttctgtgc ctcccttat        300 gattacgatt ggtattttga cgtgtggggt caaggaacta tggttactgt gtctagcggg       360
ggaggtggct caggtggggg aggttcagga ggaggcgggt ccgacatcgt gatgacacaa       420
acccctctga gcctgagcgt tacgccaggg caaccagcct ccatttcatg caagtccagc       480
cagtcactcg tgcattcaaa tggaaacacc tatctgcact ggtatcttca aaaaccaggt       540
cagtcacccc agttgttgat atacaaagtt agtaatcgct tctccggagt acccgatcgg       600
ttcagcgggt ctggttcagg gacggatttc accttgaaaa ttagccgagt tgaggctgaa       660
gatgtgggaa tttactattg cagtcagagc agcatttacc cctggacgtt cgggcagggc       720
accaagttgg aaattaag                                                              738

<210> SEQ ID NO 72
<211> LENGTH: 207
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Coding sequence for CD8 TMD of SEQ ID NO: 68

<400> SEQUENCE: 72
accacgacgc cagcgccgcg accaccaaca ccggcgccca ccatcgcgtc gcagcccctg        60
tccctgcgcc cagaggcgtg ccggccagcg gcggggggcg cagtgcacac gagggggctg       120
gacttcgcct gtgatatcta catctgggcg cccttggccg ggacttgtgg ggtccttctc       180
ctgtcactgg ttatcaccct ttactgc                                                   207

<210> SEQ ID NO 73
<211> LENGTH: 126
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Coding sequence for 4-1BB domain of SEQ ID NO:
      68

<400> SEQUENCE: 73
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 74
<211> LENGTH: 336
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Coding sequence for CD3z of SEQ ID NO: 68

<400> SEQUENCE: 74
agagtgaagt tcagcaggag cgcagacgcc cccgcgtaca agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga agataagat ggcggaggcc tacagtgaga ttgggatgaa aggcgagcgc     240 cggagggca aggggcacga tggcctttac caggtctca gtacagccac caaggacacc     300
tacgacgccc ttcacatgca ggccctgcct cctcgc                              336

<210> SEQ ID NO 75
<211> LENGTH: 500
<212> TYPE: DNA
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: PGK promoter sequence

<400> SEQUENCE: 75
gggtagggga ggcgcttttc ccaaggcagt ctggagcatg cgctttagca gccccgctgg      60
gcacttggcg ctacacaagt ggcctctggc ctcgcacaca ttccacatcc accggtaggc     120
gccaaccggc tccgttcttt ggtggcccct tcgcgccacc ttctactcct cccctagtca     180
ggaagttccc ccccgccccg cagctcgcgt cgtgcaggac gtgacaaatg gaagtagcac     240
gtctcactag tctcgtgcag atggacagca ccgctgagca atggaagcgg gtaggccttt     300
ggggcagcgg ccaatagcag ctttgctcct tcgctttctg ggctcagagg ctgggaaggg     360
gtgggtccgg gggcgggctc aggggcgggc tcaggggcgg ggcgggcgcc cgaaggtcct     420
ccggaggccc ggcattctgc acgcttcaaa agcgcacgtc tgccgcgctg ttctcctctt     480
cctcatctcc gggcctttcg                                                500

<210> SEQ ID NO 76
<211> LENGTH: 6
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Leu or Gln
<220> FEATURE:
<221> NAME/KEY: MISC_FEATURE
<223> OTHER INFORMATION: cleavage sequence -continued

```
<400> SEQUENCE: 76

Pro Xaa Gly Met Thr Ser
1               5

<210> SEQ ID NO 77
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Leu or Gln
<220> FEATURE:
<221> NAME/KEY: MISC_FEATURE
<223> OTHER INFORMATION: cleavage sequence

<400> SEQUENCE: 77

Pro Xaa Gly Met Thr
1               5

<210> SEQ ID NO 78
<211> LENGTH: 7
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: tobacco etch virus (TEV) protease cleavage site

<400> SEQUENCE: 78

Glu Asn Leu Tyr Thr Gln Ser
1               5

<210> SEQ ID NO 79
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: enterokinase cleavage site

<400> SEQUENCE: 79

Asp Asp Asp Asp Lys
1               5

<210> SEQ ID NO 80
<211> LENGTH: 4
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<223> OTHER INFORMATION: thrombin cleavage site

<400> SEQUENCE: 80

Leu Val Pro Arg
1
```